US009248179B2

(12) United States Patent
Wu et al.

(10) Patent No.: US 9,248,179 B2
(45) Date of Patent: Feb. 2, 2016

(54) PAN-LYSSAVIRUS VACCINES AGAINST RABIES

(75) Inventors: Xianfu Wu, Atlanta, GA (US); Charles E. Rupprecht, Lawrenceville, GA (US); Ivan V. Kuzmin, Lilburn, GA (US)

(73) Assignee: The United States of America, as represented by the Secretary of the Department of Health and Human Services, Centers for Disease Control and Prevention, Washington, DC (US)

( * ) Notice: Subject to any disclaimer, the term of this patent is extended or adjusted under 35 U.S.C. 154(b) by 270 days.

(21) Appl. No.: 13/806,622

(22) PCT Filed: Jun. 23, 2011

(86) PCT No.: PCT/US2011/041579

§ 371 (c)(1), (2), (4) Date: Dec. 21, 2012

(87) PCT Pub. No.: WO2011/163446

PCT Pub. Date: Dec. 29, 2011

(65) Prior Publication Data

US 2013/0095137 A1 Apr. 18, 2013

Related U.S. Application Data

(60) Provisional application No. 61/358,288, filed on Jun. 24, 2010.

(51) Int. Cl.

*A61K 39/205* (2006.01)
*A61K 39/12* (2006.01)
*C07K 14/005* (2006.01)
*C12N 7/00* (2006.01)
*C12N 15/86* (2006.01)
*A61K 39/00* (2006.01)

(52) U.S. Cl.

CPC ............... *A61K 39/205* (2013.01); *A61K 39/12* (2013.01); *C07K 14/005* (2013.01); *C12N 7/00* (2013.01); *C12N 15/86* (2013.01); *A61K 2039/5256* (2013.01); *A61K 2039/70* (2013.01); *C12N 2760/20122* (2013.01); *C12N 2760/20134* (2013.01); *C12N 2760/20143* (2013.01); *C12N 2760/20152* (2013.01); *C12N 2800/50* (2013.01)

(58) Field of Classification Search

None

See application file for complete search history.

(56) References Cited

U.S. PATENT DOCUMENTS

| | | | | |
|---|---|---|---|---|
| 2002/0091590 | A1 | 7/2002 | Edgar et al. | |
| 2002/0164356 | A1 | 11/2002 | Mebatsion | |
| 2003/0113346 | A1 | 6/2003 | Dietzchold et al. | |
| 2005/0064389 | A1 | 3/2005 | Jacob et al. | |
| 2008/0274130 | A1 * | 11/2008 | Rupprecht et al. | 424/185.1 |

FOREIGN PATENT DOCUMENTS

| | | |
|---|---|---|
| WO | WO 89/00861 | 2/1989 |
| WO | WO 2007/047459 | 4/2007 |
| WO | WO 2010/033337 | 3/2010 |

OTHER PUBLICATIONS

GenBank Accession No. S59448 (Mokola virus, lyssavirus serotype 3, genomic RNA), deposited Jul. 23, 1993.

GenBank Accession No. AF429312 (Lagos bat virus strain 8619NGA glycoprotein mRNA), deposited Oct. 24, 2006.

GenBank Accession No. EF614258 (West Caucasian bat virus, complete genome), deposited Jul. 18, 2008.

Search Report dated Feb. 19, 2014, issued in connection with China Application No. 201180040773.7.

Badrane et al., "Evidence of Two *Lyssavirus* Phylogroups with Distinct Pathogenicity and Immunogenicity," *J. Virol*., vol. 75(7):3268-3276, 2001.

Botvinkin et al., "Novel Lyssaviruses Isolated from Bats in Russia," *Emerg. Infect. Dis*., vol. 9(12):1623-1625, 2003.

Hanlon et al., "Efficacy of Rabies Biologics Against New Lyssaviruses from Eurasia," *Virus Res*., vol. 111:44-54, 2005.

Kuzmin et al., "Possible Emergence of West Caucasian Bat Virus in Africa," *Emerg. Infect. Dis*., vol. 14(12):1887-1889, 2008.

Mebatsion et al., "Mokola Virus Glycoprotein and Chimeric Proteins Can Replace Rabies Virus Glycoprotein in the Rescue of Infectious Defective Rabies Virus Particles," *J. Virol*., vol. 69(3):1444-1451, 1995.

Nel et al., "A Comparison of DNA Vaccines for the Rabies-Related Virus, Mokola," *Vaccine*, vol. 21:2598-2606, 2003.

Weyer et al., "Cross-Protective and Cross-Reactive Immune Responses to Recombinant Vaccinia Viruses Expressing Full-Length Lyssavirus Glycoprotein Genes," *Epidemiol. Infect*., vol. 136:670-678, 2008.

World Organisation for Animal Health, "Rabies", *OIE Terrestrial Manual*, Chapter 2.1.13, pp. 304-323, 2008.

* cited by examiner

*Primary Examiner* — Michelle S Horning
(74) *Attorney, Agent, or Firm* — Klarquist Sparkman, LLP

(57) ABSTRACT

Described herein are recombinant rabies viruses encoding rabies virus glycoprotein and at least one heterologous glycoprotein from another *lyssavirus*, such as Mokola virus, Lagos bat virus and/or West Caucasian bat virus. In particular embodiments, the recombinant rabies virus includes two or three heterologous *lyssavirus* glycoproteins. The disclosed recombinant rabies viruses can be used as pan-*lyssavirus* vaccines to provide protection against *lyssaviruses* that cause rabies.

15 Claims, 5 Drawing Sheets

Construction of transcription plasmid for ERA +cDNA

N P M G psi L
ERA backbone
N P M G* psi L
ERA with G333 mutation
N P M G* psi L
Trans unit 1
Trans unit 2
ERA with two introduced transcriptional (trans) units
Insert MOKV and WCBV G genes
N P MOKV G M G* psi WCBV G L
ERA with three glycoprotein genes (ERA-3G)

FIG. 5

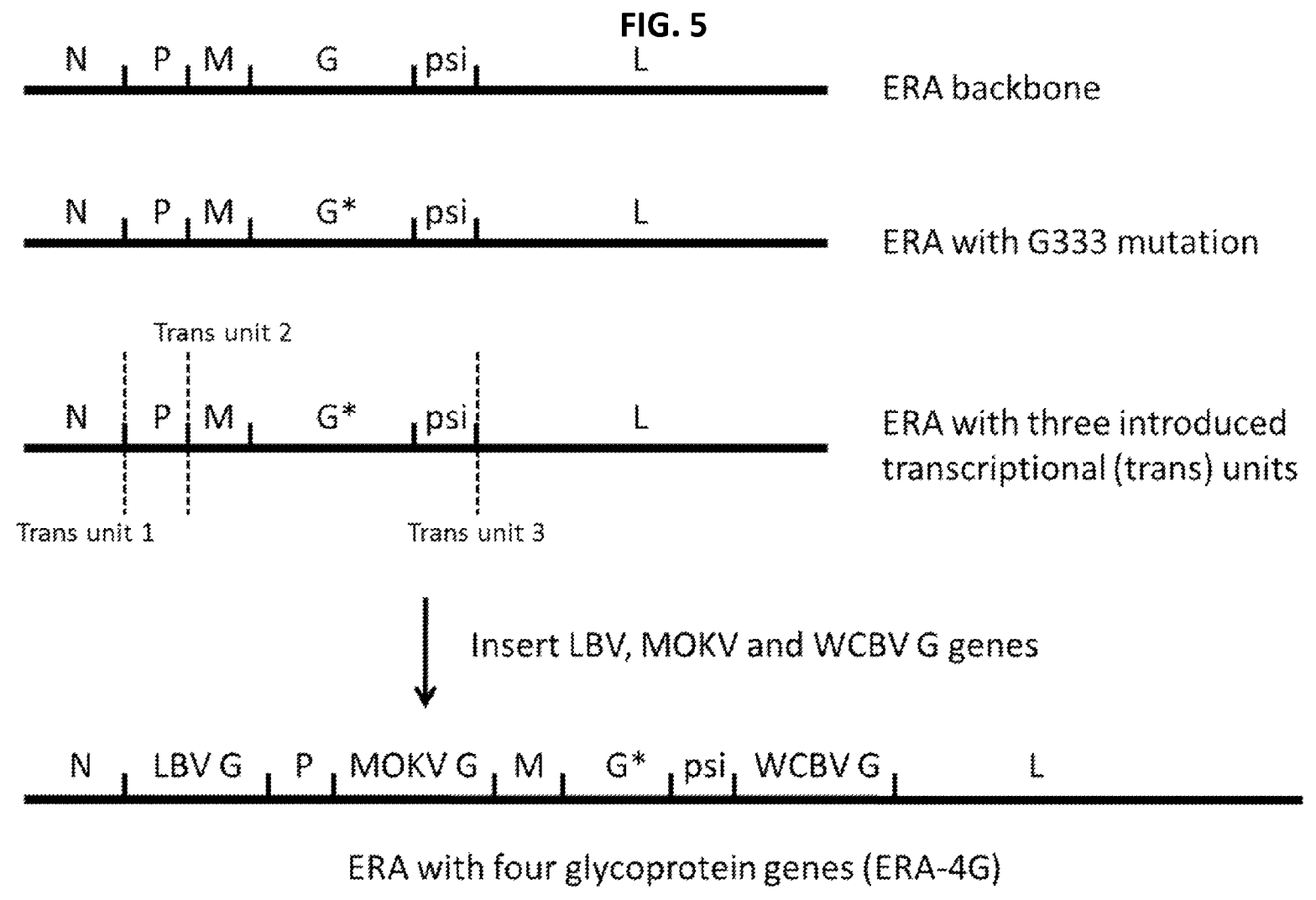

N P M G psi L
ERA backbone

N P M G* psi L
ERA with G333 mutation

Trans unit 1
Trans unit 2
Trans unit 3
N P M G* psi L
ERA with three introduced transcriptional (trans) units Insert LBV, MOKV and WCBV G genes N LBV G P MOKV G M G* psi WCBV G L
ERA with four glycoprotein genes (ERA-4G)

PAN-LYSSAVIRUS VACCINES AGAINST RABIES

CROSS REFERENCE TO RELATED APPLICATIONS

This is the U.S. National Stage of International Application No. PCT/US2011/041579, filed Jun. 23, 2011, published in English under PCT Article 21(2), which claims the benefit of U.S. Provisional Application No. 61/358,288, filed Jun. 24, 2010, which is herein incorporated by reference in its entirety.

FIELD

This disclosure concerns recombinant rabies viruses and their use as pan-*lyssavirus* vaccines for protection against *lyssavirus* infections.

BACKGROUND

The genus *Lyssavirus* is a member of the Rhabdoviridae family within the order Mononegavirales (viruses with a single-stranded, negative sense genome). *Lyssaviruses* are the etiological agents of rabies encephalitis in warm-blooded animals and humans (Tordo et al., "*Lyssaviruses*" In Fauquet et al. eds. *Virus taxonomy: the classification and nomenclature of viruses. The 8th Report of the International Committee on Taxonomy of Viruses*. San Diego: Oxford Academic, 2006, pages 623-629; World Health Organization Expert Consultation on Rabies, 5-8 Oct. 2004, first report, World Health Organization Technical report series 931, Geneva: World Health Organization, 2005, pages 15-19). *Lyssavirus* species include rabies virus (RABV; genotype 1), Lagos bat virus (LBV; genotype 2), Mokola virus (MOKV; genotype 3), Duvenhage virus (DUVV; genotype 4), European bat *lyssavirus*-1 (EBLV-1; genotype 5), European bat *lyssavirus*-2 (EBLV-2; genotype 6), Australian bat *lyssavirus* (ABLV; genotype 7) and four additional species isolated from bats in central Asia and Russia (Aravan virus—ARAV; Khujand virus—KHUV; Irkut virus—IRKV; and West Caucasian bat virus—WCBV) (Kuzmin et al., *Emerg. Infect. Dis.* 14(12): 1887-1889, 2008; Weyer et al., *Epidemiol. Infect.* 136:670-678, 2007; Kuzmin and Rupprecht, "Bat rabies" In Rabies, 2nd Edition, New York, Academic Press, 2007, pages 259-307, Jackson and Wunner, eds.).

Based on phylogeny, immunogenicity and virulence of *lyssavirus* isolates, two *lyssavirus* phylogroups have been proposed (Badrane et al., *J. Virol.* 75:3268-3276, 2001). The division into phylogroups generally correlates with the pattern of vaccine cross-protection observed for *lyssaviruses* (Badrane et al., *J. Virol.* 75:3268-3276, 2001; Hanlon et al., *Virus Res.* 111:44-54, 2005; Nel et al., *Expert Rev. Vaccines* 4:553-540, 2005). Phylogroup 1 includes genotypes 1, 4, 5, 6 and 7, as well as ARAV, KHUV and IRKV (Kuzmin et al., *Virus Res.* 97:65-79, 2003; Kuzmin et al., *Virus Res.* 111:28-43, 2005; Hanlon et al., *Virus Res.* 111:44-54, 2005). Currently available commercial vaccines and biologicals are considered to be effective against infections of viruses from this phylogroup (Nel et al., *Expert Rev. Vaccines* 4:553-540, 2005). However, these vaccines and biologics for rabies do not offer full protection against infection with viruses outside of *lyssavirus* phylogroup 1 (i.e., genotypes 2 and 3). In addition, WCBV is recognized as the most divergent *lyssavirus* and exhibits limited relatedness to genotype 2 and 3 viruses. Previous studies have demonstrated little or no cross-neutralization of anti-RABV sera with WCBV (Botvinkin et al., *Emerg. Infect. Dis.* 9:1623-1625, 2003; Hanlon et al., *Virus Res.* 111:44-54, 2005).

Thus, a need exists to develop a rabies vaccine that can protect against a broad spectrum of *lyssaviruses*, particularly WCBV and *lyssaviruses* of genotypes 2 and 3.

SUMMARY

Disclosed herein are recombinant rabies viruses having glycoprotein genes from at least two different *lyssaviruses*. The disclosed viruses can be used as pan-*lyssavirus* vaccines to provide protection against infection by multiple genotypes of *lyssavirus*.

Provided herein are recombinant rabies viruses. In some embodiments, the genome of the recombinant rabies virus includes rabies virus nucleoprotein (N), phosphoprotein (P), matrix protein (M), RNA-dependent RNA polymerase (L) and glycoprotein (G) genes and at least one, at least two or at least three different heterologous *lyssavirus* glycoprotein genes. In some embodiments, the *lyssavirus* is selected from LBV, MOKV, DUVV, EBLV-1, EBLV-2, ABLV, ARAV, KHUV, IRKV and WCBV. In particular embodiments, the *lyssavirus* is selected from LBV, MOKV and WCBV.

Further provided is a vector comprising a full-length rabies virus antigenomic DNA. In some embodiments, the antigenomic DNA includes rabies virus N, P, M, L and G genes, and the vector further includes at least one, at least two, or at least three different heterologous *lyssavirus* G genes. Also provided are cells comprising a rabies virus vector described herein.

Also provided are compositions comprising one or more recombinant rabies viruses described herein and a pharmaceutically acceptable carrier. Methods of eliciting an immune response in a subject against *lyssavirus* by administering to the subject one or more of the recombinant rabies viruses disclosed herein is further provided.

The foregoing and other objects, features, and advantages of the invention will become more apparent from the following detailed description, which proceeds with reference to the accompanying figures.

BRIEF DESCRIPTION OF THE FIGURES

FIG. 5: Schematic of the construction of ERA-4G. The G333 mutation is introduced into the ERA backbone and three transcriptional (trans) units are added. The transcriptional units are introduced between the N and P genes, between the P and M genes, and between the G and L genes. The LBV, MOKV and WCBV G genes are cloned into the transcriptional units to form a recombinant ERA rabies virus with four glycoprotein genes (ERA-4G).

SEQUENCE LISTING

Figure 1A:
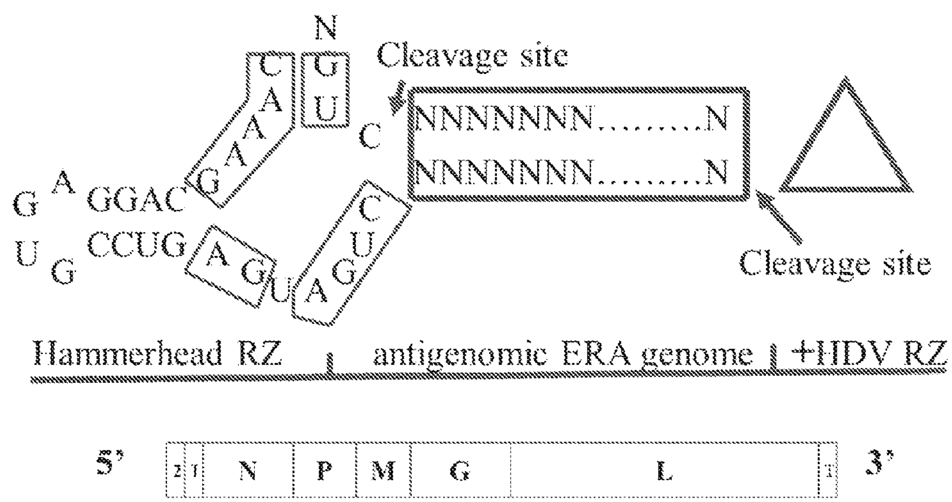
FIG. 1A: Schematic illustration of the ERA transcription plasmid. Positions of the hammerhead ribozymes and antigenomic ERA genome are indicated graphically. Relative positions of the N, P, M G and L proteins are shown in a 5' to 3' direction.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Dec. 20, 2012, 135 KB, which is incorporated by reference herein. In the accompanying sequence listing:

SEQ ID NO: 1 is the nucleotide sequence of recombinant rabies virus ERA recovered by reverse genetics. Nucleotides 4370-4372 of the recombinant virus have been changed (relative to the wild-type virus) from aga to gag, which introduces an Arg to Glu amino acid change in the G protein at residue 333.

SEQ ID NO: 2 is the amino acid sequence of the rabies virus ERA N protein.

SEQ ID NO: 3 is the amino acid sequence of the rabies virus ERA P protein.

SEQ ID NO: 4 is the amino acid sequence of the rabies virus ERA M protein.

SEQ ID NO: 5 is the amino acid sequence of the rabies virus ERA G protein mutated at amino acid position 333 (from Arg to Glu).

SEQ ID NO: 6 is the amino acid sequence of the rabies virus ERA L protein.

SEQ ID NO: 7 is the amino acid sequence of the wild-type rabies virus ERA G protein.

SEQ ID NOs: 8-11 are the nucleotide sequences of RT-PCR primers for amplification of full-length rabies virus genomic cDNA.

SEQ ID NOs: 12-15 are oligonucleotide sequences used to synthesize hammerhead and hepatitis delta virus ribozymes.

SEQ ID NOs: 16-40 are the nucleotide sequences of PCR primers.

SEQ ID NOs: 41 and 42 are the nucleotide sequences of transcription units for incorporating heterologous ORFs.

SEQ ID NOs: 43 and 44 are the nucleotide sequences of RT-PCR primers for amplification of the MOKV G gene.

SEQ ID NOs: 45 and 46 are the nucleotide sequences of RT-PCR primers for amplification of the WCBV G gene.

SEQ ID NOs: 47 and 48 are the nucleotide and amino acid sequences, respectively, of MOKV G.

SEQ ID NOs: 49 and 50 are the nucleotide and amino acid sequences, respectively, of WCBV G.

SEQ ID NOs: 51 and 52 are the nucleotide sequences of RT-PCR primers for amplification of the LBV G gene.

SEQ ID NOs: 53 and 54 are the nucleotide and amino acid sequences, respectively, of LBV G.

DETAILED DESCRIPTION

I. Abbreviations

ABLV Australian bat *lyssavirus*
ARAV Aravan virus
CMV cytomegalovirus
DFA direct fluorescent antibody
DUVV Duvenhage virus
EBLV-1 European bat *lyssavirus*-1
EBLV-2 European bat *lyssavirus*-2
ERA Evelyn-Rokitnicki-Abelseth
FFU focus-forming unit
G glycoprotein
i.m. intramuscular
IRES internal ribosome entry site
IRKV Irkut virus
KHUV Khujand virus
L RNA-dependent RNA polymerase
LBV Lagos bat virus
M matrix protein
MOKV Mokola virus
N nucleoprotein
NLS nuclear localization signal
ORF open reading frame
P phosphoprotein
PAGE polyacrylamide gel electrophoresis
RABV rabies virus
RNP ribonucleoprotein
RABV rabies virus
WCBV West Caucasian bat virus

II. Terms and Methods

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Adjuvant: A substance or vehicle that non-specifically enhances the immune response to an antigen. Adjuvants can include a suspension of minerals (alum, aluminum hydroxide, or phosphate) on which antigen is adsorbed; or water-in-oil emulsion in which antigen solution is emulsified in mineral oil (for example, Freund's incomplete adjuvant), sometimes with the inclusion of killed mycobacteria (Freund's complete adjuvant) to further enhance antigenicity. Immunostimulatory oligonucleotides (such as those including a CpG motif) can also be used as adjuvants (for example, see U.S. Pat. Nos. 6,194,388; 6,207,646; 6,214,806; 6,218,371; 6,239,116; 6,339,068; 6,406,705; and 6,429,199). Adjuvants also include biological molecules, such as co-stimulatory molecules. Exemplary biological adjuvants include IL-2, RANTES, GM-CSF, TNF-α, IFN-γ, G-CSF, LFA-3, CD72, B7-1, B7-2, OX-40L and 41 BBL.

Administer: As used herein, administering a composition, such as a vaccine, to a subject means to give, apply or bring the composition into contact with the subject. Administration can be accomplished by any of a number of routes, such as, for example, topical, oral, subcutaneous, intramuscular, intraperitoneal, intravenous, intrathecal and intramuscular.

Animal: Living multi-cellular vertebrate organisms, a category that includes, for example, mammals and birds. The term mammal includes both human and non-human mammals. The term "animal" includes both human and veterinary subjects, for example, humans, non-human primates, dogs, cats, horses, raccoons, bats, rats, mice, foxes, squirrels, opossum, coyotes, wolves and cows.

Antibody: A protein (or protein complex) that includes one or more polypeptides substantially encoded by immunoglobulin genes or fragments of immunoglobulin genes. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is generally a tetramer. Each tetramer is composed of two identical pairs of polypeptide chains, each pair having one "light" (about 25 kDa) and one "heavy" (about 50-70 kDa) chain. The N-terminus of each chain defines a variable region of about 100 to 110 or more amino acids primarily responsible for antigen recognition. The terms "variable light chain" ($V_L$) and "variable heavy chain" ($V_H$) refer, respectively, to these light and heavy chains.

As used herein, the term "antibody" includes intact immunoglobulins as well as a number of well-characterized fragments. For instance, Fabs, Fvs, and single-chain Fvs (SCFvs) that bind to target protein (or epitope within a protein or fusion protein) would also be specific binding agents for that protein (or epitope). These antibody fragments are as follows: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) $(Fab')_2$, the fragment of the antibody obtained by treating whole antibody with the enzyme pepsin without subsequent reduction; (4) $F(ab')_2$, a dimer of two Fab' fragments held together by two disulfide bonds; (5) Fv, a genetically engineered fragment containing the variable region of the light chain and the variable region of the heavy chain expressed as two chains; and (6) single chain antibody, a genetically engineered molecule containing the variable region of the light chain, the variable region of the heavy chain, linked by a suitable polypeptide linker as a genetically fused single chain molecule. Methods of making these fragments are routine (see, for example, Harlow and Lane, *Using Antibodies: A Laboratory Manual*, CSHL, New York, 1999).

Antibody binding affinity: The strength of binding between a single antibody binding site and a ligand (e.g., an antigen or epitope). The affinity of an antibody binding site X for a ligand Y is represented by the dissociation constant ($K_d$), which is the concentration of Y that is required to occupy half of the binding sites of X present in a solution. A smaller $K_d$ indicates a stronger or higher-affinity interaction between X and Y and a lower concentration of ligand is needed to occupy the sites. In general, antibody binding affinity can be affected by the alteration, modification and/or substitution of one or more amino acids in the epitope recognized by the antibody paratope. Binding affinity can be measured using any technique known in the art, such as end-point titration in an Ag-ELISA assay.

Antigen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens.

Antigenomic: In the context of a virus with a negative-strand RNA genome (such as the genome of a *lyssavirus*), "antigenomic" refers to the complement (positive strand) of the negative strand genome.

Attenuated: In the context of a live virus, such as a rabies virus, the virus is attenuated if its ability to infect a cell or subject and/or its ability to produce disease is reduced (for example, eliminated). Typically, an attenuated virus retains at least some capacity to elicit an immune response following administration to an immunocompetent subject. In some cases, an attenuated virus is capable of eliciting a protective immune response without causing any signs or symptoms of infection.

Epitope: An antigenic determinant. These are particular chemical groups, such as contiguous or non-contiguous peptide sequences, on a molecule that are antigenic, that is, that elicit a specific immune response. An antibody binds a particular antigenic epitope based on the three dimensional structure of the antibody and the matching (or cognate) three dimensional structure of the epitope.

Evelyn-Rokitnicki-Abelseth (ERA): The ERA strain of rabies virus was derived from the Street-Alabama-Dufferin (SAD) strain, first isolated from a rabid dog in Alabama (USA) in 1935. The ERA strain was derived after multiple passages of SAD rabies virus in mouse brains, baby hamster kidney (BHK) cells, and chicken embryos.

Fusion protein: A protein generated by expression of a nucleic acid sequence engineered from nucleic acid sequences encoding at least a portion of two different (heterologous) proteins. To create a fusion protein, the nucleic acid sequences must be in the same reading frame and contain no internal stop codons in that frame.

Heterologous: As used herein, a "heterologous nucleic acid sequence" is a nucleic acid sequence that is derived from a different source, species or strain. In some embodiments described herein, the heterologous nucleic acid sequence is a nucleic acid sequence encoding a glycoprotein from a *lyssavirus* other than rabies virus ERA. In the context of a recombinant ERA rabies virus, a heterologous nucleic acid sequence is any nucleic acid sequence that is not derived from the ERA rabies virus.

Immune response: A response of a cell of the immune system, such as a B-cell, T-cell, macrophage or polymorphonucleocyte, to a stimulus such as an antigen. An immune response can include any cell of the body involved in a host defense response, including for example, an epithelial cell that secretes an interferon or a cytokine. An immune response includes, but is not limited to, an innate immune response or inflammation. As used herein, a protective immune response refers to an immune response that protects a subject from infection (prevents infection or prevents the development of disease associated with infection).

Immunize: To render a subject protected from a disease (for example, an infectious disease), such as by vaccination.

Immunogen: A compound, composition, or substance which is capable, under appropriate conditions, of stimulating an immune response, such as the production of antibodies or a T-cell response in an animal, including compositions that are injected or absorbed into an animal. As used herein, an "immunogenic composition" is a composition comprising an immunogen.

Immunogenic composition: A composition useful for stimulating or eliciting a specific immune response (or immunogenic response) in a vertebrate. In some embodiments, the immunogenic composition includes a recombinant rabies virus, such as a recombinant rabies virus expressing one or more heterologous glycoproteins (such as the glycoproteins from MOKV, LBV or WCBV). In some embodiments, the immunogenic response is protective or provides protective immunity, in that it enables the animal to better resist infection with or disease progression from the pathogen against which the immunogenic composition is directed (e.g., rabies virus and other *lyssaviruses*). One specific example of a type of immunogenic composition is a vaccine.

In some embodiments, an "effective amount" or "immune-stimulatory amount" of an immunogenic composition is an amount which, when administered to a subject, is sufficient to engender a detectable immune response. Such a response may comprise, for instance, generation of antibodies specific to one or more of the epitopes provided in the immunogenic composition. Alternatively, the response may comprise a T-helper or CTL-based response to one or more of the epitopes provided in the immunogenic composition. In other embodiments, a "protective effective amount" of an immunogenic composition is an amount which, when administered to an animal, is sufficient to confer protective immunity upon the animal.

Inhibiting or treating a disease: Inhibiting the full development of a disease or condition, for example, in a subject who is at risk for a disease. One specific example of a disease is rabies. "Treatment" refers to a therapeutic intervention that ameliorates a sign or symptom of a disease or pathological condition after it has begun to develop. As used herein, the term "ameliorating," with reference to a disease, pathological condition or symptom, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease.

Isolated: An "isolated" or "purified" biological component (such as a nucleic acid, peptide, protein, protein complex, or particle) has been substantially separated, produced apart from, or purified away from other biological components in the cell of the organism in which the component naturally occurs, that is, other chromosomal and extra-chromosomal DNA and RNA, and proteins. Nucleic acids, peptides and proteins that have been "isolated" or "purified" thus include nucleic acids and proteins purified by standard purification methods. The term also embraces nucleic acids, peptides and proteins prepared by recombinant expression in a host cell, as well as chemically synthesized nucleic acids or proteins. The term "isolated" or "purified" does not require absolute purity; rather, it is intended as a relative term. Thus, for example, an isolated biological component is one in which the biological component is more enriched than the biological component is in its natural environment within a cell, or other production vessel. Preferably, a preparation is purified such that the biological component represents at least 50%, such as at least 70%, at least 90%, at least 95%, or greater, of the total biological component content of the preparation.

Label: A detectable compound or composition that is conjugated directly or indirectly to another molecule to facilitate detection of that molecule. Specific, non-limiting examples of labels include fluorescent tags, enzymatic linkages, and radioactive isotopes.

*Lyssavirus*: A genus of viruses that is part of the Rhabdoviridae family within the order Mononegavirales (viruses with a single-stranded, negative sense genome). *Lyssaviruses* are the etiological agents of rabies encephalitis in warm-blooded animals and humans. *Lyssavirus* species include rabies virus (RABV; genotype 1), Lagos bat virus (LBV; genotype 2), Mokola virus (MOKV; genotype 3), Duvenhage virus (DUVV; genotype 4), European bat *lyssavirus*-1 (EBLV-1; genotype 5), European bat *lyssavirus*-2 (EBLV-2; genotype 6) Australian bat *lyssavirus* (ABLV; genotype 7) and four additional species isolated from bats in central Asia and Russia (Aravan virus—ARAV; Khujand virus—KHUV; Irkut virus—IRKV; and West Caucasian bat virus—WCBV) (Kuzmin et al., *Emerg. Infect. Dis.* 14(12):1887-1889, 2008; Weyer et al., *Epidemiol. Infect.* 136:670-678, 2007; Kuzmin and Rupprecht, "Bat rabies" In Rabies, $2^{nd}$ Edition, New York, Academic Press, 2007, pages 259-307, Jackson and Wunner, eds.).

ORF (open reading frame): A series of nucleotide triplets (codons) coding for amino acids without any termination codons. These sequences are usually translatable into a peptide.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame. If introns are present, the operably linked DNA sequences may not be contiguous.

Pharmaceutically acceptable carriers: The pharmaceutically acceptable carriers useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compounds or molecules, proteins or antibodies that bind these proteins, viruses or vectors, and additional pharmaceutical agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Plasmid: A circular nucleic acid molecule capable of autonomous replication in a host cell.

Polypeptide: A polymer in which the monomers are amino acid residues joined together through amide bonds. When the amino acids are alpha-amino acids, either the L-optical isomer or the D-optical isomer can be used, the L-isomers being preferred for many biological uses. The terms "polypeptide" or "protein" as used herein are intended to encompass any amino acid molecule and include modified amino acid molecules. The term "polypeptide" is specifically intended to cover naturally occurring proteins, as well as those which are recombinantly or synthetically produced.

Conservative amino acid substitutions are those substitutions that, when made, least interfere with the properties of the original protein, that is, the structure and especially the function of the protein is conserved and not significantly changed by such substitutions. Examples of conservative substitutions are shown below.

| Original Residue | Conservative Substitutions |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Conservative substitutions generally maintain (a) the structure of the polypeptide backbone in the area of the substitution, for example, as a sheet or helical conformation, (b) the charge or hydrophobicity of the molecule at the target site, or (c) the bulk of the side chain.

Amino acids are typically classified in one or more categories, including polar, hydrophobic, acidic, basic and aromatic, according to their side chains. Examples of polar amino acids include those having side chain functional groups such as hydroxyl, sulfhydryl, and amide, as well as the acidic and basic amino acids. Polar amino acids include, without limitation, asparagine, cysteine, glutamine, histidine, selenocysteine, serine, threonine, tryptophan and tyrosine. Examples of hydrophobic or non-polar amino acids include those residues having nonpolar aliphatic side chains, such as, without limitation, leucine, isoleucine, valine, glycine, alanine, proline, methionine and phenylalanine. Examples of basic amino acid residues include those having a basic side chain, such as an amino or guanidino group. Basic amino acid residues include, without limitation, arginine, homolysine and lysine. Examples of acidic amino acid residues include those having an acidic side chain functional group, such as a carboxy group. Acidic amino acid residues include, without limitation aspartic acid and glutamic acid. Aromatic amino acids include those having an aromatic side chain group. Examples of aromatic amino acids include, without limitation, biphenylalanine, histidine, 2-napthylalananine, pentafluorophenylalanine, phenylalanine, tryptophan and tyrosine. It is noted that some amino acids are classified in more than one group, for example, histidine, tryptophan, and tyrosine are classified as both polar and aromatic amino acids. Additional amino acids that are classified in each of the above groups are known to those of ordinary skill in the art.

Substitutions which in general are expected to produce the greatest changes in protein properties will be non-conservative, for instance changes in which (a) a hydrophilic residue, for example, seryl or threonyl, is substituted for (or by) a hydrophobic residue, for example, leucyl, isoleucyl, phenylalanyl, valyl or alanyl; (b) a cysteine or proline is substituted for (or by) any other residue; (c) a residue having an electropositive side chain, for example, lysyl, arginyl, or histadyl, is substituted for (or by) an electronegative residue, for example, glutamyl or aspartyl; or (d) a residue having a bulky side chain, for example, phenylalanine, is substituted for (or by) one not having a side chain, for example, glycine.

Promoter: A promoter is an array of nucleic acid control sequences which direct transcription of a nucleic acid. A promoter includes necessary nucleic acid sequences near the start site of transcription. A promoter also optionally includes distal enhancer or repressor elements. A "constitutive promoter" is a promoter that is continuously active and is not subject to regulation by external signals or molecules. In contrast, the activity of an "inducible promoter" is regulated by an external signal or molecule (for example, a transcription factor).

Purified: The term "purified" does not require absolute purity; rather, it is intended as a relative term. Thus, for example, a purified peptide, protein, virus, or other active compound is one that is isolated in whole or in part from naturally associated proteins and other contaminants. In certain embodiments, the term "substantially purified" refers to a peptide, protein, virus or other active compound that has been isolated from a cell, cell culture medium, or other crude preparation and subjected to fractionation to remove various components of the initial preparation, such as proteins, cellular debris, and other components.

Rabies: A viral disease that causes acute encephalitis (inflammation of the brain) in warm-blooded animals. Rabies is zoonotic (transmitted by animals), most commonly by a bite from an infected animal but occasionally by other forms of contact. Rabies is almost frequently fatal if post-exposure prophylaxis is not administered prior to the onset of severe symptoms. Rabies is caused by viruses of the *Lyssavirus* genus.

Rabies virus (RABV or RABV): A member of the Rhabdoviridae family having a non-segmented RNA genome with negative sense polarity. Rabies virus is the prototype of the *Lyssavirus* genus. The rabies virus Evelyn-Rokitnicki-Abelseth (ERA) strain is a strain derived from the Street-Alabama-Dufferin (SAD) strain, first isolated from a rabid dog in Alabama (USA) in 1935. The ERA strain was derived after multiple passages of SAD RABV in mouse brains, baby hamster kidney (BHK) cells, and chicken embryos. The complete genomic sequence of the ERA strain is disclosed in PCT Publication No. WO 2007/047459, and the sequence of the ERA strain recovered by reverse genetics is set forth herein as SEQ ID NO: 1.

Recombinant: A recombinant nucleic acid, protein or virus is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, for example, by genetic engineering techniques. In some embodiments, recombinant rabies virus is generated using reverse genetics, such as the reverse genetics system described in PCT Publication No. WO 2007/047459. In some examples, the recombinant rabies viruses comprise one or more mutations in a viral virulence factors, such as glycoprotein. In other examples, the recombinant rabies viruses comprise a heterologous gene, such as a sequence encoding a glycoprotein from another *lyssavirus* (such as Mokola virus, West Caucasian bat virus or Lagos bat virus).

Reverse genetics: Refers to the process of introducing mutations (such as deletions, insertions or point mutations) into the genome of an organism or virus in order to determine the phenotypic effect of the mutation. For example, introduction of a mutation in a specific viral gene enables one to determine the function of the gene.

Sequence identity: The similarity between two nucleic acid sequences, or two amino acid sequences, is expressed in terms of the similarity between the sequences, otherwise referred to as sequence identity. Sequence identity is frequently measured in terms of percentage identity (or similarity or homology); the higher the percentage, the more similar the two sequences are.

Methods of alignment of sequences for comparison are well known in the art. Various programs and alignment algorithms are described in: Smith and Waterman (*Adv. Appl. Math.,* 2:482, 1981); Needleman and Wunsch (*J. Mol. Biol.,* 48:443, 1970); Pearson and Lipman (*Proc. Natl. Acad. Sci.,* 85:2444, 1988); Higgins and Sharp (*Gene,* 73:237-44, 1988); Higgins and Sharp (*CABIOS,* 5:151-53, 1989); Corpet et al. (*Nuc. Acids Res.,* 16:10881-90, 1988); Huang et al. (*Comp. Appls. Biosci.,* 8:155-65, 1992); and Pearson et al. (*Meth. Mol. Biol.,* 24:307-31, 1994). Altschul et al. (*Nature Genet.,* 6:119-29, 1994) presents a detailed consideration of sequence alignment methods and homology calculations.

The alignment tools ALIGN (Myers and Miller, *CABIOS* 4:11-17, 1989) or LFASTA (Pearson and Lipman, 1988) may be used to perform sequence comparisons (Internet Program© 1996, W. R. Pearson and the University of Virginia, "fasta20u63" version 2.0u63, release date December 1996). ALIGN compares entire sequences against one another, while LFASTA compares regions of local similarity. These alignment tools and their respective tutorials are available on the Internet at the NCSA website. Alternatively, for comparisons of amino acid sequences of greater than about 30 amino acids, the "Blast 2 sequences" function can be employed using the default BLOSUM62 matrix set to default parameters, (gap existence cost of 11, and a per residue gap cost of 1). When aligning short peptides (fewer than around 30 amino acids), the alignment should be performed using the "Blast 2 sequences" function, employing the PAM30 matrix set to default parameters (open gap 9, extension gap 1 penalties). The BLAST sequence comparison system is available, for instance, from the NCBI web site; see also Altschul et al., *J. Mol. Biol.,* 215:403-10, 1990; Gish and States, *Nature Genet.,* 3:266-72, 1993; Madden et al., *Meth. Enzymol.,* 266:131-41, 1996; Altschul et al., *Nucleic Acids Res.,* 25:3389-402, 1997; and Zhang and Madden, *Genome Res.,* 7:649-56, 1997.

Orthologs (equivalent to proteins of other species) of proteins are in some instances characterized by possession of greater than 75% sequence identity counted over the full-length alignment with the amino acid sequence of specific protein using ALIGN set to default parameters. Proteins with even greater similarity to a reference sequence will show increasing percentage identities when assessed by this method, such as at least 80%, at least 85%, at least 90%, at least 92%, at least 95%, or at least 98% sequence identity. In addition, sequence identity can be compared over the full length of one or both binding domains of the disclosed fusion proteins.

When significantly less than the entire sequence is being compared for sequence identity, homologous sequences will typically possess at least 80% sequence identity over short windows of 10-20, and may possess sequence identities of at least 85%, at least 90%, at least 95%, or at least 99% depending on their similarity to the reference sequence. Sequence identity over such short windows can be determined using LFASTA; methods are described at the NCSA website. One of skill in the art will appreciate that these sequence identity ranges are provided for guidance only; it is entirely possible that strongly significant homologs could be obtained that fall outside of the ranges provided. Similar homology concepts apply for nucleic acids as are described for protein. An alternative indication that two nucleic acid molecules are closely related is that the two molecules hybridize to each other under stringent conditions.

Nucleic acid sequences that do not show a high degree of identity may nevertheless encode similar amino acid sequences, due to the degeneracy of the genetic code. It is understood that changes in nucleic acid sequence can be made using this degeneracy to produce multiple nucleic acid sequences that each encode substantially the same protein.

Subject: Living multi-cellular vertebrate organisms, a category that includes both human and non-human mammals.

Therapeutically effective amount: A quantity of a specified agent sufficient to achieve a desired effect in a subject being treated with that agent. For example, this may be the amount of a recombinant rabies virus useful for eliciting an immune response in a subject and/or for preventing infection by rabies virus and other *lyssaviruses*. Ideally, in the context of the present disclosure, a therapeutically effective amount of a recombinant rabies virus is an amount sufficient to increase resistance to, prevent, ameliorate, and/or treat infection caused by one or more *lyssaviruses* in a subject without causing a substantial cytotoxic effect in the subject. The effective amount of a recombinant rabies virus useful for increasing resistance to, preventing, ameliorating, and/or treating infection in a subject will be dependent on, for example, the subject being treated, the manner of administration of the therapeutic composition and other factors. In some embodiments, the recombinant rabies viruses described herein comprise a nucleic acid sequence encoding one or more glycoproteins from a *lyssavirus* other than rabies virus ERA.

Vaccine: A preparation of immunogenic material capable of stimulating an immune response, administered for the prevention, amelioration, or treatment of infectious or other type of disease (such as cancer). The immunogenic material may include attenuated or killed microorganisms (such as attenuated viruses), or antigenic proteins, peptides or DNA derived from them. Vaccines may elicit both prophylactic (preventative) and therapeutic responses. Methods of administration vary according to the vaccine, but may include inoculation, ingestion, inhalation or other forms of administration. Inoculations can be delivered by any of a number of routes, including parenteral, such as intravenous, subcutaneous or intramuscular. Vaccines may be administered with an adjuvant to boost the immune response.

Vector: A nucleic acid molecule that can be introduced into a host cell, thereby producing a transformed host cell. A vector may include nucleic acid sequences that permit it to replicate in a host cell, such as an origin of replication (DNA sequences that participate in initiating DNA synthesis). A vector may also include one or more selectable marker genes and other genetic elements known in the art.

Virus: Microscopic infectious organism that reproduces inside living cells. A virus typically consists essentially of a core of nucleic acid (single- or double-stranded RNA or DNA) surrounded by a protein coat, and in some cases lipid envelope, and has the ability to replicate only inside a living cell. "Viral replication" is the production of additional virus by the occurrence of at least one viral life cycle.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. In case of conflict, the present specification, including explanations of terms, will control. In addition, the materials, methods, and examples are illustrative only and not intended to be limiting.

III. Overview of Several Embodiments

Disclosed herein are recombinant rabies viruses having glycoprotein (G) genes from at least two different *lyssaviruses*. The disclosed viruses can be used as pan-*lyssavirus* vaccines to provide protection against infection by multiple genotypes of *lyssavirus*. Prior to the present disclosure, no vaccines had been described that protect against West Caucasian bat virus and/or *lyssaviruses* of genotypes 2 (Lagos bat virus) and 3 (Mokola virus). Thus, the recombinant rabies viruses described herein represent a significant advance in the development of vaccines for the prevention of rabies.

The recombinant rabies viruses exemplified herein are generating using a previously described reverse genetics system based on the ERA strain of rabies virus (PCT Publication No. WO 2007/047459). However, other reverse genetics systems for rabies virus (see, for example, Ito et al., *J. Virol.* 75(19):9121-9128) could be used to generate recombinant viruses having multiple *lyssavirus* G genes.

Provided herein is a recombinant rabies virus, wherein the genome of the recombinant rabies virus comprises rabies virus nucleoprotein (N), phosphoprotein (P), matrix protein (M), RNA-dependent RNA polymerase (L) and glycoprotein (G) genes and at least one, at least two or at least three different heterologous *lyssavirus* glycoprotein genes, wherein the *lyssavirus* is selected from Lagos bat virus (LBV), Mokola virus (MOKV), Duvenhage virus (DUVV), European bat *lyssavirus*-1 (EBLV-1), European bat *lyssavirus*-2 (EBLV-2), Australian bat *lyssavirus* (ABLV), Aravan virus (ARAV), Khujand virus (KHUV), Irkut virus (IRKV) and West Caucasian bat virus (WCBV). In particular embodiments, the *lyssavirus* is selected from LBV, MOKV and WCBV.

In some embodiments, the recombinant rabies virus comprises two heterologous G genes. In particular examples, the two heterologous G genes are from MOKV and WCBV. In other examples, the two heterologous G genes are from LBV and MOKV. In yet other examples, the two heterologous G genes are from LBV and WCBV.

In some embodiments, the recombinant rabies virus comprises three heterologous G genes. In particular examples, the three heterologous G genes are from LBV, MOKV and WCBV.

In some embodiments in which the recombinant rabies virus comprises a MOKV G gene, the nucleotide sequence of the MOKV G gene is at least 80%, is at least 85%, at least 90%, at least 95%, at least 98% or at least 99% identical to the nucleotide sequence of SEQ ID NO: 47. In some embodiments in which the recombinant rabies virus comprises a WCBV G gene, the nucleotide sequence of the WCBV G gene at least 80%, at least 85%, at least 90%, at least 95%, at least 98% or at least 99% identical to the nucleotide sequence of SEQ ID NO: 49. In some embodiments in which the recombinant rabies virus comprises the LBV G gene, the nucleotide sequence of the LBV G gene is at least 80%, at least 85%, at least 90%, at least 95%, at least 98% or at least 99% identical to the nucleotide sequence of SEQ ID NO: 53.

In some examples, the MOKV G gene comprises the nucleotide sequence of SEQ ID NO: 47, the WCBV G gene comprises the nucleotide sequence of SEQ ID NO: 49 and/or the LBV G gene comprises the nucleotide sequence of SEQ ID NO: 53. In particular examples, the MOKV G gene consists of the nucleotide sequence of SEQ ID NO: 47, the WCBV G gene consists of the nucleotide sequence of SEQ ID NO: 49 and/or the LBV G gene consists of the nucleotide sequence of SEQ ID NO: 53.

The heterologous G genes can be cloned into the rabies virus genome in any suitable location, and in any order, to allow for expression of the heterologous proteins without altering expression of the endogenous rabies virus genes. In some embodiments, heterologous G genes are inserted between the rabies virus P and M genes, between the rabies virus G and L genes and/or between the rabies virus N and P genes. In particular examples, the recombinant rabies virus comprises two heterologous G genes and the heterologous G genes are located between the rabies virus P and M genes and between the G and L genes. In other examples, the recombinant rabies virus comprises three heterologous G genes and the three heterologous G genes are located between the rabies virus N and P genes, between the rabies virus P and M genes and between the rabies virus G and L genes.

Insertion of heterologous genes into the rabies virus genome can be facilitated by synthesizing a transcriptional unit. The transcriptional unit is inserted at the desired gene junction and the heterologous G gene is cloned into the transcriptional unit. In some embodiments, the nucleotide sequence of the transcriptional unit is at least 80%, at least 85%, at least 90%, at least 95%, at least 98% or at least 99% identical to SEQ ID NO: 42. In some examples, the transcriptional unit comprises the nucleotide sequence of SEQ ID NO: 42.

In some embodiments, the genome of the recombinant rabies virus is derived from the rabies virus ERA strain. In some embodiments, the nucleotide sequence of the ERA strain genome comprises a sequence that is at least 90%, at least 95%, at least 98% or at least 99% identical to SEQ ID NO: 1. In particular examples, the nucleotide sequence of the ERA strain genome comprises SEQ ID NO: 1.

In some embodiments, the recombinant rabies virus includes one or more attenuating mutations. In exemplary embodiments, the rabies virus glycoprotein comprises a Glu at amino acid position 333 (SEQ ID NO: 5).

Further provided is a vector comprising a full-length rabies virus antigenomic DNA, wherein the antigenomic DNA comprises rabies virus N, P, M, L and G genes, and wherein the vector further comprises at least one, at least two, or at least three different heterologous *lyssavirus* G genes, wherein the *lyssavirus* is selected from LBV, MOKV, DUVV, EBLV-1, EBLV-2, ABLV, ARAV, KHUV, IRKV and WCBV. In particular embodiments, the *lyssavirus* is selected from LBV, MOKV and WCBV.

In some embodiments, the vector comprises two different heterologous *lyssavirus* G genes. In particular examples, the two heterologous G genes are MOKV and WCBV G genes. In other examples, the two heterologous G genes are MOKV and LBV G genes. In other examples, the two heterologous G genes are LBV and WCBV G genes.

In some embodiments, the vector comprises three heterologous G genes. In particular examples, the three heterologous G genes are from LBV, MOKV and WCBV.

In some embodiments in which the vector comprises a MOKV G gene, the nucleotide sequence of the MOKV G gene is at least 80%, at least 85%, at least 90%, at least 95%, at least 98% or at least 99% identical to the nucleotide sequence of SEQ ID NO: 47. In some embodiments in which the vector comprises a WCBV G gene, the nucleotide sequence of the WCBV G gene is at least 80%, at least 85%, at least 90%, at least 95%, at least 98% or at least 99% identical to the nucleotide sequence of SEQ ID NO: 49. In some embodiments in which the vector comprises the LBV G gene, the nucleotide sequence of the LBV G gene is at least 80%, at least 85%, at least 90%, at least 95%, at least 98% or at least 99% identical to the nucleotide sequence of SEQ ID NO: 53.

In some examples, the MOKV G gene comprises the nucleotide sequence of SEQ ID NO: 47, the WCBV G gene comprises the nucleotide sequence of SEQ ID NO: 49 and/or the LBV G gene comprises the nucleotide sequence of SEQ ID NO: 53. In particular examples, the MOKV G gene consists of the nucleotide sequence of SEQ ID NO: 47, the WCBV G gene consists of the nucleotide sequence of SEQ ID NO: 49 and/or the LBV G gene consists of the nucleotide sequence of SEQ ID NO: 53.

The heterologous G genes can be cloned into the vector encoding the rabies virus genome in any suitable location, and in any order, to allow for expression of the heterologous proteins without altering expression of the endogenous rabies virus genes. In some embodiments, heterologous G genes are inserted between the rabies virus P and M genes, between the rabies virus G and L genes and/or between the rabies virus N and P genes. In particular examples, the recombinant rabies virus comprises two heterologous G genes and the heterologous G genes are located between the rabies virus P and M genes and between the G and L genes. In other examples, the recombinant rabies virus comprises three heterologous G genes and the three heterologous G genes are located between the rabies virus N and P genes, between the rabies virus P and M genes and between the rabies virus G and L genes.

In some embodiments, rabies virus antigenomic DNA inserted in the vector is derived from the rabies virus ERA strain. In some examples, the nucleotide sequence of the ERA strain antigenomic DNA comprises a sequence that is at least 90%, at least 95%, at least 98% or at least 99% identical to SEQ ID NO: 1. In particular examples, the nucleotide sequence of the ERA strain antigenomic DNA comprises SEQ ID NO: 1.

Further provided herein is a cell comprising one or more rabies virus vectors disclosed herein.

Also provided are compositions comprising the recombinant rabies viruses described herein and a pharmaceutically acceptable carrier. In some embodiments, the compositions further comprise an adjuvant.

Also contemplated are compositions comprising multiple recombinant rabies viruses, each encoding at least one heterologous G gene. In some embodiments, the compositions comprise (i) a first recombinant rabies virus, wherein the genome of the first recombinant rabies virus comprises a rabies virus G gene and at least one heterologous *lyssavirus* G gene; and (ii) a second recombinant rabies virus, wherein the genome of the second recombinant rabies virus comprises at least one G gene from a different *lyssavirus* (i.e. a *lyssavirus* G gene that is not in the first recombinant rabies virus); wherein the *lyssavirus* is selected from LBV, MOKV, DUVV, EBLV-1, EBLV-2, ABLV, ARAV, KHUV, IRKV and WCBV. In particular embodiments, the *lyssavirus* is selected from LBV, MOKV and WCBV. In some examples, the second recombinant rabies virus also includes a rabies virus G gene. In some examples, the first and/or second recombinant rabies virus comprises at least two heterologous G genes.

In some examples, the composition comprises (i) a first recombinant rabies virus, wherein the genome of the first recombinant rabies virus comprises a rabies virus G gene and a G gene from MOKV and WCBV; and (ii) a second recombinant rabies virus, wherein the genome of the second recombinant rabies virus comprises a G gene from LBV.

Further provided is a method of eliciting an immune response in a subject against *lyssavirus* by administering to the subject one or more recombinant rabies viruses or compositions disclosed herein. In some embodiments, the immune response in the subject against *lyssavirus* protects the subject against infection by at least three different genotypes of *lyssavirus*. In some embodiments, the immune response in the subject against *lyssavirus* protects the subject against infection by at least four different genotypes of *lyssavirus*. In some embodiments, the subject is a human. In other embodiments, the subject is a non-human animal.

IV. Determinants of Rabies Virus Pathogenicity

Rabies virus (RABV) is a rhabdovirus—a non-segmented RNA virus with negative sense polarity. Within the Rhabdoviridae family, rabies virus is the prototype of the *Lyssavirus* genus. *Lyssaviruses* are composed of two major structural components, a nucleocapsid or ribonucleoprotein (RNP), and an envelope in the form of a bilayer membrane surrounding the RNP core. The infectious component of all rhabdoviruses is the RNP core, which consists of the negative strand RNA genome encapsidated by nucleoprotein (N) in combination with RNA-dependent RNA-polymerase (L) and phosphoprotein (P). The membrane surrounding the RNP contains two proteins, the trans-membrane glycoprotein (G) and the matrix (M) protein, located at the inner site of the membrane. Thus, the viral genome codes for these five proteins: the three proteins in the RNP (N, L and P), the matrix protein (M), and the glycoprotein (G).

The molecular determinants of pathogenicity of various rabies virus strains have not been fully elucidated. RABV pathogenicity was attributed to multigenic events (Yamada et al., *Microbiol. Immunol.* 50:25-32, 2006). For example, some positions in the RABV genome if mutated, affect viral transcription or replication, reducing virulence. Mutations at serine residue 389 of the phosphorylation site in the N gene (Wu et al., *J. Virol.* 76:4153-4161, 2002) or GDN core sequence of the highly conserved C motif in the L gene (Schnell and Conzelmann, *Virol.* 214:522-530, 1995) dramatically reduced RABV transcription and replication.

The G protein, also referred to as spike protein, is involved in cell attachment and membrane fusion of RABV. The amino acid region at position 330 to 340 (referred to as antigenic site III) of the G protein has been identified as important for virulence of certain strains of RABV. Several studies support the concept that the pathogenicity of fixed RABV strains is determined by the presence of arginine or lysine at amino acid residue 333 of the glycoprotein (Dietzschold et al., *Proc. Natl. Acad. Sci. USA* 80: 70-74, 1983; Tuffereau et al., *Virology* 172: 206-212, 1989).

This phenomenon seems to apply at least to fixed rabies viruses such as CVS, ERA, PV, SAD-B19 and HEP-Flury strains (Anilionis et al., *Nature* 294:275-278, 1981; Morimoto et al., *Virology* 173:465-477, 1989). For example, rabies vaccine viruses possessing an amino acid differing from Arg at position 333 of the glycoprotein are described, for instance, in WO 00/32755 (describing RABV mutants in which all three nucleotides in the G protein $Arg_{333}$ codon are altered compared to the parent virus, such that the Arg at position 333 is substituted with another amino acid); European Patent 350398 (describing an avirulent RABV mutant SAG1 derived from the Bern SAD strain of RABV, in which the Arg at position 333 of the glycoprotein has been substituted to Ser); and European patent application 583998 (describing an attenuated RABV mutant, SAG2, in which the Arg at position 333 in the G protein has been substituted by Glu).

Other strains, such as the RC-HL strain, possess an arginine residue at position 333 of the G, but do not cause lethal infection in adult mice (Ito et al., *Microl. Immunol.* 38:479-482, 1994; Ito et al., *J. Virol.* 75:9121-9128, 2001). As such, the entire G may contribute to the virulence of RABV, although the determinants or regions have not been fully elucidated.

The G gene encodes the only protein that induces viral neutralizing antibody. At least three states of RABV glycoprotein are known: the native state (N) being responsible for receptor binding; an active hydrophobic state (A) necessary in the initial step in membrane fusion process (Gaudin, *J. Cell Biol.* 150:601-612, 2000), and a fusion inactive conformation (I). Correct folding and maturation of the G protein play important roles for immune recognition. The three potential glycosylated positions in ERA G extracellular domain occur at $Asn^{37}$, $Asn^{247}$ and $Asn^{319}$ residues (Wojczyk et al., *Glycobiology.* 8: 121-130, 1998). Nonglycosylation of G not only affects conformation, but also inhibits presentation of the protein at the cell surface.

It has been previously demonstrated (see PCT Publication No. WO 2007/047459, which is incorporated herein by reference) that expression of G enhances the anti-RABV immune response. In addition, introduction of an Arg to Glu mutation at amino acid position 333 of RABV ERA glycoprotein results in an attenuated virus (referred to as ERAg3). This attenuated virus is capable of eliciting significant titers of neutralizing antibodies in animals and conferring protection against wild-type virus challenge. Furthermore, as described in PCT Publication No. WO 2007/047459, a recombinant RABV comprising two copies of glycoprotein with the G333 mutation is particularly useful as a vaccine due to its ability to elicit high titers of neutralizing antibodies without morbidity or mortality. In some examples herein, a recombinant rabies virus comprising the G333 mutation in glycoprotein is used as a platform to introduce one or more (such as one, two or three) additional G genes from one or more different genotypes of *lyssavirus*. However, one of ordinary skill in the art will recognize that any one of a number of recombinant rabies viruses can be used to incorporate heterologous sequences using the reverse genetics systems disclosed in PCT Publication No. WO 2007/047459 (or another rabies virus reverse genetics system) as summarized below.

V. Rabies Virus Reverse Genetics System

RNA cannot readily be manipulated directly by molecular biological methods. Traditional RNA virus vaccines are from naturally attenuated isolates, which are difficult to control and provide unpredictable results. Reverse genetics technology makes it possible to manipulate RNA viruses as DNA, which can be mutated, deleted or reconstructed according to deliberate designs. Every gene function can be studied carefully, independently, and in concert, which benefits vaccine development. Reverse genetics involves reverse transcription of the RNA viral genome into cDNA, and cloning into a vector, such as a plasmid. After transfection of host cells, the vector is transcribed into RNA, to be encapsidated by viral structural proteins, which can also be supplied by plasmids. The encapsidated RNA forms a ribonucleoprotein complex, which results in virions that can be recovered.

An efficient reverse genetics system based on the rabies virus ERA strain is described in PCT Publication No. WO 2007/047459, which is incorporated herein by reference. This rabies reverse genetics system is useful for a variety of purposes, including to attenuate ERA virus in a defined manner for vaccine development and to produce ERA virus vectors for expression of heterologous proteins, such as a protein from another *lyssavirus* for the generation of a pan-*lyssavirus* vaccine.

The reverse genetics system disclosed in PCT Publication No. WO 2007/047459 has some or all of the following characteristics, illustrated schematically in FIG. 1A using the exemplary ERA strain antigenomic cDNA.

The rabies virus reverse genetics system is based on a full length transcription plasmid plus a plurality of helper plasmids (e.g., five helper plasmids). The helper plasmids encode the N, P and L proteins, and optionally the G protein, as well as the T7 polymerase. Although the G protein is not necessary for virus rescue, it improves virus recovery efficiency or virus budding when included in transfection.

Transcription involves both cellular RNA dependent RNA polymerase II, which is available in mammalian cells, and T7 RNA polymerase, which is supplied by pNLST7 plasmids. The dual polymerases result in virus recovery efficiency that is both high and stable.

In the transcription plasmid, hammerhead and hepatitis delta virus ribozymes flank a rabies virus (e.g., ERA strain) antigenomic cDNA, enabling the production of authentic 5' and 3' ends of antigenomic viral RNA by transcription. The first ten nucleotides of the hammerhead sequence are designed to be complementary to the first ten nucleotides of the antisense genomic sequence.

Two modified T7 RNA polymerase constructs support virus recovery more efficiently than the wild type T7 RNA polymerase applied previously. One T7 RNA polymerase has been mutated from the first ATG to AT. The second T7 RNA polymerase has an eight amino acid nuclear localization signal (NLS) derived from the SV40 virus large T antigen fused after the first ATG from the parental T7. Addition of the NLS results in the T7 RNA polymerase being present predominantly in the nucleus. Following transfection mechanism of the NLS modified plasmid, the DNA/transfection reagent complex binds to the surface of the cell. Through endocytosis, the complex is taken into the endosome/lysosome, and the DNA is released into the cytosol. In the absence of the NLS, the majority of the transfected plasmids are retained in the cytosol and only a small percentage of the released DNA reaches the nucleus, where it is transcribed into RNA. After protein synthesis, the NLST7 RNA polymerase is transported back to the cell nucleus, and the helper plasmids (with T7/CMV promoters) in the nucleus will be transcribed by both NLST7 and cellular polymerase II. Thus, more mRNAs of the helper plasmids and cRNA of the full-length pTMF or its derivatives are synthesized and result in high efficiency of virus recovery.

Figure 2:
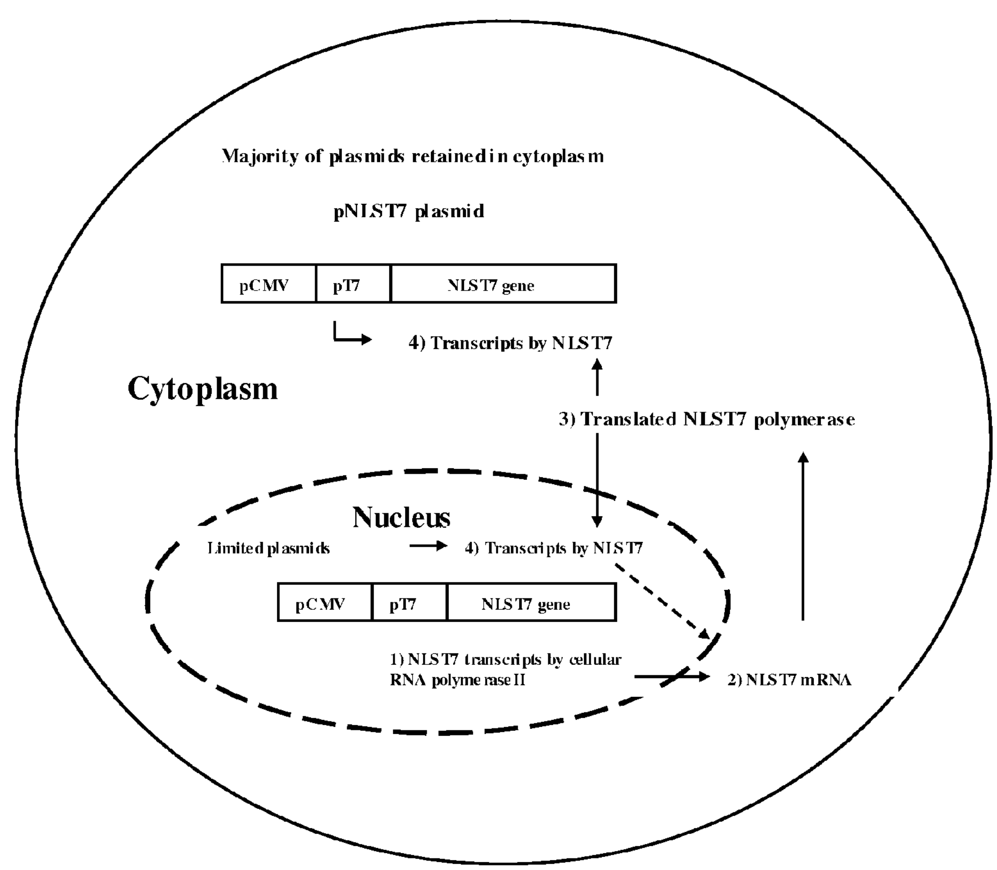
FIG. 2: Schematic illustration of the proposed mechanism of NLST7 RNA polymerase autogene action by pNLST7 plasmids. The DNA-transfection reagent complex is taken into cells by endocytosis. The majority of the DNA released from lysosomes and endosomes is retained in the cell cytoplasm. A limited amount of plasmid is transferred to the nucleus: 1) through a CMV immediate early promoter, the NLST7 gene is transcribed by cellular RNA polymerase II; 2) mature NLST7 mRNA is transported from the nucleus to the cytoplasm for NLST7 RNA polymerase synthesis; 3) newly synthesized NLST7 RNA polymerase is translocated to the nucleus, while a trace amount of NLST7 remains in the cytoplasm; and 4) NLST7 RNA polymerase initiates transcription through a pT7 promoter. By posttranscriptional modifications, additional NLST7 mRNA is produced for protein synthesis, thus increasing virus recovery efficiency.

After the initial expression of NLST7 by the CMV promoter, NLST7 polymerase binds to pT7 for transcription of the NLST7 gene. Through modification of the transcripts in the nucleus, more NLST7 mRNA is synthesized, resulting in greater expression of NLST7 polymerase. The pT7 of the NLST7 polymerase as well as of the full length antigenomic transcription unit is under the control of the NLST7 polymerase, which acts as an “autogene.” The autogene mechanism of NLST7 RNA polymerase is illustrated in FIG. 2. After expression of T7 RNA polymerase in the nucleus, the transfected T7 constructs continue to transcribe full length RNA template for N protein encapsidation and/or L protein binding, enhancing virus recovery efficiency.

The T7 polymerase, and all other plasmids, except the N protein encoding plasmid pTN, are placed under control of both CMV and T7 transcriptional regulatory elements. The N protein encoding nucleic acid is under the control of a T7 promoter and is translated in cap-independent manner based on an IRES (internal ribosome entry site). Cellular RNA polymerase II alone can help the recovery of RABV if all the plasmids were cloned under the control of the CMV promoter. In the ERA reverse genetics system disclosed in PCT Publication No. WO 2007/047459, only pTN is under the control of the T7 promoter and is translated in a cap-independent manner. All other constructs are under control of both CMV and the T7 transcriptional regulatory elements. Typically, in RABV, N synthesis is abundant and the ratio among N, P and L is approximately 50:25:1. To mimic the wild type viral transcription and assembly in RABV reverse genetics, N expression should be the highest. With the aid of NLST7 polymerase and IRES translation mode, N protein is expressed efficiently after plasmid transfection. This reduces competition for transcription with housekeeping genes in host cells, because the T7 transcription initiation signal does not exist in mammalian cells, and results in increased efficiency of T7 transcription.

In addition, as described in PCT Publication No. WO 2007/047459, to enhance production of viral proteins, the helper plasmids can be constructed to incorporate a Kozak sequence that has been optimized for the translation efficiency for each protein encoding sequence. After five days post-transfection in the ERA reverse genetics system, the rescued viruses reliably and repeatably grew to$10^7$ FFU/ml without further amplification.

Recombinant rabies viruses with favorable properties for vaccination can be designed using, for example, the reverse genetics system disclosed in PCT Publication No. WO 2007/047459. Modified strains having mutated glycoproteins are particularly suited for use as immunogenic compositions. This RABV reverse genetics system also enables a rabies virus vector system for foreign (heterologous) gene expression. An extra transcription unit was previously demonstrated to be functional in two different locations after incorporation into the RABV ERA genome. Thus, the RABV reverse genetics system provides a means for introducing heterologous proteins. In some examples, the heterologous protein is a glycoprotein from a *lyssavirus* other than the RABV ERA strain.

VI. Administration and Use of Recombinant Rabies Virus Compositions

The recombinant rabies viruses provided herein comprise at least one heterologous nucleic acid sequence encoding a glycoprotein from a *lyssavirus* other than RABV ERA. The immunogenic compositions provided herein are designed to provide protection to multiple *lyssavirus* genotypes, and in some cases, provide protection against all 11 known *lyssavirus* genotypes. The immunogenic compositions provided herein are contemplated for use with both human and non-human animals.

The immunogenic formulations may be conveniently presented in unit dosage form and prepared using conventional pharmaceutical techniques. Such techniques include the step of bringing into association the active ingredient and the pharmaceutical carrier(s) or excipient(s). In general, the formulations are prepared by uniformly and intimately bringing into association the active ingredient with liquid carriers. Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampoules and vials, and may be stored in a freeze-dried (lyophilized) condition requiring only the addition of a sterile liquid carrier, for example, water for injections, immediately prior to use. Extemporaneous injection solutions and suspensions may be prepared from sterile powders, granules and tablets commonly used by one of ordinary skill in the art.

In certain embodiments, unit dosage formulations are those containing a dose or unit, or an appropriate fraction thereof, of the administered ingredient. It should be understood that in addition to the ingredients particularly mentioned above, formulations encompassed herein may include other agents commonly used by one of ordinary skill in the art.

The compositions provided herein, including those for use as immunogenic compositions, may be administered through different routes, such as oral, including buccal and sublingual, rectal, parenteral, aerosol, nasal, intramuscular, subcutaneous, intradermal, and topical. They may be administered in different forms, including but not limited to solutions, emulsions and suspensions, microspheres, particles, microparticles, nanoparticles, and liposomes. In some embodiments, the immunogenic compositions are administered orally.

The volume of administration will vary depending on the route of administration. Those of ordinary skill in the art will know appropriate volumes for different routes of administration.

Administration can be accomplished by single or multiple doses. The dose administered to a subject in the context of the present disclosure should be sufficient to induce a beneficial therapeutic response over time, such as to prevent *lyssavirus* infection or the development of rabies. The dose required may vary depending on, for example, the age, weight and general health of the subject.

The amount of immunogenic composition in each dose is selected as an amount that induces an immunostimulatory response without significant, adverse side effects. Such amount will vary depending upon which specific composition is employed and how it is administered. Initial doses may range from about 1 μg to about 1 mg, with some embodiments having a range of about 10 μg to about 800 μg, and still other embodiments a range of from about 25 μg to about 500 μg. Following an initial administration of the immunogenic composition, subjects may receive one or several booster administrations, adequately spaced. Booster administrations may range from about 1 μg to about 1 mg, with other embodiments having a range of about 10 μg to about 750 μg, and still others a range of about 50 μg to about 500 μg. Periodic boosters at intervals of 1-5 years, for instance three years, may be desirable to maintain the desired levels of protective immunity. In preferred embodiments, subjects receive a single dose of an immunogenic composition.

Provided herein are pharmaceutical compositions (also referred to as immunogenic or immunostimulatory compositions) which include a therapeutically effective amount of a recombinant RABV alone or in combination with a pharmaceutically acceptable carrier. In some embodiments, the recombinant RABV comprises a heterologous protein, such as glycoprotein from another *lyssavirus* that causes rabies.

Pharmaceutically acceptable carriers include, but are not limited to, saline, buffered saline, dextrose, water, glycerol, ethanol, and combinations thereof. The carrier and composition can be sterile, and the formulation suits the mode of administration. The composition can also contain minor amounts of wetting or emulsifying agents, or pH buffering agents. The composition can be a liquid solution, suspension, emulsion, tablet, pill, capsule, sustained release formulation, or powder. The composition can be formulated as a suppository, with traditional binders and carriers such as triglycerides. Oral formulations can include standard carriers such as pharmaceutical grades of mannitol, lactose, starch, magnesium stearate, sodium saccharine, cellulose, and magnesium carbonate. Any of the common pharmaceutical carriers, such as sterile saline solution or sesame oil, can be used. The medium can also contain conventional pharmaceutical adjunct materials such as, for example, pharmaceutically acceptable salts to adjust the osmotic pressure, buffers, preservatives and the like. Other media that can be used with the compositions and methods provided herein are normal saline and sesame oil.

The recombinant RABVs described herein can be administered alone or in combination with other therapeutic agents to enhance antigenicity. For example, the recombinant viruses can be administered with an adjuvant, such as Freund incomplete adjuvant or Freund's complete adjuvant.

Optionally, one or more cytokines, such as IL-2, IL-6, IL-12, RANTES, GM-CSF, TNF-α, or IFN-γ, one or more growth factors, such as GM-CSF or G-CSF; one or more molecules such as OX-40L or 41 BBL, or combinations of these molecules, can be used as biological adjuvants (see, for example, Salgaller et al., 1998, *J. Surg. Oncol.* 68(2):122-38; Lotze et al., 2000, *Cancer J. Sci. Am.* 6(Suppl 1):S61-6; Cao et al., 1998, *Stem Cells* 16(Suppl 1):251-60; Kuiper et al., 2000, *Adv. Exp. Med. Biol.* 465:381-90). These molecules can be administered systemically (or locally) to the host.

A number of means for inducing cellular responses, both in vitro and in vivo, are known. Lipids have been identified as agents capable of assisting in priming CTL in vivo against various antigens. For example, as described in U.S. Pat. No. 5,662,907, palmitic acid residues can be attached to the alpha and epsilon amino groups of a lysine residue and then linked (for example, via one or more linking residues, such as glycine, glycine-glycine, serine, serine-serine, or the like) to an immunogenic peptide. The lipidated peptide can then be injected directly in a micellar form, incorporated in a liposome, or emulsified in an adjuvant. As another example, *E. coli* lipoproteins, such as tripalmitoyl-S-glycerylcysteinly-seryl-serine can be used to prime tumor specific CTL when covalently attached to an appropriate peptide (see, Deres et al., *Nature* 342:561, 1989). Further, as the induction of neutralizing antibodies can also be primed with the same molecule conjugated to a peptide which displays an appropriate epitope, two compositions can be combined to elicit both humoral and cell-mediated responses where that is deemed desirable.

The following examples are provided to illustrate certain particular features and/or embodiments. These examples should not be construed to limit the disclosure to the particular features or embodiments described.

EXAMPLES

Example 1

Construction of Plasmids for a Reverse Genetics System for Rabies Virus

Figure 1B:
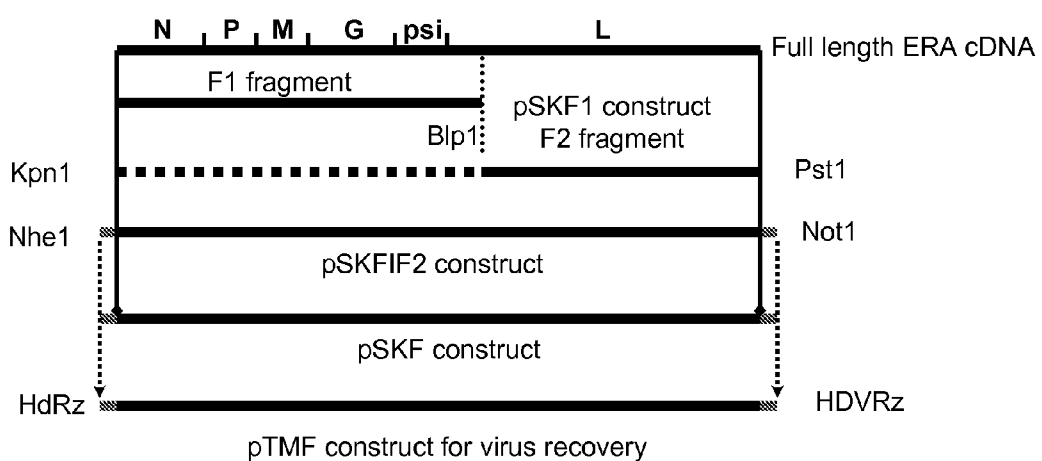
FIG. 1B: Schematic diagram of the construction of the full-length ERA rabies virus genomic cDNA plasmid pTMF. RT-PCR products F1 and F2 fragments, and restriction enzyme recognition sites (Nhe1, Kpn1, Blp1, Pst1 and Not1) are shown. RdRz-hammerhead and HDVRz-hepatitis delta virus ribozymes are indicated. The diamond symbols indicate that Kpn1 or Pst1 sites were deleted, and the vertical arrows indicate that Nhe1 or Not1 sites were left intact.

This example describes the design and development of a reverse genetics system for rabies virus. Rabies virus strain ERA was obtained from the ATCC and was prepared as described (Wu et al., *J. Virol.* 76, 4153-4161, 2002). To obtain virus genome full-length virus cDNA, BSR cells (a clone of baby hamster kidney, BHK, cells) were infected with ERA strain virus and grown in Dulbecco's minimal essential medium supplemented with 10% of fetal bovine serum. Supernatants were recovered and subjected to centrifugation at 22,000 g for 1 hour. The virus pellets were collected for viral genomic RNA purification by use of a RNA virus extraction kit purchased from Qiagen (Valencia, Calif.) according to the manufacturer's instructions. The integrity of viral genomic RNA was confirmed by gel electrophoresis. Viral genomic cDNA was transcribed with the first-strand cDNA synthesis kit from Life Technologies (Carlsbad, Calif.). The reverse transcription (RT) reaction mixture was applied to amplification by the polymerase chain reaction (PCR) for the synthesis of full-length viral genomic cDNA, N, P, G and L genes, respectively. For assembling the full-length virus genomic cDNA, a pTMF plasmid was constructed in four sequential steps as illustrated schematically in FIG. 1B. Superscript III reverse transcriptase and proof reading platinum pfx polymerase (Life Technologies, Carlsbad, Calif.) were applied for cDNA transcript synthesis and consecutive PCR amplifications. For reverse transcription reactions, 1 μg of purified genomic RNA was used in the RT reaction mix and incubated at 50° C. for 80 min, followed by heating at 85° C. for 5 minutes to inactivate Superscript III. After the RT reaction, 1 unit of RNaseH was added to digest template RNA in the cDNA-RNA hybrids.

To generate full-length virus genomic cDNA, two overlapping fragments were amplified by RT-PCR as follows: Fragment 1 (F1) was RT-PCR amplified with primers: Le5-Kpn (CCGGGTACCACGCTTAAC AACCAGATCAAAGA; SEQ ID NO: 8, Kpn1 recognition site shown in bold) and Le3-Blp (TAGGTCGCTTGCTAAGCACTCCTGGTAGGAC; SEQ ID NO: 9, Blp1 recognition site shown in bold). Fragment 2 (F2) was RT-PCR amplified with primers: Tr5-Blp (GTCCTACCAGGAGTGCTTAGCAAGCGACCTA; SEQ ID NO: 10, Blp1 recognition site shown in bold) and Tr3-Pst (AAAACTGCAGACGCTTAACAAATAAACAACAAAA; SEQ ID NO: 11, Pst1 recognition site shown in bold). After successful synthesis of the above two fragments, F1 digested by Kpn1 and Blp1 restriction enzymes was subjected to gel purification and cloned to pBluescriptIISK(+) phagemid (Stratagene, La Jolla, Calif.) to form the pSKF1 plasmid. The gel purified F2 fragment, cut by Blp1 and Pst1 was consecutively cloned to the pSKF1 plasmid to form the full-length viral antigenomic cDNA. Hammerhead ribozyme (oligo1, CAAGGCTAGCTGTTAAGCGTCTGATGAGTCCGTGAGGACGAAACTATA GGAAAGGAATTCCTATAGTCGGTACCACGCT; SEQ ID NO: 12, Nhe1 and Kpn1 recognition sites shown in bold; oligo2, AGCGTGGTACCGACTATAGGAATTCCTTTCCTATAGTTTCGTCCTCACG GACTCATCAGACGCTTAACAGCTAGCCTTG; SEQ ID NO: 13, Kpn1 and Nhe1 recognition sites shown in bold) was synthesized containing a Nhe1 recognition site at the 5' end and a Kpn1 site at the 3' end. This was fused ahead of the 5' end of the F1 fragment. A hepatitis delta virus ribozyme (oligo3, GACCTGCAGGGGTCGGCATGGCATCTCCACCTCCTCGCGGTCCGACCTG GGCATCCGAAGGAGGACGCACGTCCACTCGGATGGCTAAGGGAGGGCG CGGCCGCACTC; SEQ ID NO: 14, Pst1 and Not1 recognition sites shown in bold; oligo4, GAGTGCGGCCGCGCCCTCCCTTAGCCATCCGAGTGGACGTGCGTCCTCC TTCGGATGCCCAGGTCGGACCGCGAGGAGGTGGAGATGCCATGCCGAC CCCTGCAGGTC; SEQ ID NO: 15, Not1 and Pst1 recognition sites shown in bold) (Symons, *Annu. Rev. Biochem.* 61: 641-671, 1992) was synthesized, having a Pst1 site at its 5' end and a Not1 site at its 3' end, and was fused to the 3' end of the F2 fragment. The connective Kpn1 recognition site, between the hammerhead ribozyme and the F1 fragment, and the Pst1 site between the F2 fragment and the hepatitis delta virus ribozyme, were deleted by site-directed mutagenesis. The full-length viral antigenomic cDNA was sandwiched by the hammerhead and hepatitis delta virus ribozymes. This was removed and cloned to the pBluescriptIISK(+) phagemid to make a pSKF construct. The full viral antigenomic cDNA with two ribozymes was fused downstream of the T7 transcription initiation site under control of the CMV immediate-early promoter in pcDNA3.1/Neo (+) plasmid (Life Technologies, Carlsbad, Calif.). This last step finished the construction of the pTMF plasmid.

The wild type ERA viral genome includes a polyA tract of eight residues (poly$A_8$) in the intergenic region between the G and Psi regions. To distinguish the rescued ERA (rERA) virus from the parental strain, a stretch of seven A (poly$A_7$) was introduced to the pTMF construct by deletion of one A instead of the original poly$A_8$. After rERA virus was recovered, RT-PCR was performed and subsequent sequence data confirmed the existence of the introduced poly $A_7$ sequence marker.

pTN plasmid: The N gene was amplified by RT-PCR with primers (5N: ACCACC *ATG* GATGCCGACAAGATTG; SEQ ID NO: 16, Nco1 recognition site and start codon shown in bold; and 3N: GGCCCATGG *TTA* TGAGTCACTCGAATATGTCTT; SEQ ID NO: 17, Nco1 recognition site and stop codon shown in bold) and cloned to the pCITE-2a(+) (Cap-Independent Translation Enhancer) plasmid (Novagen, Madison Wis.).

pMP plasmid: the P gene was amplified by RT-PCR with primers (5P: TTGGTACCACC *ATG* AGCAAGATCTTTGTCAATC; SEQ ID NO: 18, Kpn1 recognition site and start codon shown in bold; and 3P: GGAGAGGAATTC *TTA* GCAAGATGTATAGCGATTC; SEQ ID NO: 19, EcoR1 recognition site and stop codon shown in bold) and cloned to the pcDNA3.1/Neo (+) plasmid.

pMG plasmid: the G gene was amplified by RT-PCR with primers (5G: TTGGTACCACC *ATG* GTTCCTCAGGCTCTCCTG; SEQ ID NO: 20, Kpn1 recognition site and start codon shown in bold; and 3G: AAAACTGCAG *TCA* CAGTCTGGTCTCACCCCCAC; SEQ ID NO: 21, Pst1 recognition site and stop codon shown in bold) and cloned to the pcDNA3.1/Neo (+) plasmid.

pML plasmid: the L gene was amplified by RT-PCR with primers (5L: ACCGCTAGCACCACC *ATG* CTCGATCCTGGAGAGGTC; SEQ ID NO: 22, Nhe1 recognition site and start codon shown in bold; and 3L: AAAACTGCAG *TCA* CAGGCAACTGTAGTCTAGTAG; SEQ ID NO: 23, Pst1 recognition site and stop codon shown in bold) and cloned to the pcDNA3.1/Neo (+) plasmid.

pT7 plasmid: genomic DNA from bacteria BL-21 (Novagene, Madison, Wis.) was extracted with the Dneasy Tissue Kit (Qiagen, Valencia, Calif.) according to the manufacturer's instructions. The T7 RNA polymerase gene was amplified from the purified genomic DNA by PCR with primers (5T7: TCGCTAGCACCACC *ATG* AACACGATTAACATCGCTAAG; SEQ ID NO: 24, Nhe1 recognition site and start codon shown in bold; and 3T7: GATGAATTC *TTA* CGCGAACGCGAAGTCCGACTC; SEQ ID NO: 25, EcoR1 recognition site and stop codon shown in bold) and cloned to the pcDNA3.1/Neo (+) plasmid.

pNLST7 plasmid: an eight amino acid nuclear location signal (NLS), derived from SV40 large T antigen, was added to the N terminus of the T7 RNA polymerase by PCR amplification, using the pT7 plasmid as the template, with primers (5T7NLS: TCGCTAGCCACCATGCCAAAAAAGAAGAGAAAGGTAGAAAACACGAT TAACATCGCTAAGAAC; SEQ ID NO: 26, NLS shown in bold and 3T7 primer). The amplified fragment was designated NLST7, and was cloned to pcDNA3.1/Neo (+) to form the pNLST7 construct.

pGFP plasmid: Monster Green Fluorescent Protein(GFP) plasmid phMGFP was purchased from Promega (Madison, Wis.). The GFP gene was amplified by PCR with primers (GFP5: AAAACTGCAGGCCACC *ATG* GGCGTGATCAAG; SEQ ID NO: 27, Pst1 recognition site and start codon shown in bold; and GFP3: CCGCTCGGTACCTA *TTA* GCCGGCCTGGCGGG; SEQ ID NO: 28, Kpn1 recognition site and stop codon shown in bold) and cloned to the pcDNA3.1/Neo (+) plasmid.

All plasmid constructs were sequenced at least three times to confirm the absence of unexpected mutations or deletions after cloning, site-directed mutagenesis, or gene deletion. Additionally, the presence of a marker sequence consisting of a polyA tract having seven adenosine residues rather than the eight residues observed in the wild type ERA genome between the glycoprotein and Psi region was confirmed.

Example 2

Figure 3:
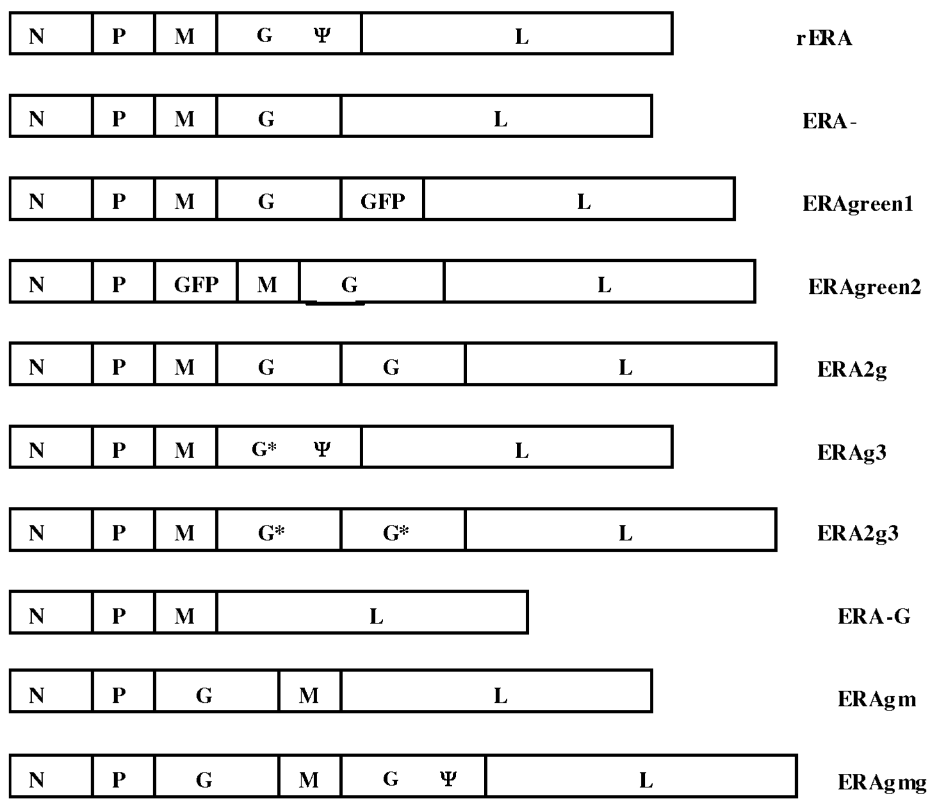
FIG. 3: Schematic diagram of ten derivative ERA virus genomes. The size of each gene is not drawn to scale. Symbol "*" denotes mutations of G at amino acid residue 333 (referred to herein as G333) and "Ψ" indicates the Psi-region.

Defined Modification of Rabies Virus Evelyn-Rokitnicki-Abelseth (ERA) Strain In addition to the parental ERA virus strain described above, derivative virus strains were developed using the reverse genetics system disclosed herein. Several exemplary modified viruses were produced, namely ERA-(deletion of the whole psi-region), ERAgreen1 (green florescent protein gene inserted in ERA viral genome psi region), ERAgreen2 (green florescent protein gene inserted in phosphoprotein and matrix protein intergenic region), ERA2g (containing an extra copy of glycoprotein in the psi-region), ERAg3 (with a mutation at amino acid 333 in glycoprotein), ERA2g3 (with an extra copy of mutated glycoprotein at Aa333 in psi-region), ERA-G (with glycoprotein deleted) ERAgm (M and G genes switched in the genome), and ERAgmg (two copies of G in the rearranged ERAgm construct) These derivatives are illustrated schematically in FIG. 3. By optimizing the growth conditions as described, all of the rescued viruses can be obtained at virus titers of $10^9$ to $10^{10}$ ffu/ml in both tissue culture flasks and bioreactors.

Gene Deletion and Site-Directed Mutagenesis in the Reverse Genetics System

Deletion of the Psi Region of the Rabies Virus ERA Genome

The complete Psi-region of the rabies virus ERA genome was deleted as follows: 3'Δψ fragment was amplified using pTMF as template by PCR with primers (5Δψ: CCCTCTGCAGTTTGGTACCGTCGAGAAAAAAACATTAGATCAGAAG; SEQ ID NO: 29, Pst1 and Kpn1 recognition sites shown in bold; and Le3-Blp primer) and was cloned to pCR-BluntII-TOPO vector (Life Technologies, Carlsbad, Calif.) for the construction of pPΔ5ψ plasmid. The 5'Δψ fragment was amplified using the same template by PCR with primers (SnaB5: ATGAACTTTCTACGTAAGATAGTG; SEQ ID NO: 30, SnaB1 recognition site shown in bold; and 3Δψ: CAAACTGCAGAGGGGTGTTAGTTTTTTTCAAAAAGAACCCCCCAAG; SEQ ID NO: 31, Pst1 recognition site shown in bold) was successively cloned to the above pPΔ5ψ plasmid to finish the construction of the pPΔψ plasmid. The fragment recovered by SnaB1 and Pst1 restriction enzyme digestion from the pPΔψ plasmid substituted the counterpart in the pSKF construct to make the pSKFΔψ plasmid. The whole DNA fragment containing the ERA genomic cDNA, digested by Nhe1 and Not1 from pSKFΔψ plasmid, was re-cloned to the pcDNA3.1/Neo (+) plasmid to finalize the construction of pTMFΔψ. For verification of the rescued strain lacking Psi, designated Era-, primers covering the Psi-region were applied in RT-PCR with total RNA from ERA-infected BSR cells. A 400 bp fragment corresponding to the Psi region was amplified only from rERA virus, but not from ERA. Sequence data verified the complete deletion of the Psi-region.

Deletion of the Glycoprotein Gene in the Rabies Virus ERA Genome:

The 5'gΔψ fragment was amplified using pSKF as template by PCR with primers (SnaB5 primer, and 3Δg: CAAACTGCAGAGGGGTGTTAGTTTTTTTCACATCCAAGAGGATC; SEQ ID NO: 32). After digestion by SnaB1 and Pst1 restriction enzymes, this recovered fragment was cloned to replace its counterpart in the pSKFΔψ construct. The 3'gΔψ fragment was amplified using the same template by PCR with primers (5Δg: CCTCTGCAGTTTGGTACCTTGAAAAAAACCTGGGTTCAATAG; SEQ ID NO: 33, and Le3-Blp primer), and was consecutively cloned to the modified pSKFΔψ, to replace its counterpart. The final fragment, recovered by SnaB1 and Blp1 restriction enzymes cut from this pSKFΔψ without the G gene, was re-cloned to pcDNA3.1/Neo (+) plasmid to form the pTMFΔg construct for virus recovery.

Glycoprotein Gene Site-Directed Mutagenesis:

Site directed mutagenesis to introduce a three nucleotide change from AGA to GAG at amino acid position 333 of the glycoprotein was performed as previously described (Wu et al., *J. Virol.* 76: 4153-4161, 2002). The primers in the mutagenesis reaction were M5G primer: CTCACTACAAGTCAGTCGAGACTTGGAATGAGATC (SEQ ID NO: 34, the three mutated nucleotides shown in bold) and M3G primer: GACTGACTTTGAGTGAGCATCGGCTTCCATCAAGG (SEQ ID NO: 35). For the recovered strain (ERAg3), three nucleotide changes from AGA to GAG at amino acid position 333 (aa333) were confirmed by sequencing after RT-PCR with primers 5G and 3G. After confirmation by DNA sequencing, the mutated G was cloned back to the pTMF plasmid to make the pTMFg3 construct for virus recovery. The glycoprotein encoded by this mutated G gene is represented by SEQ ID NO: 7.

Incorporation of an Exogenous ORF into ERA Rabies Virus Genome

To express exogenous ORFs in RABV, an extra transcription unit with Pst1 and Kpn1 recognition sites were created and incorporated at the Psi or P-M gene intergenic regions, respectively. In brief, for creation of an extra transcription unit at the Psi-region, the same steps were followed, except for the 5'Δψ fragment amplification step, the 3Δψ primer was changed to 3Δψcis: CCAAACTGCAGCGAAAGGAGGGGTGTTAGTTTTTTTCATGATGAACCCC CCAAGGGGAGG (SEQ ID NO: 36). The final construct without the Psi-region, but with an extra transcription unit, was designated as pMTFΔψcis. The GFP, ERA G, or mutated G at amino acid residues 333 were cloned to this transcriptional unit to form pMTFgfp1, pMTF2g, pMTFg3, pMTF2g3 constructs, respectively, for virus rescue.

To incorporate an extra transcription unit to the P-M intergenic region, the cisp5 fragment was amplified using pMTF as template with primers cis55: GACTCACTATAGGGAGACCCAAGCTGGCTAGCTGTTAAG (SEQ ID NO: 37), cis53: CCAAACTGCAGCGAAAGGAGGGGTGTTAGTTTTTTTCATGTTGACTTTA GGACATCTCGG (SEQ ID NO: 38), and was cloned in substitution of its counterpart in the pMTF plasmid. The cisp3 fragment was amplified and cloned in a similar way with primers cis35: CCTTTCGCTGCAGTTTGGTACCGTCGAGAAAAAAACAGGCAACACCACT GATAAAATGAAC (SEQ ID NO: 39) and cis33: CCTCCCCTTCAAGAGGGCCCCTGGAATCAG (SEQ ID NO: 40). After assembling the cisp5 and cisp3 fragments together, the final construct was designated as pMTFcisp, for accepting ORFs. The recombinant construct containing the GFP gene was named pTMFgfp2 for virus recovery.

To produce an ERA derivative, designated ERAgm, in which the glycoprotein encoding sequence was reversed in order with the matrix protein encoding sequence, the glycoprotein gene was deleted as described above. The G gene (amplified as disclosed above) was then inserted between P and M genes, yielding a rabies virus genome in the order of N-P-G-M-L. Similarly, the same strategy was applied to produce the ERAg3m derivative, in which the glycoprotein has a triple nucleotide mutation at 333 amino acid residue (from AGA to GAG) by substituting the G gene produced by site directed mutagenesis as described above. To produce the ERAgmg construct, an extra copy of glycoprotein gene was inserted between P and M genes, and made the rabies virus genome in the order of N-P-G-M-G-L.

An extra transcription unit was modified and incorporated into two different regions of the ERA genome, namely psi-region and P-M intergenic region. When heterologous ORFs are incorporated into these transcription units, designated trans 1 and trans 2, respectively, efficient production of the encoded product results. Sequence of the transcription unit is:

```
    (SEQ ID NO: 41, Pst1 and Kpn1 were underlined)
CTAACACCCCTCCTTTCGCTGCAGTTTGGTACCGTCGAGAAAAAAA.
```

Example 3

Recovery of Parental and Derivative Viruses

This example describes the recovery of parental ERA virus and exemplary derivatives using the reverse genetics system disclosed herein. BSR cells were transfected at near 80% confluence in six-well-plates with viral full length transcription plasmid pTMF (pTMFAΔψ, pTMFg3, pTMF2g, pTMF2g3, pTMFgfp1, pTMFgfp2, pTMFΔg, pTMFgm, or pTMFgmg, respectively) at 3 μg/well, together with five helper plasmids: pTN (1 μg/well), pMP (0.5 μg/well), pML (0.5 μg/well), pMG (0.5 μg/well) and pNLST7 (1 μg/well) by TransIT-LT1 reagent (Mirus, Madison, Wis.) following the protocol recommended by the manufacturer. Four days after transfection, 1 ml of fresh BSR cell suspension (about $5\times10^5$ cells) was added to each well. Cells were incubated at 37° C., 5% $CO_2$ for 3 days. Cell supernatants were collected for virus titration.

To titrate the recovered virus, monolayers of BSR cells in LAB-TEK eight-well-plates (Naperville, Ill.) were infected with serial 10-fold dilutions of virus supernatant and incubated at 37° C., 0.5% $CO_2$ for 48 h. Cells were fixed in 80% chilled acetone at room temperature for 1 h and stained with FITC-labeled anti-rabies virus N monoclonal antibody at 37° C. for 30 minutes. After three rinses of the plates with PBS, stained foci were counted using direct fluorescent microscopy. Details for direct RABV fluorescent assay (DFA) can be found on the World Wide Web at cdc.gov/ncidod/dvrd/rabies/professional/publications/DFA-diagnosis/DFA_protocol.htm.

All of the viruses except ERA-G were recovered at high titer from cultured BSR cells as indicated in Table 1. Surprisingly, rearrangement and switching of the G gene with the M gene did not hinder recovery of recombinant derivative ERA virus. Rearrangement of the G gene in the RABV genomes was previously not believed feasible due to cell death from overexpression of G protein (Faber et al., *J. Virol.* 76:3374-3381, 2002). However, these results demonstrate that rearrangement is possible in the ERA strain. Accordingly, it is likely that RABV gene shuffling is possible not only for the G gene, but also for other genes as well.

The ERA-G (without G) virus was recovered after plasmid transfection following the same procedure as for the other viral constructs rescue, but virus foci were very limited and restrained in local areas after the first round of transfection. The rescued virus was not capable of spreading further to the nearby healthy BSR cells even after one week of incubation at 37° C., 5% $CO_2$. Infection of normal BSR cells with the above transfection supernatants presented single cell staining in the DFA test, which suggested the recovered virus was incapable of spread. The ERA-G virus was amplified using a BHK cell line that constitutively expresses ERA G (PCT Publication No. WO 2007/047459). By indirect fluorescent assay screening, a pool of BHK cells expressing G were selected and maintained for amplification of ERA-G virus. With the aid of the BHK-G cell line, ERA-G virus grew to $10^7$ ffu/ml. Total RNA from ERA-G virus-infected BHK-G cells was extracted for Northern blot analysis with a G gene probe. The G gene was absent in the viral genomic RNA, however G mRNA was detected, which came from infected supportive BHK-G cells. In purified ERA-G viral genomic RNA, no hybridization signal was detected by G probe, indicating the deletion of the G gene in the ERA genome.

Example 4

Growth of Rescued ERA Virus and its Derivatives to High Titer in a Bioreactor In oral vaccine development, high virus titer is typically required to elicit reliable immunity after administration. This example demonstrates that the ERA virus and derivatives can be grown to high titer in a bioreactor at volumes applicable to commercial scale-up. All 10 rescued ERA viruses were amplified in a bioreactor, CELLine AD1000 (IBS Integra Bioscience, Chur, Switherland) to titers ranging from $10^7$ to $10^{10}$ ffu/ml. In brief, BSR cells were transfected with the exemplary antigenome transcription vectors and helper vectors, as described above. Cells were inoculated at a multiplicity of infection of 1 virion per cell, at a concentration of $10^6$ cells/ml in one tenth the bioreactor vessel volume. Transfected cells were grown at 37° C., 5% $CO_2$ in DMEM supplemented with 10% fetal bovine serum. The supernatant was harvested every three to five days for between two and three harvests. The deficient ERA-G grew less well compared with other viruses, with only $10^8$ ffu/ml for the ERA-G (Table 1).

TABLE 1

Full-length plasmid constructs and corresponding rescued viruses

| Plasmid constructs | Rescued viruses | Titers ffu/ml from cultured cells | Titers ffu/ml in bioreactors |
|---|---|---|---|
| pTMF | rERA | $5 \times 10^7$ | $3 \times 10^{10}$ |
| pTMFΔψ | ERA- | $6.3 \times 10^7$ | $3.2 \times 10^{10}$ |
| pTMFg3 | ERAg3 | $3 \times 10^6$ | $1.8 \times 10^9$ |
| pTMFgfp1 | ERAgreen1 | $3.5 \times 10^6$ | $5.6 \times 10^9$ |
| pTMFgfp2 | ERAgreen2 | $2 \times 10^7$ | $6.2 \times 10^9$ |
| pTMF2g | ERA2g | $1.6 \times 10^6$ | $3.9 \times 10^9$ |
| pTMF2g3 | ERA2g3 | $8 \times 10^7$ | $4.6 \times 10^9$ |
| pTMFΔg | ERA-G | $1.2 \times 10^2$ | $1.5 \times 10^7$ |
| pTMFgm | ERAgm | $5.31 \times 10^6$ | $1.9 \times 10^9$ |
| pTMFgmg | ERAgmg | $3.1 \times 10^6$ | 1.2 × 109 |

Example 5

Expression of Exogenous Proteins from Extra Transcriptional Units in Rabies Virus This example demonstrates the expression of recombinant proteins from a heterologous ORF inserted into a rabies virus vector. In this example, the ERA virus vector is used as a prototype rabies virus vector. To construct ERA virus as a vector for accepting ORFs, a conservative RABV transcriptional unit between the N and P genes was modified and introduced into the ERA genome at two different locations: 1) at the psi region (trans 1), and 2) at the P-M intergenic region (trans 2). The transcriptional unit was designed to possess two unique restriction enzyme recognition sites to facilitate introduction of heterologous polynucleotide sequences (TTTTTTTGATTGTGGGGAGGAAAGC-GACGTCAAACCATGGCAGCTCTTT TTTT; SEQ ID NO: 42, Pst1 and Kpn1 sites shown in bold).

In a first example, the GFP gene was cloned into this unit for virus recovery, since GFP expression could be observed directly under a UV microscope when the transfected BSR cells were still incubating. Expression of the GFP protein was directly visible by fluorescent microscopy with an excitation filter of 470±20 nm. The ERAgreen2 (GFP gene inserted after P gene in RABV genome-trans 2)-infected cells showed clear green foci after three days of plasmid transfection, while ERAgreen1 (GFP gene inserted after G gene in the "traditional" Ψ region-trans 1) did not present obvious green foci until five days post-transfection. The introduced transcriptional unit was functional in the RABV genome at both locations, although expression and accumulation was apparent more rapidly when GFP was expressed from trans 2. Thus, these results also indicate that the level of expression from a heterologous ORF can be modulated by selecting the transcription unit into which the ORF is cloned.

In other examples, 1) an additional copy of ERA G; or 2) an additional copy of ERA G with an amino acid substitution at position 333, was incorporated into the ERA viral genome. The successfully rescued viruses were named ERA2g and ERA2g3, respectively. Since quantitation of viral G expression was not practical, the relative increase in expression levels of G in ERA2g and ERA2g3-infected cells was confirmed by Northern-blot with a G probe. In brief, the ERA G gene probe was labeled using the Dig DNA Labeling Kit (Roche, Indianapolis, Ind.) and imaged with Dig Nucleic Acid Detection Kit (Roche, Indianapolis, Ind.) and was measured by density spectrophotometry. The tandem linked G genes in the recovered viruses were also confirmed by RT-PCR with 5G and 3G primers. A predominant band indicating a single G copy was observed at 1.5 kb. In addition, a second weaker band was observed at approximately 3.0 kb indicative of the two Gs in a tandem arrangement.

These results demonstrate that introduction of transcription units into the ERA genome can be used to express diverse heterologous proteins from introduced ORFs. Furthermore, expression of the protein encoded by the heterologous ORF is modulated by the position into which the ORF is inserted. Thus, ERA virus is a widely adaptable vector for the expression of recombinant proteins.

Example 6

Figure 4:
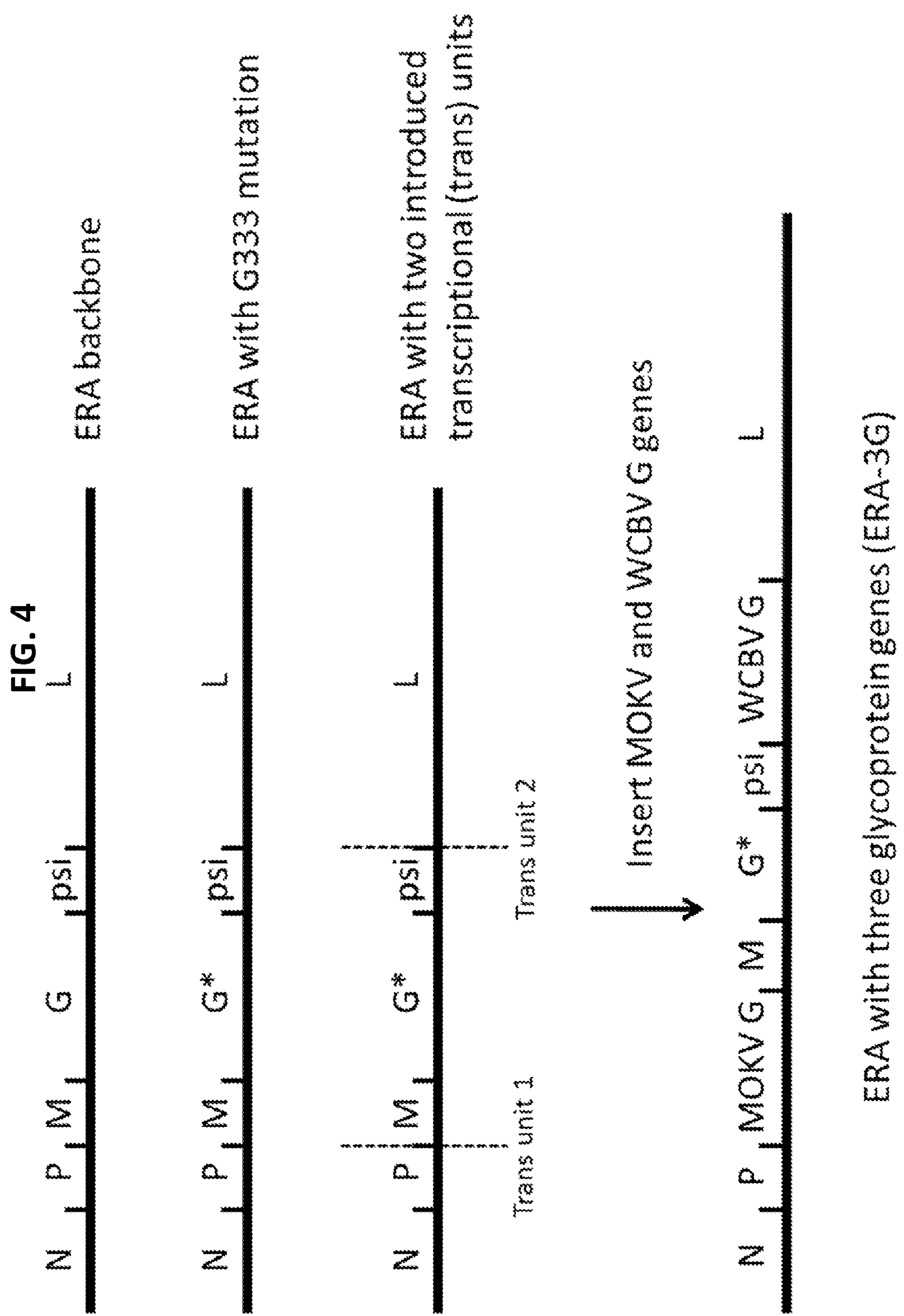
FIG. 4: Schematic of the construction of ERA-3G. The G333 mutation is introduced into the ERA backbone and two transcriptional (trans) units are added. The transcriptional units are introduced between the P and M genes and between the G and L genes. The MOKV and WCBV G genes are cloned into the transcriptional units to form a recombinant ERA rabies virus with three glycoprotein genes (ERA-3G).

Construction and Characterization of Recombinant Rabies Virus with Three Glycoprotein Genes This example describes the generation and characterization of a recombinant ERA strain rabies virus encoding three different glycoprotein genes. The recombinant virus, referred to as ERA-3G, comprises rabies virus glycoprotein, Mokola virus (MOKV) glycoprotein and West Caucasian bat virus (WCBV) glycoprotein. The cloning strategy for ERA-3G is shown in FIG. 4. The rabies virus reverse genetics system used to generate this virus in described in the Examples above. ERA-3G includes the attenuating mutation in the glycoprotein gene that results in an arginine to glutamic acid change at amino acid residue 433 of the protein (SEQ ID NO: 5).

The G genes from MOKV and WCBV were cloned into the ERA backbone by RT-PCR using viral genomic RNA as template from virus-infected cells. The following primers were used for amplification of the glycoprotein genes:

```
                                        (SEQ ID NO: 43)
MokolaG5-CGACTGCAGATGAATATACCTTGCTTTGTTGTGATTC

                                        (SEQ ID NO: 44)
MokolaG3-CGTGGTACCTCATGTACCTGGAAGCCCTTTATAGGACTC

                                        (SEQ ID NO: 45)
WCBVG5-CATCTGCTAGCAATGGCTTCCTACTTTGCGTTG

                                        (SEQ ID NO: 46)
WCBVG3-TTCAATGGTACCTTATTGGGCAGTTTGTCCCTT
```

The amplified G genes for MOKV (SEQ ID NO: 47) and WCBV (SEQ ID NO: 49) were confirmed by sequencing. Two extra transcription units were synthesized (each with the sequence of SEQ ID NO: 42) and introduced into the gene junctions between the phosphoprotein (P) and the matrix protein (M), and the G and the RNA dependent RNA polymerase (L) (FIG. 4). The MOKV G was cloned into the gene junction between the P and M, and WCBV G into the gene junction between the G and L in the ERA genome backbone.

Recombinant virus was recovered by transfection of the above described construct into BSR cells using the method described in Example 3. Approximately 5-7 days following transfection, BSR cells were fixed for DFA staining using FITC-conjugated anti-rabies antibodies.

The recovered ERA-3G virus was characterized with a one-step growth curve in BSR cells. Virus titer was evaluated at 24, 48, 72, 96 and 120 hours after infection. At the 72, 96 and 120 hour time points, virus titer in bioreactor incubation ranged from $10^8$ to $10^9$ focus forming unit (ffu)/ml.

ERA-3G virus was then tested in a hamster model to determine whether vaccination with ERA-3G provides protection against challenge with RABV, LBV, MOKV and/or WCBV. Nine hamsters were vaccinated (i.m.) with either ERA-3G, RabAvert™ (Chiron Corporation, Emeryville, Calif.), or IMRAB™ (Merial, Duluth, Ga.). RabAvert™ was administered on days 0, 7 and 14, while ERA-3G and IMRAB™ were administered on day 0. Animals were challenged with RABV, LBV, MOK or WCBV on day 22. Control animals received no vaccine. The results of the challenge experiment are shown in Table 2.

TABLE 2

Survivorship of hamsters after pre-exposure vaccination and i.m. challenge with several lyssaviruses

| Group | RABV (I-151) | LBV (SA) | MOK (SA) | WCBV |
|---|---|---|---|---|
| RabAvert ™ | 9/9 | 0/9 | 0/9 | 5/9 |
| IMRAB ™ | 9/9 | 1/9 | 0/9 | 3/9 |
| ERA-3G | 9/9 | 1/9 | 9/9 | 9/9 |
| Control | 0/9 | 0/9 | 0/9 | 1/9 |

The results demonstrate that ERA-3G provides complete protection against RABV, MOK and WCBV. In contrast, the currently available vaccines RabAvert™ and IMRAB™, provide protection only against RABV.

For animal vaccine development, ERA-3G will be adapted to growth in chicken embryo fibroblast (CEF) and Vero cells. It is believed that ERA-3G will grow to high titers ranging from $10^8$ to$10^9$ ffu/ml in the BSR cells for animal vaccine development. For human vaccine development, ERA-3G will be adapted to CEF and Vero cells. It is believed that ERA-3G titers in the CEF and BSR cells after adaptation will be comparable to virus growth in BSR cells. The purity of ERA-3G will be verified, and the seed virus will be prepared for industrial production. Potential mycoplasma contamination will be tested using a standard PCR method.

Example 7

Construction and Characterization of Recombinant Rabies Virus with Four Glycoprotein Genes This example describes the generation and characterization of a recombinant ERA strain rabies virus encoding three different glycoprotein genes. The recombinant virus, referred to as ERA-4G, comprises rabies virus glycoprotein, Lagos bat virus (LBV) glycoprotein, MOKV glycoprotein and WCBV glycoprotein. The cloning strategy for ERA-4G is shown in FIG. 5. The rabies virus reverse genetics system used to generate this virus in described in the Examples above. ERA-4G includes the attenuating mutation in the G gene that results in an arginine to glutamic acid change at amino acid residue 433 of the protein (SEQ ID NO: 5).

The G genes from LBV, MOKV and WCBV were cloned into the ERA backbone by RT-PCR using viral genomic RNA as template from virus-infected cells. The following primers were used for amplification of the glycoprotein genes:

```
                                    (SEQ ID NO: 51)
LagosG5-CGACTGCAGATGAGTCAACTAAATTTGATACCCTTTTTC

                                    (SEQ ID NO: 52)
LagosG3-CCGTACGTATCAGACATTAGAGGTACCCTTATAAGATTCCCA

                                    (SEQ ID NO: 43)
MokolaG5-CGACTGCAGATGAATATACCTTGCTTTGTTGTGATTC

                                    (SEQ ID NO: 44)
MokolaG3-CGTGGTACCTCATGTACCTGGAAGCCCTTTATAGGACTC

                                    (SEQ ID NO: 45)
WCBVG5-CATCTGCTAGCAATGGCTTCCTACTTTGCGTTG

                                    (SEQ ID NO: 46)
WCBVG3-TTCAATGGTACCTTATTGGGCAGTTTGTCCCTT
```

The amplified G genes for LBV (SEQ ID NO: 53), MOKV (SEQ ID NO: 47) and WCBV (SEQ ID NO: 49) were confirmed by sequencing. Three extra transcription units were synthesized (each with the sequence of SEQ ID NO: 42) and introduced into the gene junctions between the N and P genes, between the P and M genes, and the G and L genes (FIG. 5). The LBV G was cloned into the gene junction between N and P, MOKV G was cloned into the gene junction between P and M, and WCBV G was cloned into the gene junction between the G and L in the ERA genome backbone.

Recombinant virus was recovered by transfection of the above described construct into BSR cells using the method described in Example 3. Approximately 5-7 days following transfection, BSR cells were fixed for DFA staining using FITC-conjugated anti-rabies antibodies.

The recovered ERA-4G virus was characterized with a one-step growth curve in BSR cells. Virus titer was determined at 24, 48, 72, 96 and 120 hours after infection. The results are shown in Table 3 below.

TABLE 3

Growth of ERA-4G in BSR cells

| Timepoint (h) | 24 | 48 | 72 | 96 | 120 |
|---|---|---|---|---|---|
| Titer (ffu/ml) | $1 \times 10^3$ | $5 \times 10^3$ | $1.2 \times 10^5$ | $1.3 \times 10^7$ | $3.2 \times 10^5$ |

ERA-4G virus will be tested in a hamster model to determine whether vaccination with ERA-4G confers protection against challenge with *lyssaviruses* RABV, LBV, MOKV and WCBV. The vaccination and challenge experiment will be performed as described for ERA-3G in Example 6.

For animal vaccine development, ERA-4G will be adapted to growth in chicken embryo fibroblast (CEF) and Vero cells. It is believed that ERA-4G will grow to high titers ranging from $10^8$ to $10^9$ ffu/ml in the BSR cells for animal vaccine development. For human vaccine development, ERA-4G will be adapted to CEF and Vero cells. It is believed that ERA-4G titers in the CEF and BSR cells after adaptation will be comparable to virus growth in BSR cells. The purity of ERA-4G will be verified, and the seed virus will be prepared for industrial production. Potential mycoplasma contamination will be tested using a standard PCR method.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A recombinant rabies virus, the genome of which comprises rabies virus nucleoprotein (N), phosphoprotein (P), matrix protein (M), RNA-dependent RNA polymerase (L) and glycoprotein (G) genes and three different heterologous *lyssavirus* G genes, wherein the heterologous *lyssavirus* G genes are located between the rabies virus P and M genes, between the rabies virus G and L genes, and between the rabies virus N and P genes, and wherein the *lyssavirus* is selected from the group consisting of Lagos bat virus (LBV), Mokola virus (MOKV), Duvenhage virus (DUVV), European bat *lyssavirus*-1 (EBLV-1), European bat *lyssavirus*-2 (EBLV-2), Australian bat *lyssavirus* (ABLV), Aravan virus (ARAV), Khujand virus (KHUV), Irkut virus (IRKV) and West Caucasian bat virus (WCBV).

2. The recombinant rabies virus of claim 1, wherein the three heterologous G genes are LBV, MOKV and WCBV G genes.

3. The recombinant rabies virus of claim 2, wherein the nucleotide sequence of the LBV G gene is at least 95% identical to the nucleotide sequence of SEQ ID NO: 53, the nucleotide sequence of the MOKV G gene is at least 95% identical to the nucleotide sequence of SEQ ID NO: 47, or the nucleotide sequence of the WCBV G gene is at least 95% identical to the nucleotide sequence of SEQ ID NO: 49.

4. The recombinant rabies virus of claim 2, wherein the LBV G gene comprises the nucleotide sequence of SEQ ID NO: 53, the MOKV G gene comprises the nucleotide sequence of SEQ ID NO: 47, or the WCBV G gene comprises the nucleotide sequence of SEQ ID NO: 49.

5. The recombinant rabies virus of claim 1, wherein the genome is derived from the rabies virus ERA strain.

6. The recombinant rabies virus of claim 1, wherein the rabies virus glycoprotein comprises a Glu at amino acid position 333 (SEQ ID NO: 5).

7. A vector comprising a full-length rabies virus antigenomic DNA, wherein the antigenomic DNA comprises rabies virus N, P, M, L and G genes, and three different heterologous *lyssavirus* G genes, wherein the heterologous *lyssavirus* G genes are located between the rabies virus P and M genes, between the rabies virus G and L genes, and between the rabies virus N and P genes, and wherein the *lyssavirus* is selected from LBV, MOKV, DUVV, EBLV-1, EBLV-2, ABLV, ARAV, KHUV, IRKV and WCBV.

8. The vector of claim 7, wherein the three heterologous G genes are LBV, MOKV and WCBV G genes.

9. The vector of claim 8, wherein the nucleotide sequence of the LBV G gene is at least 95% identical to the nucleotide sequence of SEQ ID NO: 53, the nucleotide sequence of the MOKV G gene is at least 95% identical to the nucleotide sequence of SEQ ID NO: 47, or the nucleotide sequence of the WCBV G gene is at least 95% identical to the nucleotide sequence of SEQ ID NO: 49.

10. The vector of claim 8, wherein the LBV G gene comprises the nucleotide sequence of SEQ ID NO: 53, the MOKV G gene comprises the nucleotide sequence of SEQ ID NO: 47, or the WCBV G gene comprises the nucleotide sequence of SEQ ID NO: 49.

11. The vector of claim 7, wherein the antigenomic DNA is derived from the rabies virus ERA strain.

12. A cell comprising the vector of claim 7.

13. A composition comprising the recombinant rabies virus of claim 1 and a pharmaceutically acceptable carrier.

14. A method of eliciting an immune response in a subject against *lyssavirus*, comprising administering to the subject the recombinant rabies virus of claim 1.

15. The method of claim 14, wherein the immune response in the subject against *lyssavirus* protects the subject against infection by at least three or at least four different genotypes of *lyssavirus*.

* * * * *

SEQUENCE LISTING

```
<160> NUMBER OF SEQ ID NOS: 54

<210> SEQ ID NO 1
<211> LENGTH: 11930
<212> TYPE: DNA
<213> ORGANISM: Artificial Sequence
<220> FEATURE:
<223> OTHER INFORMATION: Recombinant ERA rabies virus genome
<220> FEATURE:
<221> NAME/KEY: misc_feature
<222> LOCATION: (1)..(58)
<223> OTHER INFORMATION: Leader region
<220> FEATURE:
<221> NAME/KEY: CDS
<222> LOCATION: (71)..(1420)
<223> OTHER INFORMATION: N gene
<220> FEATURE:
<221> NAME/KEY: CDS
<222> LOCATION: (1514)..(2404)
<223> OTHER INFORMATION: P gene
<220> FEATURE:
<221> NAME/KEY: CDS
<222> LOCATION: (2496)..(3101)
<223> OTHER INFORMATION: M gene
<220> FEATURE:
<221> NAME/KEY: CDS
<222> LOCATION: (3317)..(4888)
<223> OTHER INFORMATION: G gene
<220> FEATURE:
<221> NAME/KEY: misc_feature
<222> LOCATION: (4963)..(5361)
<223> OTHER INFORMATION: Psi region
```

```
<220> FEATURE:
<221> NAME/KEY: CDS
<222> LOCATION: (5416)..(11796)
<223> OTHER INFORMATION: L gene
<220> FEATURE:
<221> NAME/KEY: misc_feature
<222> LOCATION: (11861)..(11930)
<223> OTHER INFORMATION: Trailer region

<400> SEQUENCE: 1

acgcttaaca accagatcaa agaaaaaaca gacattgtca attgcaaagc aaaaatgtaa      60

cacccctaca atg gat gcc gac aag att gta ttc aaa gtc aat aat cag        109
           Met Asp Ala Asp Lys Ile Val Phe Lys Val Asn Asn Gln
           1               5                   10

gtg gtc tct ttg aag cct gag att atc gtg gat caa cat gag tac aag       157
Val Val Ser Leu Lys Pro Glu Ile Ile Val Asp Gln His Glu Tyr Lys
    15                  20                  25

tac cct gcc atc aaa gat ttg aaa aag ccc tgt ata acc cta gga aag       205
Tyr Pro Ala Ile Lys Asp Leu Lys Lys Pro Cys Ile Thr Leu Gly Lys
30                  35                  40                  45

gct ccc gat tta aat aaa gca tac aag tca gtt ttg tca ggc atg agc       253
Ala Pro Asp Leu Asn Lys Ala Tyr Lys Ser Val Leu Ser Gly Met Ser
                50                  55                  60

gcc gcc aaa ctt gat cct gac gat gta tgt tcc tat ttg gca gcg gca       301
Ala Ala Lys Leu Asp Pro Asp Asp Val Cys Ser Tyr Leu Ala Ala Ala
            65                  70                  75

atg cag ttt ttt gag ggg aca tgt ccg gaa gac tgg acc agc tat gga       349
Met Gln Phe Phe Glu Gly Thr Cys Pro Glu Asp Trp Thr Ser Tyr Gly
        80                  85                  90

atc gtg att gca cga aaa gga gat aag atc acc cca ggt tct ctg gtg       397
Ile Val Ile Ala Arg Lys Gly Asp Lys Ile Thr Pro Gly Ser Leu Val
    95                  100                 105

gag ata aaa cgt act gat gta gaa ggg aat tgg gct ctg aca gga ggc       445
Glu Ile Lys Arg Thr Asp Val Glu Gly Asn Trp Ala Leu Thr Gly Gly
110                 115                 120                 125

atg gaa ctg aca aga gac ccc act gtc cct gag cat gcg tcc tta gtc       493
Met Glu Leu Thr Arg Asp Pro Thr Val Pro Glu His Ala Ser Leu Val
                130                 135                 140

ggt ctt ctc ttg agt ctg tat agg ttg agc aaa ata tcc ggg caa aac       541
Gly Leu Leu Leu Ser Leu Tyr Arg Leu Ser Lys Ile Ser Gly Gln Asn
            145                 150                 155

act ggt aac tat aag aca aac att gca gac agg ata gag cag att ttt       589
Thr Gly Asn Tyr Lys Thr Asn Ile Ala Asp Arg Ile Glu Gln Ile Phe
        160                 165                 170

gag aca gcc cct ttt gtt aaa atc gtg gaa cac cat act cta atg aca       637
Glu Thr Ala Pro Phe Val Lys Ile Val Glu His His Thr Leu Met Thr
    175                 180                 185

act cac aaa atg tgt gct aat tgg agt act ata cca aac ttc aga ttt       685
Thr His Lys Met Cys Ala Asn Trp Ser Thr Ile Pro Asn Phe Arg Phe
190                 195                 200                 205

ttg gcc gga acc tat gac atg ttt ttc tcc cgg att gag cat cta tat       733
Leu Ala Gly Thr Tyr Asp Met Phe Phe Ser Arg Ile Glu His Leu Tyr
                210                 215                 220

tca gca atc aga gtg ggc aca gtt gtc act gct tat gaa gac tgt tca       781
Ser Ala Ile Arg Val Gly Thr Val Val Thr Ala Tyr Glu Asp Cys Ser
            225                 230                 235

gga ctg gta tca ttt act ggg ttc ata aaa caa atc aat ctc acc gct       829
Gly Leu Val Ser Phe Thr Gly Phe Ile Lys Gln Ile Asn Leu Thr Ala
        240                 245                 250
```

```
aga gag gca ata cta tat ttc ttc cac aag aac ttt gag gaa gag ata      877
Arg Glu Ala Ile Leu Tyr Phe Phe His Lys Asn Phe Glu Glu Glu Ile
    255                 260                 265

aga aga atg ttt gag cca ggg cag gag aca gct gtt cct cac tct tat      925
Arg Arg Met Phe Glu Pro Gly Gln Glu Thr Ala Val Pro His Ser Tyr
270                 275                 280                 285

ttc atc cac ttc cgt tca cta ggc ttg agt ggg aaa tct cct tat tca      973
Phe Ile His Phe Arg Ser Leu Gly Leu Ser Gly Lys Ser Pro Tyr Ser
                290                 295                 300

tca aat gct gtt ggt cac gtg ttc aat ctc att cac ttt gta gga tgc     1021
Ser Asn Ala Val Gly His Val Phe Asn Leu Ile His Phe Val Gly Cys
            305                 310                 315

tat atg ggt caa gtc aga tcc cta aat gca acg gtt att gct gca tgt     1069
Tyr Met Gly Gln Val Arg Ser Leu Asn Ala Thr Val Ile Ala Ala Cys
        320                 325                 330

gct cct cat gaa atg tct gtt cta ggg ggc tat ctg gga gag gaa ttc     1117
Ala Pro His Glu Met Ser Val Leu Gly Gly Tyr Leu Gly Glu Glu Phe
    335                 340                 345

ttc ggg aaa ggg aca ttt gaa aga aga ttc ttc aga gat gag aaa gaa     1165
Phe Gly Lys Gly Thr Phe Glu Arg Arg Phe Phe Arg Asp Glu Lys Glu
350                 355                 360                 365

ctt caa gaa tac gag gcg gct gaa ctg aca aag act gac gta gca ctg     1213
Leu Gln Glu Tyr Glu Ala Ala Glu Leu Thr Lys Thr Asp Val Ala Leu
                370                 375                 380

gca gat gat gga act gtc aac tct gac gac gag gac tac ttc tca ggt     1261
Ala Asp Asp Gly Thr Val Asn Ser Asp Asp Glu Asp Tyr Phe Ser Gly
            385                 390                 395

gaa acc aga agt ccg gag gct gtt tat act cga atc atg atg aat gga     1309
Glu Thr Arg Ser Pro Glu Ala Val Tyr Thr Arg Ile Met Met Asn Gly
        400                 405                 410

ggt cga cta aag aga tct cac ata cgg aga tat gtc tca gtc agt tcc     1357
Gly Arg Leu Lys Arg Ser His Ile Arg Arg Tyr Val Ser Val Ser Ser
    415                 420                 425

aat cat caa gcc cgt cca aac tca ttc gcc gag ttt cta aac aag aca     1405
Asn His Gln Ala Arg Pro Asn Ser Phe Ala Glu Phe Leu Asn Lys Thr
430                 435                 440                 445

tat tcg agt gac tca taagaagttg aacaacaaaa tgccggaaat ctacggattg     1460
Tyr Ser Ser Asp Ser
                450

tgtatatcca tcatgaaaaa aactaacacc cctcctttcg aaccatccca aac atg      1516
                                                           Met

agc aag atc ttt gtc aat cct agt gct att aga gcc ggt ctg gcc gat     1564
Ser Lys Ile Phe Val Asn Pro Ser Ala Ile Arg Ala Gly Leu Ala Asp
            455                 460                 465

ctt gag atg gct gaa gaa act gtt gat ctg atc aat aga aat atc gaa     1612
Leu Glu Met Ala Glu Glu Thr Val Asp Leu Ile Asn Arg Asn Ile Glu
        470                 475                 480

gac aat cag gct cat ctc caa ggg gaa ccc ata gaa gtg gac aat ctc     1660
Asp Asn Gln Ala His Leu Gln Gly Glu Pro Ile Glu Val Asp Asn Leu
    485                 490                 495

cct gag gat atg ggg cga ctt cac ctg gat gat gga aaa tcg ccc aac     1708
Pro Glu Asp Met Gly Arg Leu His Leu Asp Asp Gly Lys Ser Pro Asn
500                 505                 510                 515

cct ggt gag atg gcc aag gtg gga gaa ggc aag tat cga gag gac ttt     1756
Pro Gly Glu Met Ala Lys Val Gly Glu Gly Lys Tyr Arg Glu Asp Phe
                520                 525                 530

cag atg gat gaa gga gag gat ctt agc ttc ctg ttc cag tca tac ctg     1804
Gln Met Asp Glu Gly Glu Asp Leu Ser Phe Leu Phe Gln Ser Tyr Leu
            535                 540                 545
```

-continued

```
gaa aat gtt gga gtc caa ata gtc aga caa atg agg tca gga gag aga      1852
Glu Asn Val Gly Val Gln Ile Val Arg Gln Met Arg Ser Gly Glu Arg
        550                 555                 560

ttt ctc aag ata tgg tca cag acc gta gaa gag att ata tcc tat gtc      1900
Phe Leu Lys Ile Trp Ser Gln Thr Val Glu Glu Ile Ile Ser Tyr Val
    565                 570                 575

gcg gtc aac ttt ccc aac cct cca gga aag tct tca gag gat aaa tca      1948
Ala Val Asn Phe Pro Asn Pro Pro Gly Lys Ser Ser Glu Asp Lys Ser
580                 585                 590                 595

acc cag act act ggc cga gag ctc aag aag gag aca aca ccc act cct      1996
Thr Gln Thr Thr Gly Arg Glu Leu Lys Lys Glu Thr Thr Pro Thr Pro
                600                 605                 610

tct cag aga gaa agc caa tca tcg aaa gcc agg atg gcg gct caa att      2044
Ser Gln Arg Glu Ser Gln Ser Ser Lys Ala Arg Met Ala Ala Gln Ile
            615                 620                 625

gct tct ggc cct cca gcc ctt gaa tgg tcg gcc acc aat gaa gag gat      2092
Ala Ser Gly Pro Pro Ala Leu Glu Trp Ser Ala Thr Asn Glu Glu Asp
        630                 635                 640

gat cta tca gtg gag gct gag atc gct cac cag att gca gaa agt ttc      2140
Asp Leu Ser Val Glu Ala Glu Ile Ala His Gln Ile Ala Glu Ser Phe
    645                 650                 655

tcc aaa aaa tat aag ttt ccc tct cga tcc tca ggg ata ctc ttg tat      2188
Ser Lys Lys Tyr Lys Phe Pro Ser Arg Ser Ser Gly Ile Leu Leu Tyr
660                 665                 670                 675

aat ttt gag caa ttg aaa atg aac ctt gat gat ata gtt aaa gag gca      2236
Asn Phe Glu Gln Leu Lys Met Asn Leu Asp Asp Ile Val Lys Glu Ala
                680                 685                 690

aaa aat gta cca ggt gtg acc cgt tta gcc cat gac ggg tcc aaa ctc      2284
Lys Asn Val Pro Gly Val Thr Arg Leu Ala His Asp Gly Ser Lys Leu
            695                 700                 705

ccc cta aga tgt gta ctg gga tgg gtc gct ttg gcc aac cct aag aaa      2332
Pro Leu Arg Cys Val Leu Gly Trp Val Ala Leu Ala Asn Pro Lys Lys
        710                 715                 720

ttc cag ttg tta gtc gaa tcc gac aag ctg agt aaa atc atg caa gat      2380
Phe Gln Leu Leu Val Glu Ser Asp Lys Leu Ser Lys Ile Met Gln Asp
    725                 730                 735

gac ttg aat cgc tat aca tct tgc taaccgaacc tctccactca gtccctctag      2434
Asp Leu Asn Arg Tyr Thr Ser Cys
740                 745

acaataaagt ccgagatgtc ctaaagtcaa catgaaaaaa acaggcaaca ccactgataa    2494

a atg aac ttt cta cgt aag ata gtg aaa aat tgc agg gac gag gac act    2543
  Met Asn Phe Leu Arg Lys Ile Val Lys Asn Cys Arg Asp Glu Asp Thr
          750                 755                 760

caa aaa ccc tct ccc gtg tca gcc cct ctg gat gac gat gac ttg tgg      2591
Gln Lys Pro Ser Pro Val Ser Ala Pro Leu Asp Asp Asp Asp Leu Trp
    765                 770                 775

ctt cca ccc cct gaa tac gtc ccg ctg aaa gaa ctt aca agc aag aag      2639
Leu Pro Pro Pro Glu Tyr Val Pro Leu Lys Glu Leu Thr Ser Lys Lys
780                 785                 790                 795

aac atg agg aac ttt tgt atc aac gga ggg gtt aaa gtg tgt agc ccg      2687
Asn Met Arg Asn Phe Cys Ile Asn Gly Gly Val Lys Val Cys Ser Pro
                800                 805                 810

aat ggt tac tcg ttc agg atc ctg cgg cac att ctg aaa tca ttc gac      2735
Asn Gly Tyr Ser Phe Arg Ile Leu Arg His Ile Leu Lys Ser Phe Asp
            815                 820                 825

gag ata tat tct ggg aat cat agg atg atc ggg tta gcc aaa gta gtt      2783
Glu Ile Tyr Ser Gly Asn His Arg Met Ile Gly Leu Ala Lys Val Val
        830                 835                 840

att gga ctg gct ttg tca gga tct cca gtc cct gag ggc atg aac tgg      2831
```

```
Ile Gly Leu Ala Leu Ser Gly Ser Pro Val Pro Glu Gly Met Asn Trp
    845                 850                 855

gta tac aaa ttg agg aga acc ttt atc ttc cag tgg gct gat tcc agg      2879
Val Tyr Lys Leu Arg Arg Thr Phe Ile Phe Gln Trp Ala Asp Ser Arg
860                 865                 870                 875

ggc cct ctt gaa ggg gag gag ttg gaa tac tct cag gag atc act tgg      2927
Gly Pro Leu Glu Gly Glu Glu Leu Glu Tyr Ser Gln Glu Ile Thr Trp
                880                 885                 890

gat gat gat act gag ttc gtc gga ttg caa ata aga gtg att gca aaa      2975
Asp Asp Asp Thr Glu Phe Val Gly Leu Gln Ile Arg Val Ile Ala Lys
            895                 900                 905

cag tgt cat atc cag ggc aga atc tgg tgt atc aac atg aac ccg aga      3023
Gln Cys His Ile Gln Gly Arg Ile Trp Cys Ile Asn Met Asn Pro Arg
        910                 915                 920

gca tgt caa cta tgg tct gac atg tct ctt cag aca caa agg tcc gaa      3071
Ala Cys Gln Leu Trp Ser Asp Met Ser Leu Gln Thr Gln Arg Ser Glu
    925                 930                 935

gag gac aaa gat tcc tct ctg ctt cta gaa taatcagatt atatcccgca        3121
Glu Asp Lys Asp Ser Ser Leu Leu Leu Glu
940                 945

aatttatcac ttgtttacct ctggaggaga gaacatatgg gctcaactcc aacccttggg   3181

agcaatataa caaaaaacat gttatggtgc cattaaaccg ctgcatttca tcaaagtcaa   3241

gttgattacc tttacatttt gatcctcttg gatgtgaaaa aaactattaa catccctcaa   3301

aagactcaag gaaag atg gtt cct cag gct ctc ctg ttt gta ccc ctt ctg     3352
                 Met Val Pro Gln Ala Leu Leu Phe Val Pro Leu Leu
                 950                 955                 960

gtt ttt cca ttg tgt ttt ggg aaa ttc cct att tac acg ata cca gac      3400
Val Phe Pro Leu Cys Phe Gly Lys Phe Pro Ile Tyr Thr Ile Pro Asp
            965                 970                 975

aag ctt ggt ccc tgg agc ccg att gac ata cat cac ctc agc tgc cca      3448
Lys Leu Gly Pro Trp Ser Pro Ile Asp Ile His His Leu Ser Cys Pro
        980                 985                 990

aac aat ttg gta gtg gag gac  gaa gga tgc acc aac  ctg tca ggg ttc    3496
Asn Asn Leu Val Val Glu Asp  Glu Gly Cys Thr Asn  Leu Ser Gly Phe
    995                 1000                 1005

tcc  tac atg gaa ctt aaa  gtt gga tac atc tta  gcc ata aaa atg       3541
Ser  Tyr Met Glu Leu Lys  Val Gly Tyr Ile Leu  Ala Ile Lys Met
1010                 1015                 1020

aac  ggg ttc act tgc aca  ggc gtt gtg acg gag  gct gaa acc tat       3586
Asn  Gly Phe Thr Cys Thr  Gly Val Val Thr Glu  Ala Glu Thr Tyr
1025                 1030                 1035

act  aac ttc gtt ggt tat  gtc aca acc acg ttc  aaa aga aag cat       3631
Thr  Asn Phe Val Gly Tyr  Val Thr Thr Thr Phe  Lys Arg Lys His
1040                 1045                 1050

ttc  cgc cca aca cca gat  gca tgt aga gcc gcg  tac aac tgg aag       3676
Phe  Arg Pro Thr Pro Asp  Ala Cys Arg Ala Ala  Tyr Asn Trp Lys
1055                 1060                 1065

atg  gcc ggt gac ccc aga  tat gaa gag tct cta  cac aat ccg tac       3721
Met  Ala Gly Asp Pro Arg  Tyr Glu Glu Ser Leu  His Asn Pro Tyr
1070                 1075                 1080

cct  gac tac cac tgg ctt  cga act gta aaa acc  acc aag gag tct       3766
Pro  Asp Tyr His Trp Leu  Arg Thr Val Lys Thr  Thr Lys Glu Ser
1085                 1090                 1095

ctc  gtt atc ata tct cca  agt gtg gca gat ttg  gac cca tat gac       3811
Leu  Val Ile Ile Ser Pro  Ser Val Ala Asp Leu  Asp Pro Tyr Asp
1100                 1105                 1110

aga  tcc ctt cac tcg agg  gtc ttc cct agc ggg  aag tgc tca gga       3856
Arg  Ser Leu His Ser Arg  Val Phe Pro Ser Gly  Lys Cys Ser Gly
```

-continued

```
1115                1120                1125

gta  gcg gtg tct tct acc  tac tgc tcc act aac  cac gat tac acc      3901
Val  Ala Val Ser Ser Thr  Tyr Cys Ser Thr Asn  His Asp Tyr Thr
1130                1135                1140

att  tgg atg ccc gag aat  ccg aga cta ggg atg  tct tgt gac att      3946
Ile  Trp Met Pro Glu Asn  Pro Arg Leu Gly Met  Ser Cys Asp Ile
1145                1150                1155

ttt  acc aat agt agg ggg  aag aga gca tcc aaa  ggg agt gag act      3991
Phe  Thr Asn Ser Arg Gly  Lys Arg Ala Ser Lys  Gly Ser Glu Thr
1160                1165                1170

tgc  ggc ttt gta gat gaa  aga ggc cta tat aag  tct tta aaa gga      4036
Cys  Gly Phe Val Asp Glu  Arg Gly Leu Tyr Lys  Ser Leu Lys Gly
1175                1180                1185

gca  tgc aaa ctc aag tta  tgt gga gtt cta gga  ctt aga ctt atg      4081
Ala  Cys Lys Leu Lys Leu  Cys Gly Val Leu Gly  Leu Arg Leu Met
1190                1195                1200

gat  gga aca tgg gtc gcg  atg caa aca tca aat  gaa acc aaa tgg      4126
Asp  Gly Thr Trp Val Ala  Met Gln Thr Ser Asn  Glu Thr Lys Trp
1205                1210                1215

tgc  ccc ccc gat cag ttg  gtg aac ctg cac gac  ttt cgc tca gac      4171
Cys  Pro Pro Asp Gln Leu  Val Asn Leu His Asp  Phe Arg Ser Asp
1220                1225                1230

gaa  att gag cac ctt gtt  gta gag gag ttg gtc  agg aag aga gag      4216
Glu  Ile Glu His Leu Val  Val Glu Glu Leu Val  Arg Lys Arg Glu
1235                1240                1245

gag  tgt ctg gat gca cta  gag tcc atc atg aca  acc aag tca gtg      4261
Glu  Cys Leu Asp Ala Leu  Glu Ser Ile Met Thr  Thr Lys Ser Val
1250                1255                1260

agt  ttc aga cgt ccc agt  cat tta aga aaa ctt  gtc cct ggg ttt      4306
Ser  Phe Arg Arg Pro Ser  His Leu Arg Lys Leu  Val Pro Gly Phe
1265                1270                1275

gga  aaa gca tat acc ata  ttc aac aag acc ttg  atg gaa gcc gat      4351
Gly  Lys Ala Tyr Thr Ile  Phe Asn Lys Thr Leu  Met Glu Ala Asp
1280                1285                1290

gct  cac tac aag tca gtc  gag act tgg aat gag  atc ctc cct tca      4396
Ala  His Tyr Lys Ser Val  Glu Thr Trp Asn Glu  Ile Leu Pro Ser
1295                1300                1305

aaa  ggg tgt tta aga gtt  ggg ggg agg tgt cat  cct cat gtg aac      4441
Lys  Gly Cys Leu Arg Val  Gly Gly Arg Cys His  Pro His Val Asn
1310                1315                1320

ggg  gtg ttt ttc aat ggt  ata ata tta gga cct  gac ggc aat gtc      4486
Gly  Val Phe Phe Asn Gly  Ile Ile Leu Gly Pro  Asp Gly Asn Val
1325                1330                1335

tta  atc cca gag atg caa  tca tcc ctc ctc cag  caa cat atg gag      4531
Leu  Ile Pro Glu Met Gln  Ser Ser Leu Leu Gln  Gln His Met Glu
1340                1345                1350

ttg  ttg gaa tcc tcg gtt  atc ccc ctt gtg cac  ccc ctg gca gac      4576
Leu  Leu Glu Ser Ser Val  Ile Pro Leu Val His  Pro Leu Ala Asp
1355                1360                1365

ccg  tct acc gtt ttc aag  gac ggt gac gag gct  gag gat ttt gtt      4621
Pro  Ser Thr Val Phe Lys  Asp Gly Asp Glu Ala  Glu Asp Phe Val
1370                1375                1380

gaa  gtt cac ctt ccc gat  gtg cac aat cag gtc  tca gga gtt gac      4666
Glu  Val His Leu Pro Asp  Val His Asn Gln Val  Ser Gly Val Asp
1385                1390                1395

ttg  ggt ctc ccg aac tgg  ggg aag tat gta tta  ctg agt gca ggg      4711
Leu  Gly Leu Pro Asn Trp  Gly Lys Tyr Val Leu  Leu Ser Ala Gly
1400                1405                1410

gcc  ctg act gcc ttg atg  ttg ata att ttc ctg  atg aca tgt tgt      4756
```

-continued

```
Ala  Leu Thr Ala Leu Met  Leu Ile Ile Phe Leu  Met Thr Cys Cys
1415                1420                1425

aga  aga gtc aat cga tca  gaa cct acg caa cac  aat ctc aga ggg      4801
Arg  Arg Val Asn Arg Ser  Glu Pro Thr Gln His  Asn Leu Arg Gly
1430                1435                1440

aca  ggg agg gag gtg tca  gtc act ccc caa agc  ggg aag atc ata      4846
Thr  Gly Arg Glu Val Ser  Val Thr Pro Gln Ser  Gly Lys Ile Ile
1445                1450                1455

tct  tca tgg gaa tca cac  aag agt ggg ggt gag  acc aga ctg          4888
Ser  Ser Trp Glu Ser His  Lys Ser Gly Gly Glu  Thr Arg Leu
1460                1465                1470

tgaggactgg ccgtcctttc aactatccaa gtcctgaaga tcacctcccc ttggggggtt   4948

ctttttgaaa aaaacctggg ttcaatagtc ctcctcgaac tccatgcaac tgggtagatt   5008

caagagtcat gagattttca ttaatcctct cagttgatca agcaagatca tgtagattct   5068

cataataggg gagatcttct agcagtttca gtgactaacg gtactttcat tctccaggaa   5128

ctgacaccaa cagttgtaga caaaccacgg ggtgtctcgg gtgactctgt gcttgggcac   5188

agacaaaggt catggtgtgt tccatgatag cggactcagg atgagttaat tgagagaggc   5248

agtcttcctc ccgtgaagga cataagcagt agctcacaat catcccgcgt ctcagcaaag   5308

tgtgcataat tataaagtgc tgggtcatct aagcttttca gtcgagaaaa aaacattaga   5368

tcagaagaac aactggcaac acttctcaac ctgagaccta cttcaag atg ctc  gat    5424
                                                    Met Leu  Asp
                                                        1475

cct gga gag gtc  tat gat gac cct att  gac cca atc gag tta  gag      5469
Pro Gly Glu Val  Tyr Asp Asp Pro Ile  Asp Pro Ile Glu Leu  Glu
            1480                1485                1490

gat gaa ccc aga  gga acc ccc act gtc  ccc aac atc ttg agg  aac      5514
Asp Glu Pro Arg  Gly Thr Pro Thr Val  Pro Asn Ile Leu Arg  Asn
            1495                1500                1505

tct gac tac aat  ctc aac tct cct ttg  ata gaa gat cct gct  aga      5559
Ser Asp Tyr Asn  Leu Asn Ser Pro Leu  Ile Glu Asp Pro Ala  Arg
            1510                1515                1520

cta atg tta gaa  tgg tta aaa aca ggg  aat aga cct tat cgg  atg      5604
Leu Met Leu Glu  Trp Leu Lys Thr Gly  Asn Arg Pro Tyr Arg  Met
            1525                1530                1535

act cta aca gac  aat tgc tcc agg tct  ttc aga gtt ttg aaa  gat      5649
Thr Leu Thr Asp  Asn Cys Ser Arg Ser  Phe Arg Val Leu Lys  Asp
            1540                1545                1550

tat ttc aag aag  gta gat ttg ggt tct  ctc aag gtg ggc gga  atg      5694
Tyr Phe Lys Lys  Val Asp Leu Gly Ser  Leu Lys Val Gly Gly  Met
            1555                1560                1565

gct gca cag tca  atg att tct ctc tgg  tta tat ggt gcc cac  tct      5739
Ala Ala Gln Ser  Met Ile Ser Leu Trp  Leu Tyr Gly Ala His  Ser
            1570                1575                1580

gaa tcc aac agg  agc cgg aga tgt ata  aca gac ttg gcc cat  ttc      5784
Glu Ser Asn Arg  Ser Arg Arg Cys Ile  Thr Asp Leu Ala His  Phe
            1585                1590                1595

tat tcc aag tcg  tcc ccc ata gag aag  ctg ttg aat ctc acg  cta      5829
Tyr Ser Lys Ser  Ser Pro Ile Glu Lys  Leu Leu Asn Leu Thr  Leu
            1600                1605                1610

gga aat aga ggg  ctg aga atc ccc cca  gag gga gtg tta agt  tgc      5874
Gly Asn Arg Gly  Leu Arg Ile Pro Pro  Glu Gly Val Leu Ser  Cys
            1615                1620                1625

ctt gag agg gtt  gat tat gat aat gca  ttt gga agg tat ctt  gcc      5919
Leu Glu Arg Val  Asp Tyr Asp Asn Ala  Phe Gly Arg Tyr Leu  Ala
            1630                1635                1640
```

```
aac acg tat tcc  tct tac ttg ttc ttc  cat gta atc acc tta  tac      5964
Asn Thr Tyr Ser  Ser Tyr Leu Phe Phe  His Val Ile Thr Leu  Tyr
            1645                 1650                 1655

atg aac gcc cta  gac tgg gat gaa gaa  aag acc atc cta gca  tta      6009
Met Asn Ala Leu  Asp Trp Asp Glu Glu  Lys Thr Ile Leu Ala  Leu
            1660                 1665                 1670

tgg aaa gat tta  acc tca gtg gac atc  ggg aag gac ttg gta  aag      6054
Trp Lys Asp Leu  Thr Ser Val Asp Ile  Gly Lys Asp Leu Val  Lys
            1675                 1680                 1685

ttc aaa gac caa  ata tgg gga ctg ccg  atc gtg aca aag gac  ttt      6099
Phe Lys Asp Gln  Ile Trp Gly Leu Pro  Ile Val Thr Lys Asp  Phe
            1690                 1695                 1700

gtt tac tcc caa  agt tcc aat tgt ctt  ttt gac aga aac tac  aca      6144
Val Tyr Ser Gln  Ser Ser Asn Cys Leu  Phe Asp Arg Asn Tyr  Thr
            1705                 1710                 1715

ctt atg cta aaa  gaa ctt ttc ttg tct  cgc ttc aac tcc tta  atg      6189
Leu Met Leu Lys  Glu Leu Phe Leu Ser  Arg Phe Asn Ser Leu  Met
            1720                 1725                 1730

gtc ttg ctc tct  ccc cca gag ccc cga  tac tca gat gac ttg  ata      6234
Val Leu Leu Ser  Pro Pro Glu Pro Arg  Tyr Ser Asp Asp Leu  Ile
            1735                 1740                 1745

tct caa cta tgc  cag ctg tac att gct  ggg gat caa gtc ttg  tct      6279
Ser Gln Leu Cys  Gln Leu Tyr Ile Ala  Gly Asp Gln Val Leu  Ser
            1750                 1755                 1760

atg tgt gga aac  tcc ggc tat gaa gtc  atc aaa ata ttg gag  cca      6324
Met Cys Gly Asn  Ser Gly Tyr Glu Val  Ile Lys Ile Leu Glu  Pro
            1765                 1770                 1775

tat gtc gtg aat  agt tta gtc cag aga  gca gaa aag ttt agg  cct      6369
Tyr Val Val Asn  Ser Leu Val Gln Arg  Ala Glu Lys Phe Arg  Pro
            1780                 1785                 1790

ctc att cat tcc  ttg gga gac ttt cct  gta ttt ata aaa gac  aag      6414
Leu Ile His Ser  Leu Gly Asp Phe Pro  Val Phe Ile Lys Asp  Lys
            1795                 1800                 1805

gta agt caa ctt  gaa gag acg ttc ggt  ccc tgt gca aga agg  ttc      6459
Val Ser Gln Leu  Glu Glu Thr Phe Gly  Pro Cys Ala Arg Arg  Phe
            1810                 1815                 1820

ttt agg gct ctg  gat caa ttc gac aac  ata cat gac ttg gtt  ttt      6504
Phe Arg Ala Leu  Asp Gln Phe Asp Asn  Ile His Asp Leu Val  Phe
            1825                 1830                 1835

gtg tat ggc tgt  tac agg cat tgg ggg  cac cca tat ata gat  tat      6549
Val Tyr Gly Cys  Tyr Arg His Trp Gly  His Pro Tyr Ile Asp  Tyr
            1840                 1845                 1850

cga aag ggt ctg  tca aaa cta tat gat  cag gtt cac att aaa  aaa      6594
Arg Lys Gly Leu  Ser Lys Leu Tyr Asp  Gln Val His Ile Lys  Lys
            1855                 1860                 1865

gtg ata gat aag  tcc tac cag gag tgc  tta gca agc gac cta  gcc      6639
Val Ile Asp Lys  Ser Tyr Gln Glu Cys  Leu Ala Ser Asp Leu  Ala
            1870                 1875                 1880

agg agg atc ctt  aga tgg ggt ttt gat  aag tac tcc aag tgg  tat      6684
Arg Arg Ile Leu  Arg Trp Gly Phe Asp  Lys Tyr Ser Lys Trp  Tyr
            1885                 1890                 1895

ctg gat tca aga  ttc cta gcc cga gac  cac ccc ttg act cct  tat      6729
Leu Asp Ser Arg  Phe Leu Ala Arg Asp  His Pro Leu Thr Pro  Tyr
            1900                 1905                 1910

atc aaa acc caa  aca tgg cca ccc aaa  cat att gta gac ttg  gtg      6774
Ile Lys Thr Gln  Thr Trp Pro Pro Lys  His Ile Val Asp Leu  Val
            1915                 1920                 1925

ggg gat aca tgg  cac aag ctc ccg atc  acg cag atc ttt gag  att      6819
Gly Asp Thr Trp  His Lys Leu Pro Ile  Thr Gln Ile Phe Glu  Ile
            1930                 1935                 1940
```

```
cct gaa tca atg  gat ccg tca gaa ata  ttg gat gac aaa tca  cat      6864
Pro Glu Ser Met  Asp Pro Ser Glu Ile  Leu Asp Asp Lys Ser  His
            1945                 1950                 1955

tct ttc acc aga  acg aga cta gct tct  tgg ctg tca gaa aac  cga      6909
Ser Phe Thr Arg  Thr Arg Leu Ala Ser  Trp Leu Ser Glu Asn  Arg
            1960                 1965                 1970

ggg gga cct gtt  cct agc gaa aaa gtt  att atc acg gcc ctg  tct      6954
Gly Gly Pro Val  Pro Ser Glu Lys Val  Ile Ile Thr Ala Leu  Ser
            1975                 1980                 1985

aag ccg cct gtc  aat ccc cga gag ttt  ctg agg tct ata gac  ctc      6999
Lys Pro Pro Val  Asn Pro Arg Glu Phe  Leu Arg Ser Ile Asp  Leu
            1990                 1995                 2000

gga gga ttg cca  gat gaa gac ttg ata  att ggc ctc aag cca  aag      7044
Gly Gly Leu Pro  Asp Glu Asp Leu Ile  Ile Gly Leu Lys Pro  Lys
            2005                 2010                 2015

gaa cgg gaa ttg  aag att gaa ggt cga  ttc ttt gct cta atg  tca      7089
Glu Arg Glu Leu  Lys Ile Glu Gly Arg  Phe Phe Ala Leu Met  Ser
            2020                 2025                 2030

tgg aat cta aga  ttg tat ttt gtc atc  act gaa aaa ctc ttg  gcc      7134
Trp Asn Leu Arg  Leu Tyr Phe Val Ile  Thr Glu Lys Leu Leu  Ala
            2035                 2040                 2045

aac tac atc ttg  cca ctt ttt gac gcg  ctg act atg aca gac  aac      7179
Asn Tyr Ile Leu  Pro Leu Phe Asp Ala  Leu Thr Met Thr Asp  Asn
            2050                 2055                 2060

ctg aac aag gtg  ttt aaa aag ctg atc  gac agg gtc acc ggg  caa      7224
Leu Asn Lys Val  Phe Lys Lys Leu Ile  Asp Arg Val Thr Gly  Gln
            2065                 2070                 2075

ggg ctt ttg gac  tat tca agg gtc aca  tat gca ttt cac ctg  gac      7269
Gly Leu Leu Asp  Tyr Ser Arg Val Thr  Tyr Ala Phe His Leu  Asp
            2080                 2085                 2090

tat gaa aag tgg  aac aac cat caa aga  tta gag tca aca gag  gat      7314
Tyr Glu Lys Trp  Asn Asn His Gln Arg  Leu Glu Ser Thr Glu  Asp
            2095                 2100                 2105

gta ttt tct gtc  cta gat caa gtg ttt  gga ttg aag aga gtg  ttt      7359
Val Phe Ser Val  Leu Asp Gln Val Phe  Gly Leu Lys Arg Val  Phe
            2110                 2115                 2120

tct aga aca cac  gag ttt ttt caa aag  gcc tgg atc tat tat  tca      7404
Ser Arg Thr His  Glu Phe Phe Gln Lys  Ala Trp Ile Tyr Tyr  Ser
            2125                 2130                 2135

gac aga tca gac  ctc atc ggg tta cgg  gag gat caa ata tac  tgc      7449
Asp Arg Ser Asp  Leu Ile Gly Leu Arg  Glu Asp Gln Ile Tyr  Cys
            2140                 2145                 2150

tta gat gcg tcc  aac ggc cca acc tgt  tgg aat ggc cag gat  ggc      7494
Leu Asp Ala Ser  Asn Gly Pro Thr Cys  Trp Asn Gly Gln Asp  Gly
            2155                 2160                 2165

ggg cta gaa ggc  tta cgg cag aag ggc  tgg agt cta gtc agc  tta      7539
Gly Leu Glu Gly  Leu Arg Gln Lys Gly  Trp Ser Leu Val Ser  Leu
            2170                 2175                 2180

ttg atg ata gat  aga gaa tct caa atc  agg aac aca aga acc  aaa      7584
Leu Met Ile Asp  Arg Glu Ser Gln Ile  Arg Asn Thr Arg Thr  Lys
            2185                 2190                 2195

ata cta gct caa  gga gac aac cag gtt  tta tgt ccg aca tat  atg      7629
Ile Leu Ala Gln  Gly Asp Asn Gln Val  Leu Cys Pro Thr Tyr  Met
            2200                 2205                 2210

ttg tcg cca ggg  cta tct caa gag ggg  ctc ctc tat gaa ttg  gag      7674
Leu Ser Pro Gly  Leu Ser Gln Glu Gly  Leu Leu Tyr Glu Leu  Glu
            2215                 2220                 2225

aga ata tca agg  aat gca ctt tcg ata  tac aga gcc gtc gag  gaa      7719
Arg Ile Ser Arg  Asn Ala Leu Ser Ile  Tyr Arg Ala Val Glu  Glu
```

```
            2230                2235                2240

ggg gca tct aag  cta ggg ctg atc atc  aag aaa gaa gag acc  atg      7764
Gly Ala Ser Lys  Leu Gly Leu Ile Ile  Lys Lys Glu Glu Thr  Met
            2245                2250                2255

tgt agt tat gac  ttc ctc atc tat gga  aaa acc cct ttg ttt  aga      7809
Cys Ser Tyr Asp  Phe Leu Ile Tyr Gly  Lys Thr Pro Leu Phe  Arg
            2260                2265                2270

ggt aac ata ttg  gtg cct gag tcc aaa  aga tgg gcc aga gtc  tct      7854
Gly Asn Ile Leu  Val Pro Glu Ser Lys  Arg Trp Ala Arg Val  Ser
            2275                2280                2285

tgc gtc tct aat  gac caa ata gtc aac  ctc gcc aat ata atg  tcg      7899
Cys Val Ser Asn  Asp Gln Ile Val Asn  Leu Ala Asn Ile Met  Ser
            2290                2295                2300

aca gtg tcc acc  aat gcg cta aca gtg  gca caa cac tct caa  tct      7944
Thr Val Ser Thr  Asn Ala Leu Thr Val  Ala Gln His Ser Gln  Ser
            2305                2310                2315

ttg atc aaa ccg  atg agg gat ttt ctg  ctc atg tca gta cag  gca      7989
Leu Ile Lys Pro  Met Arg Asp Phe Leu  Leu Met Ser Val Gln  Ala
            2320                2325                2330

gtc ttt cac tac  ctg cta ttt agc cca  atc tta aag gga aga  gtt      8034
Val Phe His Tyr  Leu Leu Phe Ser Pro  Ile Leu Lys Gly Arg  Val
            2335                2340                2345

tac aag att ctg  agc gct gaa ggg gat  agc ttt ctc cta gcc  atg      8079
Tyr Lys Ile Leu  Ser Ala Glu Gly Asp  Ser Phe Leu Leu Ala  Met
            2350                2355                2360

tca agg ata atc  tat cta gat cct tct  ttg gga ggg gta tct  gga      8124
Ser Arg Ile Ile  Tyr Leu Asp Pro Ser  Leu Gly Gly Val Ser  Gly
            2365                2370                2375

atg tcc ctc gga  aga ttc cat ata cga  cag ttc tca gac cct  gtc      8169
Met Ser Leu Gly  Arg Phe His Ile Arg  Gln Phe Ser Asp Pro  Val
            2380                2385                2390

tct gaa ggg tta  tcc ttc tgg aga gag  atc tgg tta agc tcc  cac      8214
Ser Glu Gly Leu  Ser Phe Trp Arg Glu  Ile Trp Leu Ser Ser  His
            2395                2400                2405

gag tcc tgg att  cac gcg ttg tgt caa  gag gct gga aac cca  gat      8259
Glu Ser Trp Ile  His Ala Leu Cys Gln  Glu Ala Gly Asn Pro  Asp
            2410                2415                2420

ctt gga gag aga  aca ctc gag agc ttc  act cgc ctt cta gaa  gat      8304
Leu Gly Glu Arg  Thr Leu Glu Ser Phe  Thr Arg Leu Leu Glu  Asp
            2425                2430                2435

cct acc acc tta  aat atc aga gga ggg  gcc agt cct acc att  cta      8349
Pro Thr Thr Leu  Asn Ile Arg Gly Gly  Ala Ser Pro Thr Ile  Leu
            2440                2445                2450

ctc aag gat gca  atc aga aag gct tta  tat gac gag gtg gac  aag      8394
Leu Lys Asp Ala  Ile Arg Lys Ala Leu  Tyr Asp Glu Val Asp  Lys
            2455                2460                2465

gtg gag aat tca  gag ttt cga gag gca  atc ctg ttg tcc aag  acc      8439
Val Glu Asn Ser  Glu Phe Arg Glu Ala  Ile Leu Leu Ser Lys  Thr
            2470                2475                2480

cat aga gat aat  ttt ata ctc ttc tta  aca tct gtt gag cct  ctg      8484
His Arg Asp Asn  Phe Ile Leu Phe Leu  Thr Ser Val Glu Pro  Leu
            2485                2490                2495

ttt cct cga ttt  ctc agt gag cta ttc  agt tcg tct ttt ttg  gga      8529
Phe Pro Arg Phe  Leu Ser Glu Leu Phe  Ser Ser Ser Phe Leu  Gly
            2500                2505                2510

atc ccc gag tca  atc att gga ttg ata  caa aac tcc cga acg  ata      8574
Ile Pro Glu Ser  Ile Ile Gly Leu Ile  Gln Asn Ser Arg Thr  Ile
            2515                2520                2525

aga agg cag ttt  aga aag agt ctc tca  aaa act tta gaa gaa  tcc      8619
```

-continued

```
Arg Arg Gln Phe Arg Lys Ser Leu Ser Lys Thr Leu Glu Glu Ser
            2530                2535                2540

ttc tac aac tca gag atc cac ggg att agt cgg atg acc cag aca      8664
Phe Tyr Asn Ser Glu Ile His Gly Ile Ser Arg Met Thr Gln Thr
            2545                2550                2555

cct cag agg gtt ggg ggg gtg tgg cct tgc tct tca gag agg gca      8709
Pro Gln Arg Val Gly Gly Val Trp Pro Cys Ser Ser Glu Arg Ala
            2560                2565                2570

gat cta ctt agg gag atc tct tgg gga aga aaa gtg gta ggc acg      8754
Asp Leu Leu Arg Glu Ile Ser Trp Gly Arg Lys Val Val Gly Thr
            2575                2580                2585

aca gtt cct cac cct tct gag atg ttg ggg tta ctt ccc aag tcc      8799
Thr Val Pro His Pro Ser Glu Met Leu Gly Leu Leu Pro Lys Ser
            2590                2595                2600

tct att tct tgc act tgt gga gca aca gga gga ggc aat cct aga      8844
Ser Ile Ser Cys Thr Cys Gly Ala Thr Gly Gly Gly Asn Pro Arg
            2605                2610                2615

gtt tct gta tca gta ctc ccg tcc ttt gat cag tca ttt ttt tca      8889
Val Ser Val Ser Val Leu Pro Ser Phe Asp Gln Ser Phe Phe Ser
            2620                2625                2630

cga ggc ccc cta aag ggg tac ttg ggc tcg tcc acc tct atg tcg      8934
Arg Gly Pro Leu Lys Gly Tyr Leu Gly Ser Ser Thr Ser Met Ser
            2635                2640                2645

acc cag cta ttc cat gca tgg gaa aaa gtc act aat gtt cat gtg      8979
Thr Gln Leu Phe His Ala Trp Glu Lys Val Thr Asn Val His Val
            2650                2655                2660

gtg aag aga gct cta tcg tta aaa gaa tct ata aac tgg ttc att      9024
Val Lys Arg Ala Leu Ser Leu Lys Glu Ser Ile Asn Trp Phe Ile
            2665                2670                2675

act aga gat tcc aac ttg gct caa gct cta att agg aac att atg      9069
Thr Arg Asp Ser Asn Leu Ala Gln Ala Leu Ile Arg Asn Ile Met
            2680                2685                2690

tct ctg aca ggc cct gat ttc cct cta gag gag gcc cct gtc ttc      9114
Ser Leu Thr Gly Pro Asp Phe Pro Leu Glu Glu Ala Pro Val Phe
            2695                2700                2705

aaa agg acg ggg tca gcc ttg cat agg ttc aag tct gcc aga tac      9159
Lys Arg Thr Gly Ser Ala Leu His Arg Phe Lys Ser Ala Arg Tyr
            2710                2715                2720

agc gaa gga ggg tat tct tct gtc tgc ccg aac ctc ctc tct cat      9204
Ser Glu Gly Gly Tyr Ser Ser Val Cys Pro Asn Leu Leu Ser His
            2725                2730                2735

att tct gtt agt aca gac acc atg tct gat ttg acc caa gac ggg      9249
Ile Ser Val Ser Thr Asp Thr Met Ser Asp Leu Thr Gln Asp Gly
            2740                2745                2750

aag aac tac gat ttc atg ttc cag cca ttg atg ctt tat gca cag      9294
Lys Asn Tyr Asp Phe Met Phe Gln Pro Leu Met Leu Tyr Ala Gln
            2755                2760                2765

aca tgg aca tca gag ctg gta cag aga gac aca agg cta aga gac      9339
Thr Trp Thr Ser Glu Leu Val Gln Arg Asp Thr Arg Leu Arg Asp
            2770                2775                2780

tct acg ttt cat tgg cac ctc cga tgc aac agg tgt gtg aga ccc      9384
Ser Thr Phe His Trp His Leu Arg Cys Asn Arg Cys Val Arg Pro
            2785                2790                2795

att gac gac gtg acc ctg gag acc tct cag atc ttc gag ttt ccg      9429
Ile Asp Asp Val Thr Leu Glu Thr Ser Gln Ile Phe Glu Phe Pro
            2800                2805                2810

gat gtg tcg aaa aga ata tcc aga atg gtt tct ggg gct gtg cct      9474
Asp Val Ser Lys Arg Ile Ser Arg Met Val Ser Gly Ala Val Pro
            2815                2820                2825
```

```
cac ttc cag agg  ctt ccc gat atc cgt  ctg aga cca gga gat  ttt      9519
His Phe Gln Arg  Leu Pro Asp Ile Arg  Leu Arg Pro Gly Asp  Phe
            2830                 2835                 2840

gaa tct cta agc  ggt aga gaa aag tct  cac cat atc gga tca  gct      9564
Glu Ser Leu Ser  Gly Arg Glu Lys Ser  His His Ile Gly Ser  Ala
            2845                 2850                 2855

cag ggg ctc tta  tac tca atc tta gtg  gca att cac gac tca  gga      9609
Gln Gly Leu Leu  Tyr Ser Ile Leu Val  Ala Ile His Asp Ser  Gly
            2860                 2865                 2870

tac aat gat gga  acc atc ttc cct gtc  aac ata tac gac aag  gtt      9654
Tyr Asn Asp Gly  Thr Ile Phe Pro Val  Asn Ile Tyr Asp Lys  Val
            2875                 2880                 2885

tcc cct aga gac  tat ttg aga ggg ctc  gca agg gga gta ttg  ata      9699
Ser Pro Arg Asp  Tyr Leu Arg Gly Leu  Ala Arg Gly Val Leu  Ile
            2890                 2895                 2900

gga tcc tcg att  tgc ttc ttg aca aga  atg aca aat atc aat  att      9744
Gly Ser Ser Ile  Cys Phe Leu Thr Arg  Met Thr Asn Ile Asn  Ile
            2905                 2910                 2915

aat aga cct ctt  gaa ttg atc tca ggg  gta atc tca tat att  ctc      9789
Asn Arg Pro Leu  Glu Leu Ile Ser Gly  Val Ile Ser Tyr Ile  Leu
            2920                 2925                 2930

ctg agg cta gat  aac cat ccc tcc ttg  tac ata atg ctc aga  gaa      9834
Leu Arg Leu Asp  Asn His Pro Ser Leu  Tyr Ile Met Leu Arg  Glu
            2935                 2940                 2945

ccg tct ctt aga  gga gag ata ttt tct  atc cct cag aaa atc  ccc      9879
Pro Ser Leu Arg  Gly Glu Ile Phe Ser  Ile Pro Gln Lys Ile  Pro
            2950                 2955                 2960

gcc gct tat cca  acc act atg aaa gaa  ggc aac aga tca atc  ttg      9924
Ala Ala Tyr Pro  Thr Thr Met Lys Glu  Gly Asn Arg Ser Ile  Leu
            2965                 2970                 2975

tgt tat ctc caa  cat gtg cta cgc tat  gag cga gag ata atc  acg      9969
Cys Tyr Leu Gln  His Val Leu Arg Tyr  Glu Arg Glu Ile Ile  Thr
            2980                 2985                 2990

gcg tct cca gag  aat gac tgg cta tgg  atc ttt tca gac ttt  aga     10014
Ala Ser Pro Glu  Asn Asp Trp Leu Trp  Ile Phe Ser Asp Phe  Arg
            2995                 3000                 3005

agt gcc aaa atg  acg tac cta acc ctc  att act tac cag tct  cat     10059
Ser Ala Lys Met  Thr Tyr Leu Thr Leu  Ile Thr Tyr Gln Ser  His
            3010                 3015                 3020

ctt cta ctc cag  agg gtt gag aga aac  cta tct aag agt atg  aga     10104
Leu Leu Leu Gln  Arg Val Glu Arg Asn  Leu Ser Lys Ser Met  Arg
            3025                 3030                 3035

gat aac ctg cga  caa ttg agt tcc ttg  atg agg cag gtg ctg  ggc     10149
Asp Asn Leu Arg  Gln Leu Ser Ser Leu  Met Arg Gln Val Leu  Gly
            3040                 3045                 3050

ggg cac gga gaa  gat acc tta gag tca  gac gac aac att caa  cga     10194
Gly His Gly Glu  Asp Thr Leu Glu Ser  Asp Asp Asn Ile Gln  Arg
            3055                 3060                 3065

ctg cta aaa gac  tct tta cga agg aca  aga tgg gtg gat caa  gag     10239
Leu Leu Lys Asp  Ser Leu Arg Arg Thr  Arg Trp Val Asp Gln  Glu
            3070                 3075                 3080

gtg cgc cat gca  gct aga acc atg act  gga gat tac agc ccc  aac     10284
Val Arg His Ala  Ala Arg Thr Met Thr  Gly Asp Tyr Ser Pro  Asn
            3085                 3090                 3095

aag aag gtg tcc  cgt aag gta gga tgt  tca gaa tgg gtc tgc  tct     10329
Lys Lys Val Ser  Arg Lys Val Gly Cys  Ser Glu Trp Val Cys  Ser
            3100                 3105                 3110

gct caa cag gtt  gca gtc tct acc tca  gca aac ccg gcc cct  gtc     10374
Ala Gln Gln Val  Ala Val Ser Thr Ser  Ala Asn Pro Ala Pro  Val
            3115                 3120                 3125
```

```
tcg gag ctt gac  ata agg gcc ctc tct  aag agg ttc cag aac  cct     10419
Ser Glu Leu Asp  Ile Arg Ala Leu Ser  Lys Arg Phe Gln Asn  Pro
            3130                 3135                 3140

ttg atc tcg ggc  ttg aga gtg gtt cag  tgg gca acc ggt gct  cat     10464
Leu Ile Ser Gly  Leu Arg Val Val Gln  Trp Ala Thr Gly Ala  His
            3145                 3150                 3155

tat aag ctt aag  cct att cta gat gat  ctc aat gtt ttc cca  tct     10509
Tyr Lys Leu Lys  Pro Ile Leu Asp Asp  Leu Asn Val Phe Pro  Ser
            3160                 3165                 3170

ctc tgc ctt gta  gtt ggg gac ggg tca  ggg ggg ata tca agg  gca     10554
Leu Cys Leu Val  Val Gly Asp Gly Ser  Gly Gly Ile Ser Arg  Ala
            3175                 3180                 3185

gtc ctc aac atg  ttt cca gat gcc aag  ctt gtg ttc aac agt  ctc     10599
Val Leu Asn Met  Phe Pro Asp Ala Lys  Leu Val Phe Asn Ser  Leu
            3190                 3195                 3200

tta gag gtg aat  gac ctg atg gct tcc  gga aca cat cca ctg  cct     10644
Leu Glu Val Asn  Asp Leu Met Ala Ser  Gly Thr His Pro Leu  Pro
            3205                 3210                 3215

cct tca gca atc  atg agg gga gga aat  gat atc gtc tcc aga  gtg     10689
Pro Ser Ala Ile  Met Arg Gly Gly Asn  Asp Ile Val Ser Arg  Val
            3220                 3225                 3230

ata gat ttt gac  tca atc tgg gaa aaa  ccg tcc gac ttg aga  aac     10734
Ile Asp Phe Asp  Ser Ile Trp Glu Lys  Pro Ser Asp Leu Arg  Asn
            3235                 3240                 3245

ttg gca acc tgg  aaa tac ttc cag tca  gtc caa aag cag gtc  aac     10779
Leu Ala Thr Trp  Lys Tyr Phe Gln Ser  Val Gln Lys Gln Val  Asn
            3250                 3255                 3260

atg tcc tat gac  ctc att att tgc gat  gca gaa gtt act gac  att     10824
Met Ser Tyr Asp  Leu Ile Ile Cys Asp  Ala Glu Val Thr Asp  Ile
            3265                 3270                 3275

gca tct atc aac  cgg ata acc ctg tta  atg tcc gat ttt gca  ttg     10869
Ala Ser Ile Asn  Arg Ile Thr Leu Leu  Met Ser Asp Phe Ala  Leu
            3280                 3285                 3290

tct ata gat gga  cca ctc tat ttg gtc  ttc aaa act tat ggg  act     10914
Ser Ile Asp Gly  Pro Leu Tyr Leu Val  Phe Lys Thr Tyr Gly  Thr
            3295                 3300                 3305

atg cta gta aat  cca aac tac aag gct  att caa cac ctg tca  aga     10959
Met Leu Val Asn  Pro Asn Tyr Lys Ala  Ile Gln His Leu Ser  Arg
            3310                 3315                 3320

gcg ttc ccc tcg  gtc aca ggg ttt atc  acc caa gta act tcg  tct     11004
Ala Phe Pro Ser  Val Thr Gly Phe Ile  Thr Gln Val Thr Ser  Ser
            3325                 3330                 3335

ttt tca tct gag  ctc tac ctc cga ttc  tcc aaa cga ggg aag  ttt     11049
Phe Ser Ser Glu  Leu Tyr Leu Arg Phe  Ser Lys Arg Gly Lys  Phe
            3340                 3345                 3350

ttc aga gat gct  gag tac ttg acc tct  tcc acc ctt cga gaa  atg     11094
Phe Arg Asp Ala  Glu Tyr Leu Thr Ser  Ser Thr Leu Arg Glu  Met
            3355                 3360                 3365

agc ctt gtg tta  ttc aat tgt agc agc  ccc aag agt gag atg  cag     11139
Ser Leu Val Leu  Phe Asn Cys Ser Ser  Pro Lys Ser Glu Met  Gln
            3370                 3375                 3380

aga gct cgt tcc  ttg aac tat cag gat  ctt gtg aga gga ttt  cct     11184
Arg Ala Arg Ser  Leu Asn Tyr Gln Asp  Leu Val Arg Gly Phe  Pro
            3385                 3390                 3395

gaa gaa atc ata  tca aat cct tac aat  gag atg atc ata act  ctg     11229
Glu Glu Ile Ile  Ser Asn Pro Tyr Asn  Glu Met Ile Ile Thr  Leu
            3400                 3405                 3410

att gac agt gat  gta gaa tct ttt cta  gtc cac aag atg gtt  gat     11274
Ile Asp Ser Asp  Val Glu Ser Phe Leu  Val His Lys Met Val  Asp
```

```
            3415                3420                3425

gat ctt gag tta  cag agg gga act ctg  tct aaa gtg gct atc  att     11319
Asp Leu Glu Leu  Gln Arg Gly Thr Leu  Ser Lys Val Ala Ile  Ile
            3430                3435                3440

ata gcc atc atg  ata gtt ttc tcc aac  aga gtc ttc aac gtt  tcc     11364
Ile Ala Ile Met  Ile Val Phe Ser Asn  Arg Val Phe Asn Val  Ser
            3445                3450                3455

aaa ccc cta act  gac ccc ttg ttc tat  cca ccg tct gat ccc  aaa     11409
Lys Pro Leu Thr  Asp Pro Leu Phe Tyr  Pro Pro Ser Asp Pro  Lys
            3460                3465                3470

atc ctg agg cac  ttc aac ata tgt tgc  agt act atg atg tat  cta     11454
Ile Leu Arg His  Phe Asn Ile Cys Cys  Ser Thr Met Met Tyr  Leu
            3475                3480                3485

tct act gct tta  ggt gac gtc cct agc  ttc gca aga ctt cac  gac     11499
Ser Thr Ala Leu  Gly Asp Val Pro Ser  Phe Ala Arg Leu His  Asp
            3490                3495                3500

ctg tat aac aga  cct ata act tat tac  ttc aga aag caa ttc  att     11544
Leu Tyr Asn Arg  Pro Ile Thr Tyr Tyr  Phe Arg Lys Gln Phe  Ile
            3505                3510                3515

cga ggg aac gtt  tat cta tct tgg agt  tgg tcc aac gac acc  tca     11589
Arg Gly Asn Val  Tyr Leu Ser Trp Ser  Trp Ser Asn Asp Thr  Ser
            3520                3525                3530

gtg ttc aaa agg  gta gcc tgt aat tct  agc ctg agt ctg tca  tct     11634
Val Phe Lys Arg  Val Ala Cys Asn Ser  Ser Leu Ser Leu Ser  Ser
            3535                3540                3545

cac tgg atc agg  ttg att tac aag ata  gtg aag act acc aga  ctc     11679
His Trp Ile Arg  Leu Ile Tyr Lys Ile  Val Lys Thr Thr Arg  Leu
            3550                3555                3560

gtt ggc agc atc  aag gat cta tcc aga  gaa gtg gaa aga cac  ctt     11724
Val Gly Ser Ile  Lys Asp Leu Ser Arg  Glu Val Glu Arg His  Leu
            3565                3570                3575

cat agg tac aac  agg tgg atc acc cta  gag gat atc aga tct  aga     11769
His Arg Tyr Asn  Arg Trp Ile Thr Leu  Glu Asp Ile Arg Ser  Arg
            3580                3585                3590

tca tcc cta cta  gac tac agt tgc ctg  tgaaccggat actcctggaa        11816
Ser Ser Leu Leu  Asp Tyr Ser Cys Leu
            3595                3600

gcctgcccat gctaagactc ttgtgtgatg tatcttgaaa aaaacaagat cctaaatctg  11876

aacctttggt tgtttgattg tttttctcat ttttgttgtt tatttgttaa gcgt        11930


<210> SEQ ID NO 2
<211> LENGTH: 450
<212> TYPE: PRT
<213> ORGANISM: Artificial Sequence
<220> FEATURE:
<223> OTHER INFORMATION: Synthetic Construct

<400> SEQUENCE: 2

Met Asp Ala Asp Lys Ile Val Phe Lys Val Asn Asn Gln Val Val Ser
1               5                   10                  15

Leu Lys Pro Glu Ile Ile Val Asp Gln His Glu Tyr Lys Tyr Pro Ala
            20                  25                  30

Ile Lys Asp Leu Lys Lys Pro Cys Ile Thr Leu Gly Lys Ala Pro Asp
        35                  40                  45

Leu Asn Lys Ala Tyr Lys Ser Val Leu Ser Gly Met Ser Ala Ala Lys
    50                  55                  60

Leu Asp Pro Asp Asp Val Cys Ser Tyr Leu Ala Ala Ala Met Gln Phe
65                  70                  75                  80
```

```
Phe Glu Gly Thr Cys Pro Glu Asp Trp Thr Ser Tyr Gly Ile Val Ile
                85                  90                  95

Ala Arg Lys Gly Asp Lys Ile Thr Pro Gly Ser Leu Val Glu Ile Lys
            100                 105                 110

Arg Thr Asp Val Glu Gly Asn Trp Ala Leu Thr Gly Gly Met Glu Leu
        115                 120                 125

Thr Arg Asp Pro Thr Val Pro Glu His Ala Ser Leu Val Gly Leu Leu
    130                 135                 140

Leu Ser Leu Tyr Arg Leu Ser Lys Ile Ser Gly Gln Asn Thr Gly Asn
145                 150                 155                 160

Tyr Lys Thr Asn Ile Ala Asp Arg Ile Glu Gln Ile Phe Glu Thr Ala
                165                 170                 175

Pro Phe Val Lys Ile Val Glu His His Thr Leu Met Thr Thr His Lys
            180                 185                 190

Met Cys Ala Asn Trp Ser Thr Ile Pro Asn Phe Arg Phe Leu Ala Gly
        195                 200                 205

Thr Tyr Asp Met Phe Phe Ser Arg Ile Glu His Leu Tyr Ser Ala Ile
    210                 215                 220

Arg Val Gly Thr Val Val Thr Ala Tyr Glu Asp Cys Ser Gly Leu Val
225                 230                 235                 240

Ser Phe Thr Gly Phe Ile Lys Gln Ile Asn Leu Thr Ala Arg Glu Ala
                245                 250                 255

Ile Leu Tyr Phe Phe His Lys Asn Phe Glu Glu Glu Ile Arg Arg Met
            260                 265                 270

Phe Glu Pro Gly Gln Glu Thr Ala Val Pro His Ser Tyr Phe Ile His
        275                 280                 285

Phe Arg Ser Leu Gly Leu Ser Gly Lys Ser Pro Tyr Ser Ser Asn Ala
    290                 295                 300

Val Gly His Val Phe Asn Leu Ile His Phe Val Gly Cys Tyr Met Gly
305                 310                 315                 320

Gln Val Arg Ser Leu Asn Ala Thr Val Ile Ala Ala Cys Ala Pro His
                325                 330                 335

Glu Met Ser Val Leu Gly Gly Tyr Leu Gly Glu Glu Phe Phe Gly Lys
            340                 345                 350

Gly Thr Phe Glu Arg Arg Phe Phe Arg Asp Glu Lys Glu Leu Gln Glu
        355                 360                 365

Tyr Glu Ala Ala Glu Leu Thr Lys Thr Asp Val Ala Leu Ala Asp Asp
    370                 375                 380

Gly Thr Val Asn Ser Asp Asp Glu Asp Tyr Phe Ser Gly Glu Thr Arg
385                 390                 395                 400

Ser Pro Glu Ala Val Tyr Thr Arg Ile Met Met Asn Gly Gly Arg Leu
                405                 410                 415

Lys Arg Ser His Ile Arg Arg Tyr Val Ser Val Ser Ser Asn His Gln
            420                 425                 430

Ala Arg Pro Asn Ser Phe Ala Glu Phe Leu Asn Lys Thr Tyr Ser Ser
        435                 440                 445

Asp Ser
    450
```

<210> SEQ ID NO 3
<211> LENGTH: 297
<212> TYPE: PRT
<213> ORGANISM: Artificial Sequence
<220> FEATURE:
<223> OTHER INFORMATION: Synthetic Construct

<400> SEQUENCE: 3

```
Met Ser Lys Ile Phe Val Asn Pro Ser Ala Ile Arg Ala Gly Leu Ala
1               5                   10                  15

Asp Leu Glu Met Ala Glu Glu Thr Val Asp Leu Ile Asn Arg Asn Ile
            20                  25                  30

Glu Asp Asn Gln Ala His Leu Gln Gly Glu Pro Ile Glu Val Asp Asn
        35                  40                  45

Leu Pro Glu Asp Met Gly Arg Leu His Leu Asp Asp Gly Lys Ser Pro
    50                  55                  60

Asn Pro Gly Glu Met Ala Lys Val Gly Glu Gly Lys Tyr Arg Glu Asp
65                  70                  75                  80

Phe Gln Met Asp Glu Gly Glu Asp Leu Ser Phe Leu Phe Gln Ser Tyr
                85                  90                  95

Leu Glu Asn Val Gly Val Gln Ile Val Arg Gln Met Arg Ser Gly Glu
            100                 105                 110

Arg Phe Leu Lys Ile Trp Ser Gln Thr Val Glu Glu Ile Ile Ser Tyr
        115                 120                 125

Val Ala Val Asn Phe Pro Asn Pro Pro Gly Lys Ser Ser Glu Asp Lys
    130                 135                 140

Ser Thr Gln Thr Thr Gly Arg Glu Leu Lys Lys Glu Thr Thr Pro Thr
145                 150                 155                 160

Pro Ser Gln Arg Glu Ser Gln Ser Ser Lys Ala Arg Met Ala Ala Gln
                165                 170                 175

Ile Ala Ser Gly Pro Pro Ala Leu Glu Trp Ser Ala Thr Asn Glu Glu
            180                 185                 190

Asp Asp Leu Ser Val Glu Ala Glu Ile Ala His Gln Ile Ala Glu Ser
        195                 200                 205

Phe Ser Lys Lys Tyr Lys Phe Pro Ser Arg Ser Ser Gly Ile Leu Leu
    210                 215                 220

Tyr Asn Phe Glu Gln Leu Lys Met Asn Leu Asp Asp Ile Val Lys Glu
225                 230                 235                 240

Ala Lys Asn Val Pro Gly Val Thr Arg Leu Ala His Asp Gly Ser Lys
                245                 250                 255

Leu Pro Leu Arg Cys Val Leu Gly Trp Val Ala Leu Ala Asn Pro Lys
            260                 265                 270

Lys Phe Gln Leu Leu Val Glu Ser Asp Lys Leu Ser Lys Ile Met Gln
        275                 280                 285

Asp Asp Leu Asn Arg Tyr Thr Ser Cys
    290                 295
```

<210> SEQ ID NO 4
<211> LENGTH: 202
<212> TYPE: PRT
<213> ORGANISM: Artificial Sequence
<220> FEATURE:
<223> OTHER INFORMATION: Synthetic Construct

<400> SEQUENCE: 4

```
Met Asn Phe Leu Arg Lys Ile Val Lys Asn Cys Arg Asp Glu Asp Thr
1               5                   10                  15

Gln Lys Pro Ser Pro Val Ser Ala Pro Leu Asp Asp Asp Asp Leu Trp
            20                  25                  30

Leu Pro Pro Pro Glu Tyr Val Pro Leu Lys Glu Leu Thr Ser Lys Lys
        35                  40                  45
```

```
Asn Met Arg Asn Phe Cys Ile Asn Gly Gly Val Lys Val Cys Ser Pro
    50                  55                  60

Asn Gly Tyr Ser Phe Arg Ile Leu Arg His Ile Leu Lys Ser Phe Asp
65                  70                  75                  80

Glu Ile Tyr Ser Gly Asn His Arg Met Ile Gly Leu Ala Lys Val Val
                85                  90                  95

Ile Gly Leu Ala Leu Ser Gly Ser Pro Val Pro Glu Gly Met Asn Trp
            100                 105                 110

Val Tyr Lys Leu Arg Arg Thr Phe Ile Phe Gln Trp Ala Asp Ser Arg
        115                 120                 125

Gly Pro Leu Glu Gly Glu Glu Leu Glu Tyr Ser Gln Glu Ile Thr Trp
    130                 135                 140

Asp Asp Asp Thr Glu Phe Val Gly Leu Gln Ile Arg Val Ile Ala Lys
145                 150                 155                 160

Gln Cys His Ile Gln Gly Arg Ile Trp Cys Ile Asn Met Asn Pro Arg
                165                 170                 175

Ala Cys Gln Leu Trp Ser Asp Met Ser Leu Gln Thr Gln Arg Ser Glu
            180                 185                 190

Glu Asp Lys Asp Ser Ser Leu Leu Leu Glu
        195                 200


<210> SEQ ID NO 5
<211> LENGTH: 524
<212> TYPE: PRT
<213> ORGANISM: Artificial Sequence
<220> FEATURE:
<223> OTHER INFORMATION: Synthetic Construct

<400> SEQUENCE: 5

Met Val Pro Gln Ala Leu Leu Phe Val Pro Leu Leu Val Phe Pro Leu
1               5                   10                  15

Cys Phe Gly Lys Phe Pro Ile Tyr Thr Ile Pro Asp Lys Leu Gly Pro
            20                  25                  30

Trp Ser Pro Ile Asp Ile His His Leu Ser Cys Pro Asn Asn Leu Val
        35                  40                  45

Val Glu Asp Glu Gly Cys Thr Asn Leu Ser Gly Phe Ser Tyr Met Glu
    50                  55                  60

Leu Lys Val Gly Tyr Ile Leu Ala Ile Lys Met Asn Gly Phe Thr Cys
65                  70                  75                  80

Thr Gly Val Val Thr Glu Ala Glu Thr Tyr Thr Asn Phe Val Gly Tyr
                85                  90                  95

Val Thr Thr Thr Phe Lys Arg Lys His Phe Arg Pro Thr Pro Asp Ala
            100                 105                 110

Cys Arg Ala Ala Tyr Asn Trp Lys Met Ala Gly Asp Pro Arg Tyr Glu
        115                 120                 125

Glu Ser Leu His Asn Pro Tyr Pro Asp Tyr His Trp Leu Arg Thr Val
    130                 135                 140

Lys Thr Thr Lys Glu Ser Leu Val Ile Ile Ser Pro Ser Val Ala Asp
145                 150                 155                 160

Leu Asp Pro Tyr Asp Arg Ser Leu His Ser Arg Val Phe Pro Ser Gly
                165                 170                 175

Lys Cys Ser Gly Val Ala Val Ser Ser Thr Tyr Cys Ser Thr Asn His
            180                 185                 190

Asp Tyr Thr Ile Trp Met Pro Glu Asn Pro Arg Leu Gly Met Ser Cys
        195                 200                 205
```

```
Asp Ile Phe Thr Asn Ser Arg Gly Lys Arg Ala Ser Lys Gly Ser Glu
    210                 215                 220

Thr Cys Gly Phe Val Asp Glu Arg Gly Leu Tyr Lys Ser Leu Lys Gly
225                 230                 235                 240

Ala Cys Lys Leu Lys Leu Cys Gly Val Leu Gly Leu Arg Leu Met Asp
                245                 250                 255

Gly Thr Trp Val Ala Met Gln Thr Ser Asn Glu Thr Lys Trp Cys Pro
            260                 265                 270

Pro Asp Gln Leu Val Asn Leu His Asp Phe Arg Ser Asp Glu Ile Glu
        275                 280                 285

His Leu Val Val Glu Glu Leu Val Arg Lys Arg Glu Glu Cys Leu Asp
    290                 295                 300

Ala Leu Glu Ser Ile Met Thr Thr Lys Ser Val Ser Phe Arg Arg Pro
305                 310                 315                 320

Ser His Leu Arg Lys Leu Val Pro Gly Phe Gly Lys Ala Tyr Thr Ile
                325                 330                 335

Phe Asn Lys Thr Leu Met Glu Ala Asp Ala His Tyr Lys Ser Val Glu
            340                 345                 350

Thr Trp Asn Glu Ile Leu Pro Ser Lys Gly Cys Leu Arg Val Gly Gly
        355                 360                 365

Arg Cys His Pro His Val Asn Gly Val Phe Phe Asn Gly Ile Ile Leu
    370                 375                 380

Gly Pro Asp Gly Asn Val Leu Ile Pro Glu Met Gln Ser Ser Leu Leu
385                 390                 395                 400

Gln Gln His Met Glu Leu Leu Glu Ser Ser Val Ile Pro Leu Val His
                405                 410                 415

Pro Leu Ala Asp Pro Ser Thr Val Phe Lys Asp Gly Asp Glu Ala Glu
            420                 425                 430

Asp Phe Val Glu Val His Leu Pro Asp Val His Asn Gln Val Ser Gly
        435                 440                 445

Val Asp Leu Gly Leu Pro Asn Trp Gly Lys Tyr Val Leu Leu Ser Ala
    450                 455                 460

Gly Ala Leu Thr Ala Leu Met Leu Ile Ile Phe Leu Met Thr Cys Cys
465                 470                 475                 480

Arg Arg Val Asn Arg Ser Glu Pro Thr Gln His Asn Leu Arg Gly Thr
                485                 490                 495

Gly Arg Glu Val Ser Val Thr Pro Gln Ser Gly Lys Ile Ile Ser Ser
            500                 505                 510

Trp Glu Ser His Lys Ser Gly Gly Glu Thr Arg Leu
        515                 520


<210> SEQ ID NO 6
<211> LENGTH: 2127
<212> TYPE: PRT
<213> ORGANISM: Artificial Sequence
<220> FEATURE:
<223> OTHER INFORMATION: Synthetic Construct

<400> SEQUENCE: 6

Met Leu Asp Pro Gly Glu Val Tyr Asp Asp Pro Ile Asp Pro Ile Glu
1               5                   10                  15

Leu Glu Asp Glu Pro Arg Gly Thr Pro Thr Val Pro Asn Ile Leu Arg
            20                  25                  30

Asn Ser Asp Tyr Asn Leu Asn Ser Pro Leu Ile Glu Asp Pro Ala Arg
        35                  40                  45
```

```
Leu Met Leu Glu Trp Leu Lys Thr Gly Asn Arg Pro Tyr Arg Met Thr
    50                  55                  60

Leu Thr Asp Asn Cys Ser Arg Ser Phe Arg Val Leu Lys Asp Tyr Phe
65                  70                  75                  80

Lys Lys Val Asp Leu Gly Ser Leu Lys Val Gly Gly Met Ala Ala Gln
                85                  90                  95

Ser Met Ile Ser Leu Trp Leu Tyr Gly Ala His Ser Glu Ser Asn Arg
            100                 105                 110

Ser Arg Arg Cys Ile Thr Asp Leu Ala His Phe Tyr Ser Lys Ser Ser
        115                 120                 125

Pro Ile Glu Lys Leu Leu Asn Leu Thr Leu Gly Asn Arg Gly Leu Arg
    130                 135                 140

Ile Pro Pro Glu Gly Val Leu Ser Cys Leu Glu Arg Val Asp Tyr Asp
145                 150                 155                 160

Asn Ala Phe Gly Arg Tyr Leu Ala Asn Thr Tyr Ser Ser Tyr Leu Phe
                165                 170                 175

Phe His Val Ile Thr Leu Tyr Met Asn Ala Leu Asp Trp Asp Glu Glu
            180                 185                 190

Lys Thr Ile Leu Ala Leu Trp Lys Asp Leu Thr Ser Val Asp Ile Gly
        195                 200                 205

Lys Asp Leu Val Lys Phe Lys Asp Gln Ile Trp Gly Leu Pro Ile Val
    210                 215                 220

Thr Lys Asp Phe Val Tyr Ser Gln Ser Ser Asn Cys Leu Phe Asp Arg
225                 230                 235                 240

Asn Tyr Thr Leu Met Leu Lys Glu Leu Phe Leu Ser Arg Phe Asn Ser
                245                 250                 255

Leu Met Val Leu Leu Ser Pro Pro Glu Pro Arg Tyr Ser Asp Asp Leu
            260                 265                 270

Ile Ser Gln Leu Cys Gln Leu Tyr Ile Ala Gly Asp Gln Val Leu Ser
        275                 280                 285

Met Cys Gly Asn Ser Gly Tyr Glu Val Ile Lys Ile Leu Glu Pro Tyr
    290                 295                 300

Val Val Asn Ser Leu Val Gln Arg Ala Glu Lys Phe Arg Pro Leu Ile
305                 310                 315                 320

His Ser Leu Gly Asp Phe Pro Val Phe Ile Lys Asp Lys Val Ser Gln
                325                 330                 335

Leu Glu Glu Thr Phe Gly Pro Cys Ala Arg Arg Phe Phe Arg Ala Leu
            340                 345                 350

Asp Gln Phe Asp Asn Ile His Asp Leu Val Phe Val Tyr Gly Cys Tyr
        355                 360                 365

Arg His Trp Gly His Pro Tyr Ile Asp Tyr Arg Lys Gly Leu Ser Lys
    370                 375                 380

Leu Tyr Asp Gln Val His Ile Lys Lys Val Ile Asp Lys Ser Tyr Gln
385                 390                 395                 400

Glu Cys Leu Ala Ser Asp Leu Ala Arg Arg Ile Leu Arg Trp Gly Phe
                405                 410                 415

Asp Lys Tyr Ser Lys Trp Tyr Leu Asp Ser Arg Phe Leu Ala Arg Asp
            420                 425                 430

His Pro Leu Thr Pro Tyr Ile Lys Thr Gln Thr Trp Pro Pro Lys His
        435                 440                 445

Ile Val Asp Leu Val Gly Asp Thr Trp His Lys Leu Pro Ile Thr Gln
    450                 455                 460

Ile Phe Glu Ile Pro Glu Ser Met Asp Pro Ser Glu Ile Leu Asp Asp
```

```
465                 470                 475                 480

Lys Ser His Ser Phe Thr Arg Thr Arg Leu Ala Ser Trp Leu Ser Glu
                485                 490                 495

Asn Arg Gly Gly Pro Val Pro Ser Glu Lys Val Ile Ile Thr Ala Leu
            500                 505                 510

Ser Lys Pro Pro Val Asn Pro Arg Glu Phe Leu Arg Ser Ile Asp Leu
        515                 520                 525

Gly Gly Leu Pro Asp Glu Asp Leu Ile Ile Gly Leu Lys Pro Lys Glu
    530                 535                 540

Arg Glu Leu Lys Ile Glu Gly Arg Phe Phe Ala Leu Met Ser Trp Asn
545                 550                 555                 560

Leu Arg Leu Tyr Phe Val Ile Thr Glu Lys Leu Leu Ala Asn Tyr Ile
                565                 570                 575

Leu Pro Leu Phe Asp Ala Leu Thr Met Thr Asp Asn Leu Asn Lys Val
            580                 585                 590

Phe Lys Lys Leu Ile Asp Arg Val Thr Gly Gln Gly Leu Leu Asp Tyr
        595                 600                 605

Ser Arg Val Thr Tyr Ala Phe His Leu Asp Tyr Glu Lys Trp Asn Asn
    610                 615                 620

His Gln Arg Leu Glu Ser Thr Glu Asp Val Phe Ser Val Leu Asp Gln
625                 630                 635                 640

Val Phe Gly Leu Lys Arg Val Phe Ser Arg Thr His Glu Phe Phe Gln
                645                 650                 655

Lys Ala Trp Ile Tyr Tyr Ser Asp Arg Ser Asp Leu Ile Gly Leu Arg
            660                 665                 670

Glu Asp Gln Ile Tyr Cys Leu Asp Ala Ser Asn Gly Pro Thr Cys Trp
        675                 680                 685

Asn Gly Gln Asp Gly Gly Leu Glu Gly Leu Arg Gln Lys Gly Trp Ser
    690                 695                 700

Leu Val Ser Leu Leu Met Ile Asp Arg Glu Ser Gln Ile Arg Asn Thr
705                 710                 715                 720

Arg Thr Lys Ile Leu Ala Gln Gly Asp Asn Gln Val Leu Cys Pro Thr
                725                 730                 735

Tyr Met Leu Ser Pro Gly Leu Ser Gln Glu Gly Leu Leu Tyr Glu Leu
            740                 745                 750

Glu Arg Ile Ser Arg Asn Ala Leu Ser Ile Tyr Arg Ala Val Glu Glu
        755                 760                 765

Gly Ala Ser Lys Leu Gly Leu Ile Ile Lys Lys Glu Glu Thr Met Cys
    770                 775                 780

Ser Tyr Asp Phe Leu Ile Tyr Gly Lys Thr Pro Leu Phe Arg Gly Asn
785                 790                 795                 800

Ile Leu Val Pro Glu Ser Lys Arg Trp Ala Arg Val Ser Cys Val Ser
                805                 810                 815

Asn Asp Gln Ile Val Asn Leu Ala Asn Ile Met Ser Thr Val Ser Thr
            820                 825                 830

Asn Ala Leu Thr Val Ala Gln His Ser Gln Ser Leu Ile Lys Pro Met
        835                 840                 845

Arg Asp Phe Leu Leu Met Ser Val Gln Ala Val Phe His Tyr Leu Leu
    850                 855                 860

Phe Ser Pro Ile Leu Lys Gly Arg Val Tyr Lys Ile Leu Ser Ala Glu
865                 870                 875                 880

Gly Asp Ser Phe Leu Leu Ala Met Ser Arg Ile Ile Tyr Leu Asp Pro
                885                 890                 895
```

-continued

```
Ser Leu Gly Gly Val Ser Gly Met Ser Leu Gly Arg Phe His Ile Arg
            900                 905                 910

Gln Phe Ser Asp Pro Val Ser Glu Gly Leu Ser Phe Trp Arg Glu Ile
        915                 920                 925

Trp Leu Ser Ser His Glu Ser Trp Ile His Ala Leu Cys Gln Glu Ala
    930                 935                 940

Gly Asn Pro Asp Leu Gly Glu Arg Thr Leu Glu Ser Phe Thr Arg Leu
945                 950                 955                 960

Leu Glu Asp Pro Thr Thr Leu Asn Ile Arg Gly Gly Ala Ser Pro Thr
                965                 970                 975

Ile Leu Leu Lys Asp Ala Ile Arg Lys Ala Leu Tyr Asp Glu Val Asp
            980                 985                 990

Lys Val Glu Asn Ser Glu Phe Arg  Glu Ala Ile Leu Leu  Ser Lys Thr
        995                 1000                 1005

His Arg  Asp Asn Phe Ile Leu  Phe Leu Thr Ser Val  Glu Pro Leu
    1010                 1015                 1020

Phe Pro  Arg Phe Leu Ser Glu  Leu Phe Ser Ser Ser  Phe Leu Gly
    1025                 1030                 1035

Ile Pro  Glu Ser Ile Ile Gly  Leu Ile Gln Asn Ser  Arg Thr Ile
    1040                 1045                 1050

Arg Arg  Gln Phe Arg Lys Ser  Leu Ser Lys Thr Leu  Glu Glu Ser
    1055                 1060                 1065

Phe Tyr  Asn Ser Glu Ile His  Gly Ile Ser Arg Met  Thr Gln Thr
    1070                 1075                 1080

Pro Gln  Arg Val Gly Gly Val  Trp Pro Cys Ser Ser  Glu Arg Ala
    1085                 1090                 1095

Asp Leu  Leu Arg Glu Ile Ser  Trp Gly Arg Lys Val  Val Gly Thr
    1100                 1105                 1110

Thr Val  Pro His Pro Ser Glu  Met Leu Gly Leu Leu  Pro Lys Ser
    1115                 1120                 1125

Ser Ile  Ser Cys Thr Cys Gly  Ala Thr Gly Gly Gly  Asn Pro Arg
    1130                 1135                 1140

Val Ser  Val Ser Val Leu Pro  Ser Phe Asp Gln Ser  Phe Phe Ser
    1145                 1150                 1155

Arg Gly  Pro Leu Lys Gly Tyr  Leu Gly Ser Ser Thr  Ser Met Ser
    1160                 1165                 1170

Thr Gln  Leu Phe His Ala Trp  Glu Lys Val Thr Asn  Val His Val
    1175                 1180                 1185

Val Lys  Arg Ala Leu Ser Leu  Lys Glu Ser Ile Asn  Trp Phe Ile
    1190                 1195                 1200

Thr Arg  Asp Ser Asn Leu Ala  Gln Ala Leu Ile Arg  Asn Ile Met
    1205                 1210                 1215

Ser Leu  Thr Gly Pro Asp Phe  Pro Leu Glu Glu Ala  Pro Val Phe
    1220                 1225                 1230

Lys Arg  Thr Gly Ser Ala Leu  His Arg Phe Lys Ser  Ala Arg Tyr
    1235                 1240                 1245

Ser Glu  Gly Gly Tyr Ser Ser  Val Cys Pro Asn Leu  Leu Ser His
    1250                 1255                 1260

Ile Ser  Val Ser Thr Asp Thr  Met Ser Asp Leu Thr  Gln Asp Gly
    1265                 1270                 1275

Lys Asn  Tyr Asp Phe Met Phe  Gln Pro Leu Met Leu  Tyr Ala Gln
    1280                 1285                 1290
```

```
Thr Trp  Thr Ser Glu Leu Val  Gln Arg Asp Thr Arg  Leu Arg Asp
    1295                 1300                 1305

Ser Thr  Phe His Trp His Leu  Arg Cys Asn Arg Cys  Val Arg Pro
    1310                 1315                 1320

Ile Asp  Asp Val Thr Leu Glu  Thr Ser Gln Ile Phe  Glu Phe Pro
    1325                 1330                 1335

Asp Val  Ser Lys Arg Ile Ser  Arg Met Val Ser Gly  Ala Val Pro
    1340                 1345                 1350

His Phe  Gln Arg Leu Pro Asp  Ile Arg Leu Arg Pro  Gly Asp Phe
    1355                 1360                 1365

Glu Ser  Leu Ser Gly Arg Glu  Lys Ser His His Ile  Gly Ser Ala
    1370                 1375                 1380

Gln Gly  Leu Leu Tyr Ser Ile  Leu Val Ala Ile His  Asp Ser Gly
    1385                 1390                 1395

Tyr Asn  Asp Gly Thr Ile Phe  Pro Val Asn Ile Tyr  Asp Lys Val
    1400                 1405                 1410

Ser Pro  Arg Asp Tyr Leu Arg  Gly Leu Ala Arg Gly  Val Leu Ile
    1415                 1420                 1425

Gly Ser  Ser Ile Cys Phe Leu  Thr Arg Met Thr Asn  Ile Asn Ile
    1430                 1435                 1440

Asn Arg  Pro Leu Glu Leu Ile  Ser Gly Val Ile Ser  Tyr Ile Leu
    1445                 1450                 1455

Leu Arg  Leu Asp Asn His Pro  Ser Leu Tyr Ile Met  Leu Arg Glu
    1460                 1465                 1470

Pro Ser  Leu Arg Gly Glu Ile  Phe Ser Ile Pro Gln  Lys Ile Pro
    1475                 1480                 1485

Ala Ala  Tyr Pro Thr Thr Met  Lys Glu Gly Asn Arg  Ser Ile Leu
    1490                 1495                 1500

Cys Tyr  Leu Gln His Val Leu  Arg Tyr Glu Arg Glu  Ile Ile Thr
    1505                 1510                 1515

Ala Ser  Pro Glu Asn Asp Trp  Leu Trp Ile Phe Ser  Asp Phe Arg
    1520                 1525                 1530

Ser Ala  Lys Met Thr Tyr Leu  Thr Leu Ile Thr Tyr  Gln Ser His
    1535                 1540                 1545

Leu Leu  Leu Gln Arg Val Glu  Arg Asn Leu Ser Lys  Ser Met Arg
    1550                 1555                 1560

Asp Asn  Leu Arg Gln Leu Ser  Ser Leu Met Arg Gln  Val Leu Gly
    1565                 1570                 1575

Gly His  Gly Glu Asp Thr Leu  Glu Ser Asp Asp Asn  Ile Gln Arg
    1580                 1585                 1590

Leu Leu  Lys Asp Ser Leu Arg  Arg Thr Arg Trp Val  Asp Gln Glu
    1595                 1600                 1605

Val Arg  His Ala Ala Arg Thr  Met Thr Gly Asp Tyr  Ser Pro Asn
    1610                 1615                 1620

Lys Lys  Val Ser Arg Lys Val  Gly Cys Ser Glu Trp  Val Cys Ser
    1625                 1630                 1635

Ala Gln  Gln Val Ala Val Ser  Thr Ser Ala Asn Pro  Ala Pro Val
    1640                 1645                 1650

Ser Glu  Leu Asp Ile Arg Ala  Leu Ser Lys Arg Phe  Gln Asn Pro
    1655                 1660                 1665

Leu Ile  Ser Gly Leu Arg Val  Val Gln Trp Ala Thr  Gly Ala His
    1670                 1675                 1680

Tyr Lys  Leu Lys Pro Ile Leu  Asp Asp Leu Asn Val  Phe Pro Ser
```

```
    1685                1690                1695

Leu Cys  Leu Val Val Gly Asp  Gly Ser Gly Gly Ile  Ser Arg Ala
    1700                1705                1710

Val Leu  Asn Met Phe Pro Asp  Ala Lys Leu Val Phe  Asn Ser Leu
    1715                1720                1725

Leu Glu  Val Asn Asp Leu Met  Ala Ser Gly Thr His  Pro Leu Pro
    1730                1735                1740

Pro Ser  Ala Ile Met Arg Gly  Gly Asn Asp Ile Val  Ser Arg Val
    1745                1750                1755

Ile Asp  Phe Asp Ser Ile Trp  Glu Lys Pro Ser Asp  Leu Arg Asn
    1760                1765                1770

Leu Ala  Thr Trp Lys Tyr Phe  Gln Ser Val Gln Lys  Gln Val Asn
    1775                1780                1785

Met Ser  Tyr Asp Leu Ile Ile  Cys Asp Ala Glu Val  Thr Asp Ile
    1790                1795                1800

Ala Ser  Ile Asn Arg Ile Thr  Leu Leu Met Ser Asp  Phe Ala Leu
    1805                1810                1815

Ser Ile  Asp Gly Pro Leu Tyr  Leu Val Phe Lys Thr  Tyr Gly Thr
    1820                1825                1830

Met Leu  Val Asn Pro Asn Tyr  Lys Ala Ile Gln His  Leu Ser Arg
    1835                1840                1845

Ala Phe  Pro Ser Val Thr Gly  Phe Ile Thr Gln Val  Thr Ser Ser
    1850                1855                1860

Phe Ser  Ser Glu Leu Tyr Leu  Arg Phe Ser Lys Arg  Gly Lys Phe
    1865                1870                1875

Phe Arg  Asp Ala Glu Tyr Leu  Thr Ser Ser Thr Leu  Arg Glu Met
    1880                1885                1890

Ser Leu  Val Leu Phe Asn Cys  Ser Ser Pro Lys Ser  Glu Met Gln
    1895                1900                1905

Arg Ala  Arg Ser Leu Asn Tyr  Gln Asp Leu Val Arg  Gly Phe Pro
    1910                1915                1920

Glu Glu  Ile Ile Ser Asn Pro  Tyr Asn Glu Met Ile  Ile Thr Leu
    1925                1930                1935

Ile Asp  Ser Asp Val Glu Ser  Phe Leu Val His Lys  Met Val Asp
    1940                1945                1950

Asp Leu  Glu Leu Gln Arg Gly  Thr Leu Ser Lys Val  Ala Ile Ile
    1955                1960                1965

Ile Ala  Ile Met Ile Val Phe  Ser Asn Arg Val Phe  Asn Val Ser
    1970                1975                1980

Lys Pro  Leu Thr Asp Pro Leu  Phe Tyr Pro Pro Ser  Asp Pro Lys
    1985                1990                1995

Ile Leu  Arg His Phe Asn Ile  Cys Cys Ser Thr Met  Met Tyr Leu
    2000                2005                2010

Ser Thr  Ala Leu Gly Asp Val  Pro Ser Phe Ala Arg  Leu His Asp
    2015                2020                2025

Leu Tyr  Asn Arg Pro Ile Thr  Tyr Tyr Phe Arg Lys  Gln Phe Ile
    2030                2035                2040

Arg Gly  Asn Val Tyr Leu Ser  Trp Ser Trp Ser Asn  Asp Thr Ser
    2045                2050                2055

Val Phe  Lys Arg Val Ala Cys  Asn Ser Ser Leu Ser  Leu Ser Ser
    2060                2065                2070

His Trp  Ile Arg Leu Ile Tyr  Lys Ile Val Lys Thr  Thr Arg Leu
    2075                2080                2085
```

```
Val Gly  Ser Ile Lys Asp Leu  Ser Arg Glu Val Glu  Arg His Leu
    2090                 2095                 2100

His Arg  Tyr Asn Arg Trp Ile  Thr Leu Glu Asp Ile  Arg Ser Arg
    2105                 2110                 2115

Ser Ser  Leu Leu Asp Tyr Ser  Cys Leu
    2120                 2125


<210> SEQ ID NO 7
<211> LENGTH: 524
<212> TYPE: PRT
<213> ORGANISM: Rabies virus ERA strain

<400> SEQUENCE: 7

Met Val Pro Gln Ala Leu Leu Phe Val Pro Leu Leu Val Phe Pro Leu
1               5                   10                  15

Cys Phe Gly Lys Phe Pro Ile Tyr Thr Ile Pro Asp Lys Leu Gly Pro
            20                  25                  30

Trp Ser Pro Ile Asp Ile His His Leu Ser Cys Pro Asn Asn Leu Val
        35                  40                  45

Val Glu Asp Glu Gly Cys Thr Asn Leu Ser Gly Phe Ser Tyr Met Glu
    50                  55                  60

Leu Lys Val Gly Tyr Ile Leu Ala Ile Lys Met Asn Gly Phe Thr Cys
65                  70                  75                  80

Thr Gly Val Val Thr Glu Ala Glu Thr Tyr Thr Asn Phe Val Gly Tyr
                85                  90                  95

Val Thr Thr Thr Phe Lys Arg Lys His Phe Arg Pro Thr Pro Asp Ala
            100                 105                 110

Cys Arg Ala Ala Tyr Asn Trp Lys Met Ala Gly Asp Pro Arg Tyr Glu
        115                 120                 125

Glu Ser Leu His Asn Pro Tyr Pro Asp Tyr His Trp Leu Arg Thr Val
    130                 135                 140

Lys Thr Thr Lys Glu Ser Leu Val Ile Ile Ser Pro Ser Val Ala Asp
145                 150                 155                 160

Leu Asp Pro Tyr Asp Arg Ser Leu His Ser Arg Val Phe Pro Ser Gly
                165                 170                 175

Lys Cys Ser Gly Val Ala Val Ser Ser Thr Tyr Cys Ser Thr Asn His
            180                 185                 190

Asp Tyr Thr Ile Trp Met Pro Glu Asn Pro Arg Leu Gly Met Ser Cys
        195                 200                 205

Asp Ile Phe Thr Asn Ser Arg Gly Lys Arg Ala Ser Lys Gly Ser Glu
    210                 215                 220

Thr Cys Gly Phe Val Asp Glu Arg Gly Leu Tyr Lys Ser Leu Lys Gly
225                 230                 235                 240

Ala Cys Lys Leu Lys Leu Cys Gly Val Leu Gly Leu Arg Leu Met Asp
                245                 250                 255

Gly Thr Trp Val Ala Met Gln Thr Ser Asn Glu Thr Lys Trp Cys Pro
            260                 265                 270

Pro Asp Gln Leu Val Asn Leu His Asp Phe Arg Ser Asp Glu Ile Glu
        275                 280                 285

His Leu Val Val Glu Glu Leu Val Arg Lys Arg Glu Glu Cys Leu Asp
    290                 295                 300

Ala Leu Glu Ser Ile Met Thr Thr Lys Ser Val Ser Phe Arg Arg Pro
305                 310                 315                 320

Ser His Leu Arg Lys Leu Val Pro Gly Phe Gly Lys Ala Tyr Thr Ile
```

```
                325                 330                 335

Phe Asn Lys Thr Leu Met Glu Ala Asp Ala His Tyr Lys Ser Val Arg
            340                 345                 350

Thr Trp Asn Glu Ile Leu Pro Ser Lys Gly Cys Leu Arg Val Gly Gly
        355                 360                 365

Arg Cys His Pro His Val Asn Gly Val Phe Phe Asn Gly Ile Ile Leu
    370                 375                 380

Gly Pro Asp Gly Asn Val Leu Ile Pro Glu Met Gln Ser Ser Leu Leu
385                 390                 395                 400

Gln Gln His Met Glu Leu Leu Glu Ser Ser Val Ile Pro Leu Val His
                405                 410                 415

Pro Leu Ala Asp Pro Ser Thr Val Phe Lys Asp Gly Asp Glu Ala Glu
            420                 425                 430

Asp Phe Val Glu Val His Leu Pro Asp Val His Asn Gln Val Ser Gly
        435                 440                 445

Val Asp Leu Gly Leu Pro Asn Trp Gly Lys Tyr Val Leu Leu Ser Ala
    450                 455                 460

Gly Ala Leu Thr Ala Leu Met Leu Ile Ile Phe Leu Met Thr Cys Cys
465                 470                 475                 480

Arg Arg Val Asn Arg Ser Glu Pro Thr Gln His Asn Leu Arg Gly Thr
                485                 490                 495

Gly Arg Glu Val Ser Val Thr Pro Gln Ser Gly Lys Ile Ile Ser Ser
            500                 505                 510

Trp Glu Ser His Lys Ser Gly Gly Glu Thr Arg Leu
        515                 520


<210> SEQ ID NO 8
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 8

ccgggtacca cgcttaacaa ccagatcaaa ga                                   32


<210> SEQ ID NO 9
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 9

taggtcgctt gctaagcact cctggtagga c                                    31


<210> SEQ ID NO 10
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 10

gtcctaccag gagtgcttag caagcgacct a                                    31


<210> SEQ ID NO 11
<211> LENGTH: 34
<212> TYPE: DNA
<213> ORGANISM: Artificial Sequence
```

```
<220> FEATURE:
<223> OTHER INFORMATION: Synthetic oligonucleotide

<400> SEQUENCE: 11

aaaactgcag acgcttaaca aataaacaac aaaa                                  34


<210> SEQ ID NO 12
<211> LENGTH: 79
<212> TYPE: DNA
<213> ORGANISM: Artificial Sequence
<220> FEATURE:
<223> OTHER INFORMATION: Synthetic oligonucleotide

<400> SEQUENCE: 12

caaggctagc tgttaagcgt ctgatgagtc cgtgaggacg aaactatagg aaaggaattc     60

ctatagtcgg taccacgct                                                   79


<210> SEQ ID NO 13
<211> LENGTH: 79
<212> TYPE: DNA
<213> ORGANISM: Artificial Sequence
<220> FEATURE:
<223> OTHER INFORMATION: Synthetic oligonucleotide

<400> SEQUENCE: 13

agcgtggtac cgactatagg aattcctttc ctatagtttc gtcctcacgg actcatcaga     60

cgcttaacag ctagccttg                                                   79


<210> SEQ ID NO 14
<211> LENGTH: 108
<212> TYPE: DNA
<213> ORGANISM: Artificial Sequence
<220> FEATURE:
<223> OTHER INFORMATION: Synthetic oligonucleotide

<400> SEQUENCE: 14

gacctgcagg ggtcggcatg gcatctccac ctcctcgcgg tccgacctgg gcatccgaag     60

gaggacgcac gtccactcgg atggctaagg gagggcgcgg ccgcactc                  108


<210> SEQ ID NO 15
<211> LENGTH: 108
<212> TYPE: DNA
<213> ORGANISM: Artificial Sequence
<220> FEATURE:
<223> OTHER INFORMATION: Synthetic oligonucleotide

<400> SEQUENCE: 15

gagtgcggcc gcgccctccc ttagccatcc gagtggacgt gcgtcctcct tcggatgccc     60

aggtcggacc gcgaggaggt ggagatgcca tgccgacccc tgcaggtc                  108


<210> SEQ ID NO 16
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 16

accaccatgg atgccgacaa gattg                                            25


<210> SEQ ID NO 17
<211> LENGTH: 33
<212> TYPE: DNA
```

<213> ORGANISM: Artificial Sequence
<220> FEATURE:
<223> OTHER INFORMATION: Synthetic oligonucleotide

<400> SEQUENCE: 17
ggcccatggt tatgagtcac tcgaatatgt ctt 33

<210> SEQ ID NO 18
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 18
ttggtaccac catgagcaag atctttgtca atc 33

<210> SEQ ID NO 19
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 19
ggagaggaat tcttagcaag atgtatagcg attc 34

<210> SEQ ID NO 20
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 20
ttggtaccac catggttcct caggctctcc tg 32

<210> SEQ ID NO 21
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 21
aaaactgcag tcacagtctg gtctcacccc cac 33

<210> SEQ ID NO 22
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 22
accgctagca ccaccatgct cgatcctgga gaggtc 36

<210> SEQ ID NO 23
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 23
aaaactgcag tcacaggcaa ctgtagtcta gtag 34

<210> SEQ ID NO 24
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 24
tcgctagcac caccatgaac acgattaaca tcgctaag 38

<210> SEQ ID NO 25
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 25
gatgaattct tacgcgaacg cgaagtccga ctc 33

<210> SEQ ID NO 26
<211> LENGTH: 63
<212> TYPE: DNA
<213> ORGANISM: Artificial Sequence
<220> FEATURE:
<223> OTHER INFORMATION: Synthetic oligonucleotide

<400> SEQUENCE: 26
tcgctagcca ccatgccaaa aaagaagaga aaggtagaaa acacgattaa catcgctaag 60
aac 63

<210> SEQ ID NO 27
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 27
aaaactgcag gccaccatgg gcgtgatcaa g 31

<210> SEQ ID NO 28
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 28
ccgctcggta cctattagcc ggcctggcgg g 31

<210> SEQ ID NO 29
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 29
ccctctgcag tttggtaccg tcgagaaaaa aacattagat cagaag 46

<210> SEQ ID NO 30
<211> LENGTH: 24
<212> TYPE: DNA

<213> ORGANISM: Artificial Sequence
<220> FEATURE:
<223> OTHER INFORMATION: Synthetic oligonucleotide

<400> SEQUENCE: 30
atgaactttc tacgtaagat agtg 24

<210> SEQ ID NO 31
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 31
caaactgcag aggggtgtta gtttttttca aaaagaaccc cccaag 46

<210> SEQ ID NO 32
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 32
caaactgcag aggggtgtta gtttttttca catccaagag gatc 44

<210> SEQ ID NO 33
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 33
cctctgcagt ttggtacctt gaaaaaaacc tgggttcaat ag 42

<210> SEQ ID NO 34
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 34
ctcactacaa gtcagtcgag acttggaatg agatc 35

<210> SEQ ID NO 35
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 35
gactgacttt gagtgagcat cggcttccat caagg 35

<210> SEQ ID NO 36
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 36
ccaaactgca gcgaaaggag gggtgttagt ttttttcatg atgaaccccc caaggggagg 60

<210> SEQ ID NO 37
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 37
gactcactat agggagaccc aagctggcta gctgttaag 39

<210> SEQ ID NO 38
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 38
ccaaactgca gcgaaaggag ggtgttagt tttttcatg ttgactttag gacatctcgg 60

<210> SEQ ID NO 39
<211> LENGTH: 61
<212> TYPE: DNA
<213> ORGANISM: Artificial Sequence
<220> FEATURE:
<223> OTHER INFORMATION: Synthetic oligonucleotide

<400> SEQUENCE: 39
cctttcgctg cagtttggta ccgtcgagaa aaaaacaggc aacaccactg ataaaatgaa 60
c 61

<210> SEQ ID NO 40
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 40
cctccccttc aagagggccc ctggaatcag 30

<210> SEQ ID NO 41
<211> LENGTH: 46
<212> TYPE: DNA
<213> ORGANISM: Artificial Sequence
<220> FEATURE:
<223> OTHER INFORMATION: Synthetic oligonucleotide

<400> SEQUENCE: 41
ctaacacccc tcctttcgct gcagtttggt accgtcgaga aaaaaa 46

<210> SEQ ID NO 42
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 42
tttttttgat tgtggggagg aaagcgacgt caaaccatgg cagctctttt ttt 53

<210> SEQ ID NO 43
<211> LENGTH: 37
<212> TYPE: DNA

```
<213> ORGANISM: Artificial Sequence
<220> FEATURE:
<223> OTHER INFORMATION: Synthetic oligonucleotide

<400> SEQUENCE: 43

cgactgcaga tgaatatacc ttgctttgtt gtgattc                           37


<210> SEQ ID NO 44
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 44

cgtggtacct catgtacctg gaagcccttt ataggactc                         39


<210> SEQ ID NO 45
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 45

catctgctag caatggcttc ctactttgcg ttg                               33


<210> SEQ ID NO 46
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 46

ttcaatggta ccttattggg cagtttgtcc ctt                               33


<210> SEQ ID NO 47
<211> LENGTH: 1569
<212> TYPE: DNA
<213> ORGANISM: Mokola virus
<220> FEATURE:
<221> NAME/KEY: CDS
<222> LOCATION: (1)..(1569)

<400> SEQUENCE: 47

atg aat ata cct tgc ttt gtt gtg att ctt gga ttc aca act aca tat       48
Met Asn Ile Pro Cys Phe Val Val Ile Leu Gly Phe Thr Thr Thr Tyr
1               5                   10                  15

tct ctt ggg gaa ttt cct ttg tac aca att ccc gag aag ata gag aaa       96
Ser Leu Gly Glu Phe Pro Leu Tyr Thr Ile Pro Glu Lys Ile Glu Lys
            20                  25                  30

tgg acc cca ata gac atg atc cat cta agc tgc ccc aac aac tta tta      144
Trp Thr Pro Ile Asp Met Ile His Leu Ser Cys Pro Asn Asn Leu Leu
        35                  40                  45

tcc gag gag gaa ggt tgc aat aca gag tcg ccc ctc acc tac ttc gag      192
Ser Glu Glu Glu Gly Cys Asn Thr Glu Ser Pro Leu Thr Tyr Phe Glu
    50                  55                  60

ctc aag agt ggt tac tta gct cat cag aaa gtt ccg ggg ttt acc tgt      240
Leu Lys Ser Gly Tyr Leu Ala His Gln Lys Val Pro Gly Phe Thr Cys
65                  70                  75                  80

aca ggg gta gtg aat gag gcg gag aca tac aca aat ttt gtc ggg tat      288
Thr Gly Val Val Asn Glu Ala Glu Thr Tyr Thr Asn Phe Val Gly Tyr
                85                  90                  95
```

```
gtc acc aca aac ttc aaa aga aaa cac ttt aag cct aca gtc tcc gcc      336
Val Thr Thr Asn Phe Lys Arg Lys His Phe Lys Pro Thr Val Ser Ala
            100                 105                 110

tgt cgt gat gcc tac aac tgg aaa gcg tcc ggg gat ccc agg tat gag      384
Cys Arg Asp Ala Tyr Asn Trp Lys Ala Ser Gly Asp Pro Arg Tyr Glu
        115                 120                 125

gag tca ctg cac act cct tac cct gac agc agc tgg ttg aga act gta      432
Glu Ser Leu His Thr Pro Tyr Pro Asp Ser Ser Trp Leu Arg Thr Val
    130                 135                 140

act acc acc aaa gaa tcc ctt ctt ata ata tcg cct agc atc gtg gag      480
Thr Thr Thr Lys Glu Ser Leu Leu Ile Ile Ser Pro Ser Ile Val Glu
145                 150                 155                 160

atg gat gta tat ggc agg act ctc cat tcc ccc atg ttc cct tca ggg      528
Met Asp Val Tyr Gly Arg Thr Leu His Ser Pro Met Phe Pro Ser Gly
                165                 170                 175

ata tgt tct aag ctc tat ccc tct gtt cca tcc tgc aaa acc aac cat      576
Ile Cys Ser Lys Leu Tyr Pro Ser Val Pro Ser Cys Lys Thr Asn His
            180                 185                 190

gat tac aca tta tgg ctg cca gaa gat cct agt ttg agt tta atc tgt      624
Asp Tyr Thr Leu Trp Leu Pro Glu Asp Pro Ser Leu Ser Leu Ile Cys
        195                 200                 205

gat att ttc act tct ggc agc gga agg aag gcc atg aat ggg tcc cgc      672
Asp Ile Phe Thr Ser Gly Ser Gly Arg Lys Ala Met Asn Gly Ser Arg
    210                 215                 220

atc tgc gga ttc aag gat gaa agg gga ttt tac aga tct ttg aaa ggc      720
Ile Cys Gly Phe Lys Asp Glu Arg Gly Phe Tyr Arg Ser Leu Lys Gly
225                 230                 235                 240

gct tgt aag ctg aca ttg tgc gga agg cct ggg atc aga tta ttt gac      768
Ala Cys Lys Leu Thr Leu Cys Gly Arg Pro Gly Ile Arg Leu Phe Asp
                245                 250                 255

gga act tgg gtc tct ttt aca agg cca gaa gtt cac gtg tgg tgc acc      816
Gly Thr Trp Val Ser Phe Thr Arg Pro Glu Val His Val Trp Cys Thr
            260                 265                 270

cct aac caa ttg gtc aat ata cac aat gat aga ata gat gag atc gag      864
Pro Asn Gln Leu Val Asn Ile His Asn Asp Arg Ile Asp Glu Ile Glu
        275                 280                 285

cac ctg att gtt gaa gac att gtc aaa aga agg gag gag tgt tta gac      912
His Leu Ile Val Glu Asp Ile Val Lys Arg Arg Glu Glu Cys Leu Asp
    290                 295                 300

act cta gag aca gta ttt atg tct caa tca att agt ttt agg agg ttg      960
Thr Leu Glu Thr Val Phe Met Ser Gln Ser Ile Ser Phe Arg Arg Leu
305                 310                 315                 320

agc cac ttt cgg aaa ttg gtt ccc gga tat ggg aaa gct tac acc att     1008
Ser His Phe Arg Lys Leu Val Pro Gly Tyr Gly Lys Ala Tyr Thr Ile
                325                 330                 335

ttg aat ggt agc ctg atg gaa gca aat gtc tac tat aaa aga gtt gac     1056
Leu Asn Gly Ser Leu Met Glu Ala Asn Val Tyr Tyr Lys Arg Val Asp
            340                 345                 350

agg tgg gcg gac att tta ccc tct aag gga tgt ctg aaa gtc ggg caa     1104
Arg Trp Ala Asp Ile Leu Pro Ser Lys Gly Cys Leu Lys Val Gly Gln
        355                 360                 365

caa tgt atg gac cct gtc aac gga gtc ctc ttc aat ggg att atc aaa     1152
Gln Cys Met Asp Pro Val Asn Gly Val Leu Phe Asn Gly Ile Ile Lys
    370                 375                 380

ggt cca gat ggc cag atc ttg atc cct gaa atg cag tca gag cag ctc     1200
Gly Pro Asp Gly Gln Ile Leu Ile Pro Glu Met Gln Ser Glu Gln Leu
385                 390                 395                 400

aag cag cat atg gac tta tta aag gca gca gtg ttc cct ctc aga cat     1248
Lys Gln His Met Asp Leu Leu Lys Ala Ala Val Phe Pro Leu Arg His
                405                 410                 415
```

```
cct tta atc agc caa gac gcc atc ttt aag aaa gac ggg gag gca gat     1296
Pro Leu Ile Ser Gln Asp Ala Ile Phe Lys Lys Asp Gly Glu Ala Asp
            420                 425                 430

gat ttt gtg gac ctc cat atg cca gat gta cac aaa tct gta tca gat     1344
Asp Phe Val Asp Leu His Met Pro Asp Val His Lys Ser Val Ser Asp
        435                 440                 445

gtc gac ttg ggt ttg cct cac tgg ggg ttt tgg atg ttg atc ggg gca     1392
Val Asp Leu Gly Leu Pro His Trp Gly Phe Trp Met Leu Ile Gly Ala
    450                 455                 460

act gta gtg gca ttt ttg gtc ttg gtg tgt ctg ctc cgt gtc tgc tgt     1440
Thr Val Val Ala Phe Leu Val Leu Val Cys Leu Leu Arg Val Cys Cys
465                 470                 475                 480

aag aga gtg agg agg aga ggt tca cga cgt aca act cag gag atc ccc     1488
Lys Arg Val Arg Arg Arg Gly Ser Arg Arg Thr Thr Gln Glu Ile Pro
                485                 490                 495

ctc aac gtt tcc tct gtc ccc gtc cct cgg gcc aca gtg gtg tca tca     1536
Leu Asn Val Ser Ser Val Pro Val Pro Arg Ala Thr Val Val Ser Ser
            500                 505                 510

tgg gag tcc tat aaa ggg ctt cca ggt aca tga                         1569
Trp Glu Ser Tyr Lys Gly Leu Pro Gly Thr
        515                 520


<210> SEQ ID NO 48
<211> LENGTH: 522
<212> TYPE: PRT
<213> ORGANISM: Mokola virus

<400> SEQUENCE: 48

Met Asn Ile Pro Cys Phe Val Val Ile Leu Gly Phe Thr Thr Thr Tyr
1               5                   10                  15

Ser Leu Gly Glu Phe Pro Leu Tyr Thr Ile Pro Glu Lys Ile Glu Lys
            20                  25                  30

Trp Thr Pro Ile Asp Met Ile His Leu Ser Cys Pro Asn Asn Leu Leu
        35                  40                  45

Ser Glu Glu Glu Gly Cys Asn Thr Glu Ser Pro Leu Thr Tyr Phe Glu
    50                  55                  60

Leu Lys Ser Gly Tyr Leu Ala His Gln Lys Val Pro Gly Phe Thr Cys
65                  70                  75                  80

Thr Gly Val Val Asn Glu Ala Glu Thr Tyr Thr Asn Phe Val Gly Tyr
                85                  90                  95

Val Thr Thr Asn Phe Lys Arg Lys His Phe Lys Pro Thr Val Ser Ala
            100                 105                 110

Cys Arg Asp Ala Tyr Asn Trp Lys Ala Ser Gly Asp Pro Arg Tyr Glu
        115                 120                 125

Glu Ser Leu His Thr Pro Tyr Pro Asp Ser Ser Trp Leu Arg Thr Val
    130                 135                 140

Thr Thr Thr Lys Glu Ser Leu Leu Ile Ile Ser Pro Ser Ile Val Glu
145                 150                 155                 160

Met Asp Val Tyr Gly Arg Thr Leu His Ser Pro Met Phe Pro Ser Gly
                165                 170                 175

Ile Cys Ser Lys Leu Tyr Pro Ser Val Pro Ser Cys Lys Thr Asn His
            180                 185                 190

Asp Tyr Thr Leu Trp Leu Pro Glu Asp Pro Ser Leu Ser Leu Ile Cys
        195                 200                 205

Asp Ile Phe Thr Ser Gly Ser Gly Arg Lys Ala Met Asn Gly Ser Arg
    210                 215                 220
```

```
Ile Cys Gly Phe Lys Asp Glu Arg Gly Phe Tyr Arg Ser Leu Lys Gly
225                 230                 235                 240

Ala Cys Lys Leu Thr Leu Cys Gly Arg Pro Gly Ile Arg Leu Phe Asp
                245                 250                 255

Gly Thr Trp Val Ser Phe Thr Arg Pro Glu Val His Val Trp Cys Thr
            260                 265                 270

Pro Asn Gln Leu Val Asn Ile His Asn Asp Arg Ile Asp Glu Ile Glu
        275                 280                 285

His Leu Ile Val Glu Asp Ile Val Lys Arg Arg Glu Glu Cys Leu Asp
    290                 295                 300

Thr Leu Glu Thr Val Phe Met Ser Gln Ser Ile Ser Phe Arg Arg Leu
305                 310                 315                 320

Ser His Phe Arg Lys Leu Val Pro Gly Tyr Gly Lys Ala Tyr Thr Ile
                325                 330                 335

Leu Asn Gly Ser Leu Met Glu Ala Asn Val Tyr Tyr Lys Arg Val Asp
            340                 345                 350

Arg Trp Ala Asp Ile Leu Pro Ser Lys Gly Cys Leu Lys Val Gly Gln
        355                 360                 365

Gln Cys Met Asp Pro Val Asn Gly Val Leu Phe Asn Gly Ile Ile Lys
    370                 375                 380

Gly Pro Asp Gly Gln Ile Leu Ile Pro Glu Met Gln Ser Glu Gln Leu
385                 390                 395                 400

Lys Gln His Met Asp Leu Leu Lys Ala Ala Val Phe Pro Leu Arg His
                405                 410                 415

Pro Leu Ile Ser Gln Asp Ala Ile Phe Lys Lys Asp Gly Glu Ala Asp
            420                 425                 430

Asp Phe Val Asp Leu His Met Pro Asp Val His Lys Ser Val Ser Asp
        435                 440                 445

Val Asp Leu Gly Leu Pro His Trp Gly Phe Trp Met Leu Ile Gly Ala
    450                 455                 460

Thr Val Val Ala Phe Leu Val Leu Val Cys Leu Leu Arg Val Cys Cys
465                 470                 475                 480

Lys Arg Val Arg Arg Arg Gly Ser Arg Arg Thr Thr Gln Glu Ile Pro
                485                 490                 495

Leu Asn Val Ser Ser Val Pro Val Pro Arg Ala Thr Val Val Ser Ser
            500                 505                 510

Trp Glu Ser Tyr Lys Gly Leu Pro Gly Thr
        515                 520


<210> SEQ ID NO 49
<211> LENGTH: 1578
<212> TYPE: DNA
<213> ORGANISM: West Caucasian bat virus
<220> FEATURE:
<221> NAME/KEY: CDS
<222> LOCATION: (1)..(1578)

<400> SEQUENCE: 49

atg gct tcc tac ttt gcg ttg gtc ttg aac ggg atc tct atg gtt ttc       48
Met Ala Ser Tyr Phe Ala Leu Val Leu Asn Gly Ile Ser Met Val Phe
1               5                   10                  15

agt caa ggt ctt ttc ccc ctt tac act atc cct gac cat ctg gga cca       96
Ser Gln Gly Leu Phe Pro Leu Tyr Thr Ile Pro Asp His Leu Gly Pro
            20                  25                  30

tgg acc ccc ata gat cta agt cac ctt cac tgc ccg aac aat ctt tat      144
Trp Thr Pro Ile Asp Leu Ser His Leu His Cys Pro Asn Asn Leu Tyr
        35                  40                  45
```

```
act gat gcc tct tat tgt aca act gaa caa agc ata acc tac aca gag      192
Thr Asp Ala Ser Tyr Cys Thr Thr Glu Gln Ser Ile Thr Tyr Thr Glu
    50                  55                  60

ttg aag gtc gga tca tct gtg tca caa aaa atc ccc gga ttt aca tgt      240
Leu Lys Val Gly Ser Ser Val Ser Gln Lys Ile Pro Gly Phe Thr Cys
65                  70                  75                  80

acg ggg gta aga act gaa tct gta aca tat acc aac ttt gtt ggc tat      288
Thr Gly Val Arg Thr Glu Ser Val Thr Tyr Thr Asn Phe Val Gly Tyr
                85                  90                  95

gtg act acc acg ttc aag aaa aaa cac ttt cct cct aaa tcc agg gac      336
Val Thr Thr Thr Phe Lys Lys Lys His Phe Pro Pro Lys Ser Arg Asp
            100                 105                 110

tgt aga gag gcg tat gag agg aag aaa gca gga gat cct aga tat gaa      384
Cys Arg Glu Ala Tyr Glu Arg Lys Lys Ala Gly Asp Pro Arg Tyr Glu
        115                 120                 125

gag tct tta gcc cac cca tat cct gac aac agt tgg ctg aga aca gtg      432
Glu Ser Leu Ala His Pro Tyr Pro Asp Asn Ser Trp Leu Arg Thr Val
    130                 135                 140

act aca aca aag gat tcc tgg gtg atc atc gag ccc agt gta gtg gag      480
Thr Thr Thr Lys Asp Ser Trp Val Ile Ile Glu Pro Ser Val Val Glu
145                 150                 155                 160

tta gat ata tac aca agt gcc ttg tat tca cct ctt ttc aag gat gga      528
Leu Asp Ile Tyr Thr Ser Ala Leu Tyr Ser Pro Leu Phe Lys Asp Gly
                165                 170                 175

aca tgt tca aaa tct aga aca tat tcc ccc tac tgt cca acc aat cat      576
Thr Cys Ser Lys Ser Arg Thr Tyr Ser Pro Tyr Cys Pro Thr Asn His
            180                 185                 190

gac ttc acc att tgg atg cca gag agt gaa aac ata aga tct gcc tgt      624
Asp Phe Thr Ile Trp Met Pro Glu Ser Glu Asn Ile Arg Ser Ala Cys
        195                 200                 205

aat ctg ttt tcc aca agt aga ggg aaa cta gtc agg aac cgc aca tcc      672
Asn Leu Phe Ser Thr Ser Arg Gly Lys Leu Val Arg Asn Arg Thr Ser
    210                 215                 220

acc tgc ggg att atc gat gag aga ggg ctg ttc aga tca gtt aaa gga      720
Thr Cys Gly Ile Ile Asp Glu Arg Gly Leu Phe Arg Ser Val Lys Gly
225                 230                 235                 240

gca tgc aaa ata tca ata tgc ggt agg cag gga atc cgt tta gtg gat      768
Ala Cys Lys Ile Ser Ile Cys Gly Arg Gln Gly Ile Arg Leu Val Asp
                245                 250                 255

gga act tgg atg tct ttt aga tac tca gag tac tta cct gtg tgt tct      816
Gly Thr Trp Met Ser Phe Arg Tyr Ser Glu Tyr Leu Pro Val Cys Ser
            260                 265                 270

cca tca cag ctg atc aac acg cac gac atc aag gtc gat gag ctg gag      864
Pro Ser Gln Leu Ile Asn Thr His Asp Ile Lys Val Asp Glu Leu Glu
        275                 280                 285

aat gct ata gtt tta gac ttg att agg agg aga gaa gaa tgt ctt gac      912
Asn Ala Ile Val Leu Asp Leu Ile Arg Arg Arg Glu Glu Cys Leu Asp
    290                 295                 300

acc cta gaa aca att ttg atg tca gga tct gtg agt cac agg agg ctg      960
Thr Leu Glu Thr Ile Leu Met Ser Gly Ser Val Ser His Arg Arg Leu
305                 310                 315                 320

agt cat ttc aga aag ctg gtt cca gga tct ggg aag gct tac tct tat     1008
Ser His Phe Arg Lys Leu Val Pro Gly Ser Gly Lys Ala Tyr Ser Tyr
                325                 330                 335

ata aac ggc acc tta atg gaa tca gat gct cac tac atc aag gta gag     1056
Ile Asn Gly Thr Leu Met Glu Ser Asp Ala His Tyr Ile Lys Val Glu
            340                 345                 350

aat tgg tca gag gtc atc cca cac aaa gga tgt ctc atg gtc ggg ggc     1104
Asn Trp Ser Glu Val Ile Pro His Lys Gly Cys Leu Met Val Gly Gly
```

```
        355                 360                 365

aaa tgc tat gag cca gtc aat gat gtg tat ttc aac ggg atc att cgg      1152
Lys Cys Tyr Glu Pro Val Asn Asp Val Tyr Phe Asn Gly Ile Ile Arg
    370                 375                 380

gat tca aat aat cag atc ttg ata cct gag atg cag tcc agt ctt ctc      1200
Asp Ser Asn Asn Gln Ile Leu Ile Pro Glu Met Gln Ser Ser Leu Leu
385                 390                 395                 400

aga gaa cat gtt gac ctg ttg aag gct aat ata gtt ccg ttc agg cat      1248
Arg Glu His Val Asp Leu Leu Lys Ala Asn Ile Val Pro Phe Arg His
                405                 410                 415

cca atg tta ctt agg tcc ttc aca tct gac act gaa gaa gat atc gtc      1296
Pro Met Leu Leu Arg Ser Phe Thr Ser Asp Thr Glu Glu Asp Ile Val
            420                 425                 430

gag ttt gtc aac cct cat ctc caa gat acc cag aag ttg gtg tca gat      1344
Glu Phe Val Asn Pro His Leu Gln Asp Thr Gln Lys Leu Val Ser Asp
        435                 440                 445

atg gat ctc ggg tta tca gac tgg aag aga tat cta cta att gga tct      1392
Met Asp Leu Gly Leu Ser Asp Trp Lys Arg Tyr Leu Leu Ile Gly Ser
    450                 455                 460

ttg gcc gta gga gga gtg gta gca atc tta ttc atc gga aca tgt tgt      1440
Leu Ala Val Gly Gly Val Val Ala Ile Leu Phe Ile Gly Thr Cys Cys
465                 470                 475                 480

ctg aga tgt aga gca ggg aga aac aga aga aca atc cga tcc aat cat      1488
Leu Arg Cys Arg Ala Gly Arg Asn Arg Arg Thr Ile Arg Ser Asn His
                485                 490                 495

agg tca ttg tcc cat gac gtg gtg ttc cat aaa gat aag gat aaa gtg      1536
Arg Ser Leu Ser His Asp Val Val Phe His Lys Asp Lys Asp Lys Val
            500                 505                 510

att act tct tgg gaa tct tac aag gga caa act gcc caa taa              1578
Ile Thr Ser Trp Glu Ser Tyr Lys Gly Gln Thr Ala Gln
        515                 520                 525


<210> SEQ ID NO 50
<211> LENGTH: 525
<212> TYPE: PRT
<213> ORGANISM: West Caucasian bat virus

<400> SEQUENCE: 50

Met Ala Ser Tyr Phe Ala Leu Val Leu Asn Gly Ile Ser Met Val Phe
1               5                   10                  15

Ser Gln Gly Leu Phe Pro Leu Tyr Thr Ile Pro Asp His Leu Gly Pro
            20                  25                  30

Trp Thr Pro Ile Asp Leu Ser His Leu His Cys Pro Asn Asn Leu Tyr
        35                  40                  45

Thr Asp Ala Ser Tyr Cys Thr Thr Glu Gln Ser Ile Thr Tyr Thr Glu
    50                  55                  60

Leu Lys Val Gly Ser Ser Val Ser Gln Lys Ile Pro Gly Phe Thr Cys
65                  70                  75                  80

Thr Gly Val Arg Thr Glu Ser Val Thr Tyr Thr Asn Phe Val Gly Tyr
                85                  90                  95

Val Thr Thr Thr Phe Lys Lys Lys His Phe Pro Pro Lys Ser Arg Asp
            100                 105                 110

Cys Arg Glu Ala Tyr Glu Arg Lys Lys Ala Gly Asp Pro Arg Tyr Glu
        115                 120                 125

Glu Ser Leu Ala His Pro Tyr Pro Asp Asn Ser Trp Leu Arg Thr Val
    130                 135                 140

Thr Thr Thr Lys Asp Ser Trp Val Ile Ile Glu Pro Ser Val Val Glu
145                 150                 155                 160
```

```
Leu Asp Ile Tyr Thr Ser Ala Leu Tyr Ser Pro Leu Phe Lys Asp Gly
                165                 170                 175

Thr Cys Ser Lys Ser Arg Thr Tyr Ser Pro Tyr Cys Pro Thr Asn His
            180                 185                 190

Asp Phe Thr Ile Trp Met Pro Glu Ser Glu Asn Ile Arg Ser Ala Cys
        195                 200                 205

Asn Leu Phe Ser Thr Ser Arg Gly Lys Leu Val Arg Asn Arg Thr Ser
    210                 215                 220

Thr Cys Gly Ile Ile Asp Glu Arg Gly Leu Phe Arg Ser Val Lys Gly
225                 230                 235                 240

Ala Cys Lys Ile Ser Ile Cys Gly Arg Gln Gly Ile Arg Leu Val Asp
                245                 250                 255

Gly Thr Trp Met Ser Phe Arg Tyr Ser Glu Tyr Leu Pro Val Cys Ser
            260                 265                 270

Pro Ser Gln Leu Ile Asn Thr His Asp Ile Lys Val Asp Glu Leu Glu
        275                 280                 285

Asn Ala Ile Val Leu Asp Leu Ile Arg Arg Arg Glu Glu Cys Leu Asp
    290                 295                 300

Thr Leu Glu Thr Ile Leu Met Ser Gly Ser Val Ser His Arg Arg Leu
305                 310                 315                 320

Ser His Phe Arg Lys Leu Val Pro Gly Ser Gly Lys Ala Tyr Ser Tyr
                325                 330                 335

Ile Asn Gly Thr Leu Met Glu Ser Asp Ala His Tyr Ile Lys Val Glu
            340                 345                 350

Asn Trp Ser Glu Val Ile Pro His Lys Gly Cys Leu Met Val Gly Gly
        355                 360                 365

Lys Cys Tyr Glu Pro Val Asn Asp Val Tyr Phe Asn Gly Ile Ile Arg
    370                 375                 380

Asp Ser Asn Asn Gln Ile Leu Ile Pro Glu Met Gln Ser Ser Leu Leu
385                 390                 395                 400

Arg Glu His Val Asp Leu Leu Lys Ala Asn Ile Val Pro Phe Arg His
                405                 410                 415

Pro Met Leu Leu Arg Ser Phe Thr Ser Asp Thr Glu Glu Asp Ile Val
            420                 425                 430

Glu Phe Val Asn Pro His Leu Gln Asp Thr Gln Lys Leu Val Ser Asp
        435                 440                 445

Met Asp Leu Gly Leu Ser Asp Trp Lys Arg Tyr Leu Leu Ile Gly Ser
    450                 455                 460

Leu Ala Val Gly Gly Val Val Ala Ile Leu Phe Ile Gly Thr Cys Cys
465                 470                 475                 480

Leu Arg Cys Arg Ala Gly Arg Asn Arg Arg Thr Ile Arg Ser Asn His
                485                 490                 495

Arg Ser Leu Ser His Asp Val Val Phe His Lys Asp Lys Asp Lys Val
            500                 505                 510

Ile Thr Ser Trp Glu Ser Tyr Lys Gly Gln Thr Ala Gln
        515                 520                 525
```

<210> SEQ ID NO 51
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 51

```
cgactgcaga tgagtcaact aaatttgata cccttttc                             39


<210> SEQ ID NO 52
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 52

ccgtacgtat cagacattag aggtaccctt ataagattcc ca                        42


<210> SEQ ID NO 53
<211> LENGTH: 1569
<212> TYPE: DNA
<213> ORGANISM: Lagos vat virus
<220> FEATURE:
<221> NAME/KEY: CDS
<222> LOCATION: (1)..(1569)

<400> SEQUENCE: 53

atg agt caa cta aat ttg ata ccc ttt ttc tgt gta att ata gtc ttg       48
Met Ser Gln Leu Asn Leu Ile Pro Phe Phe Cys Val Ile Ile Val Leu
1               5                   10                  15

tct gta gag gac ttt cct cta tat aca att cct gaa aag ata ggt cct       96
Ser Val Glu Asp Phe Pro Leu Tyr Thr Ile Pro Glu Lys Ile Gly Pro
            20                  25                  30

tgg act ccg atc gac ctg atc cat ctg agc tgt cct aat aat ttg cag      144
Trp Thr Pro Ile Asp Leu Ile His Leu Ser Cys Pro Asn Asn Leu Gln
        35                  40                  45

tca gag gat gaa gga tgt ggt acc tca tca gtc ttc agt tat gta gag      192
Ser Glu Asp Glu Gly Cys Gly Thr Ser Ser Val Phe Ser Tyr Val Glu
    50                  55                  60

ctc aag aca ggt tat ctc act cat cag aaa gtg tct ggg ttc acc tgt      240
Leu Lys Thr Gly Tyr Leu Thr His Gln Lys Val Ser Gly Phe Thr Cys
65                  70                  75                  80

aca gga gtg gtt aat gag gct gtc aca tac act aac ttt gtc gga tat      288
Thr Gly Val Val Asn Glu Ala Val Thr Tyr Thr Asn Phe Val Gly Tyr
                85                  90                  95

gtg aca acc acc ttt aag cgg aaa cat ttc aag ccg acg gca ttg gct      336
Val Thr Thr Thr Phe Lys Arg Lys His Phe Lys Pro Thr Ala Leu Ala
            100                 105                 110

tgc aga gat gct tat cat tgg aag att tct ggg gat cca agg tat gag      384
Cys Arg Asp Ala Tyr His Trp Lys Ile Ser Gly Asp Pro Arg Tyr Glu
        115                 120                 125

gag tct ctc cac aca cca tat cct gac aac agc tgg ttg agg aca gtt      432
Glu Ser Leu His Thr Pro Tyr Pro Asp Asn Ser Trp Leu Arg Thr Val
    130                 135                 140

acc aca acc aaa gaa tct ctt gtg ata atc tct cca agc att gtg gag      480
Thr Thr Thr Lys Glu Ser Leu Val Ile Ile Ser Pro Ser Ile Val Glu
145                 150                 155                 160

atg gat gta tat agt aga aca ctt cat tct ccc atg ttt ccc acc ggg      528
Met Asp Val Tyr Ser Arg Thr Leu His Ser Pro Met Phe Pro Thr Gly
                165                 170                 175

acc tgt tct agg ttc tat ccg tca tcc cct tct tgt gcc aca aat cat      576
Thr Cys Ser Arg Phe Tyr Pro Ser Ser Pro Ser Cys Ala Thr Asn His
            180                 185                 190

gat tac act tta tgg ctt cca gat gac cct aat ctg agt ttg gca tgt      624
Asp Tyr Thr Leu Trp Leu Pro Asp Asp Pro Asn Leu Ser Leu Ala Cys
        195                 200                 205

gat atc ttt gtg acc agc aca ggg aaa aag tca atg aat ggc tct aga      672
```

-continued

```
Asp Ile Phe Val Thr Ser Thr Gly Lys Lys Ser Met Asn Gly Ser Arg
    210                 215                 220

atg tgt gga ttt aca gac gag aga ggg tat tac cgg aca ata aaa gga      720
Met Cys Gly Phe Thr Asp Glu Arg Gly Tyr Tyr Arg Thr Ile Lys Gly
225                 230                 235                 240

gct tgt aaa ctg aca tta tgt ggg aaa cca ggt ttg agg tta ttt gat      768
Ala Cys Lys Leu Thr Leu Cys Gly Lys Pro Gly Leu Arg Leu Phe Asp
                245                 250                 255

ggc aca tgg ata tcc ttc ccc cgc ccg gaa gtc act acc cgg tgc ctt      816
Gly Thr Trp Ile Ser Phe Pro Arg Pro Glu Val Thr Thr Arg Cys Leu
            260                 265                 270

cct aat cag tta gtc aat att cac aac aat agg ata gat gaa gtt gag      864
Pro Asn Gln Leu Val Asn Ile His Asn Asn Arg Ile Asp Glu Val Glu
        275                 280                 285

cat ctg att gta gaa gat ctc att cga aaa aga gaa gag tgt ttg gac      912
His Leu Ile Val Glu Asp Leu Ile Arg Lys Arg Glu Glu Cys Leu Asp
    290                 295                 300

act tta gag aca gtt tta atg tcc aaa tca atc agt ttt aga cga cta      960
Thr Leu Glu Thr Val Leu Met Ser Lys Ser Ile Ser Phe Arg Arg Leu
305                 310                 315                 320

agt cac ttc aga aaa tta gtg cca gga tat ggg aag gct tac act att     1008
Ser His Phe Arg Lys Leu Val Pro Gly Tyr Gly Lys Ala Tyr Thr Ile
                325                 330                 335

tta aat ggg agc tta atg gaa act aac gtt cat tat tta aag gtt gac     1056
Leu Asn Gly Ser Leu Met Glu Thr Asn Val His Tyr Leu Lys Val Asp
            340                 345                 350

aat tgg agt gaa ata ctg cct tcc aag gga tgt tta aaa ata aac aat     1104
Asn Trp Ser Glu Ile Leu Pro Ser Lys Gly Cys Leu Lys Ile Asn Asn
        355                 360                 365

cag tgt gtt gct cat tat aag ggg gtc ttc ttt aac ggg atc atc aag     1152
Gln Cys Val Ala His Tyr Lys Gly Val Phe Phe Asn Gly Ile Ile Lys
    370                 375                 380

gga cca gat ggt cat att tta atc ccc gag atg cag tca agt ttg ttg     1200
Gly Pro Asp Gly His Ile Leu Ile Pro Glu Met Gln Ser Ser Leu Leu
385                 390                 395                 400

aaa cag cac atg gac ctc ttg aag gca gcg gtt ttt ccc ttg aaa cat     1248
Lys Gln His Met Asp Leu Leu Lys Ala Ala Val Phe Pro Leu Lys His
                405                 410                 415

cct ctg att gaa ccg ggc tct ttg ttc aat aag gat ggt gat gcc gat     1296
Pro Leu Ile Glu Pro Gly Ser Leu Phe Asn Lys Asp Gly Asp Ala Asp
            420                 425                 430

gaa ttt gtt gat gtc cac atg cct gat gta cat aag ttg gta tca gat     1344
Glu Phe Val Asp Val His Met Pro Asp Val His Lys Leu Val Ser Asp
        435                 440                 445

gtc gac ttg ggg cta ccc gat tgg agc ctt tat gcg ttg ata ggg gca     1392
Val Asp Leu Gly Leu Pro Asp Trp Ser Leu Tyr Ala Leu Ile Gly Ala
    450                 455                 460

act att ata gct ttc ttt ata ctg ata tgt ctt att cgt atc tgc tgc     1440
Thr Ile Ile Ala Phe Phe Ile Leu Ile Cys Leu Ile Arg Ile Cys Cys
465                 470                 475                 480

aag aag ggg ggt cgg aga aac tct ccc aca aat aga cct gat ctt cct     1488
Lys Lys Gly Gly Arg Arg Asn Ser Pro Thr Asn Arg Pro Asp Leu Pro
                485                 490                 495

ata ggg ttg tct act aca cct caa ccc aag tct aaa gtg ata tca tca     1536
Ile Gly Leu Ser Thr Thr Pro Gln Pro Lys Ser Lys Val Ile Ser Ser
            500                 505                 510

tgg gaa tct tat aag ggt acc tct aat gtc tga                         1569
Trp Glu Ser Tyr Lys Gly Thr Ser Asn Val
        515                 520
```

<210> SEQ ID NO 54
<211> LENGTH: 522
<212> TYPE: PRT
<213> ORGANISM: Lagos vat virus

<400> SEQUENCE: 54

```
Met Ser Gln Leu Asn Leu Ile Pro Phe Phe Cys Val Ile Ile Val Leu
1               5                   10                  15

Ser Val Glu Asp Phe Pro Leu Tyr Thr Ile Pro Glu Lys Ile Gly Pro
            20                  25                  30

Trp Thr Pro Ile Asp Leu Ile His Leu Ser Cys Pro Asn Asn Leu Gln
        35                  40                  45

Ser Glu Asp Glu Gly Cys Gly Thr Ser Ser Val Phe Ser Tyr Val Glu
    50                  55                  60

Leu Lys Thr Gly Tyr Leu Thr His Gln Lys Val Ser Gly Phe Thr Cys
65                  70                  75                  80

Thr Gly Val Val Asn Glu Ala Val Thr Tyr Thr Asn Phe Val Gly Tyr
                85                  90                  95

Val Thr Thr Thr Phe Lys Arg Lys His Phe Lys Pro Thr Ala Leu Ala
            100                 105                 110

Cys Arg Asp Ala Tyr His Trp Lys Ile Ser Gly Asp Pro Arg Tyr Glu
        115                 120                 125

Glu Ser Leu His Thr Pro Tyr Pro Asp Asn Ser Trp Leu Arg Thr Val
    130                 135                 140

Thr Thr Thr Lys Glu Ser Leu Val Ile Ile Ser Pro Ser Ile Val Glu
145                 150                 155                 160

Met Asp Val Tyr Ser Arg Thr Leu His Ser Pro Met Phe Pro Thr Gly
                165                 170                 175

Thr Cys Ser Arg Phe Tyr Pro Ser Ser Pro Ser Cys Ala Thr Asn His
            180                 185                 190

Asp Tyr Thr Leu Trp Leu Pro Asp Asp Pro Asn Leu Ser Leu Ala Cys
        195                 200                 205

Asp Ile Phe Val Thr Ser Thr Gly Lys Lys Ser Met Asn Gly Ser Arg
    210                 215                 220

Met Cys Gly Phe Thr Asp Glu Arg Gly Tyr Tyr Arg Thr Ile Lys Gly
225                 230                 235                 240

Ala Cys Lys Leu Thr Leu Cys Gly Lys Pro Gly Leu Arg Leu Phe Asp
                245                 250                 255

Gly Thr Trp Ile Ser Phe Pro Arg Pro Glu Val Thr Thr Arg Cys Leu
            260                 265                 270

Pro Asn Gln Leu Val Asn Ile His Asn Asn Arg Ile Asp Glu Val Glu
        275                 280                 285

His Leu Ile Val Glu Asp Leu Ile Arg Lys Arg Glu Glu Cys Leu Asp
    290                 295                 300

Thr Leu Glu Thr Val Leu Met Ser Lys Ser Ile Ser Phe Arg Arg Leu
305                 310                 315                 320

Ser His Phe Arg Lys Leu Val Pro Gly Tyr Gly Lys Ala Tyr Thr Ile
                325                 330                 335

Leu Asn Gly Ser Leu Met Glu Thr Asn Val His Tyr Leu Lys Val Asp
            340                 345                 350

Asn Trp Ser Glu Ile Leu Pro Ser Lys Gly Cys Leu Lys Ile Asn Asn
        355                 360                 365

Gln Cys Val Ala His Tyr Lys Gly Val Phe Phe Asn Gly Ile Ile Lys
    370                 375                 380
```

```
Gly Pro Asp Gly His Ile Leu Ile Pro Glu Met Gln Ser Ser Leu Leu
385                 390                 395                 400

Lys Gln His Met Asp Leu Leu Lys Ala Ala Val Phe Pro Leu Lys His
                405                 410                 415

Pro Leu Ile Glu Pro Gly Ser Leu Phe Asn Lys Asp Gly Asp Ala Asp
            420                 425                 430

Glu Phe Val Asp Val His Met Pro Asp Val His Lys Leu Val Ser Asp
        435                 440                 445

Val Asp Leu Gly Leu Pro Asp Trp Ser Leu Tyr Ala Leu Ile Gly Ala
    450                 455                 460

Thr Ile Ile Ala Phe Phe Ile Leu Ile Cys Leu Ile Arg Ile Cys Cys
465                 470                 475                 480

Lys Lys Gly Gly Arg Arg Asn Ser Pro Thr Asn Arg Pro Asp Leu Pro
                485                 490                 495

Ile Gly Leu Ser Thr Thr Pro Gln Pro Lys Ser Lys Val Ile Ser Ser
            500                 505                 510

Trp Glu Ser Tyr Lys Gly Thr Ser Asn Val
        515                 520
```